United States Patent
Zhang

(10) Patent No.: US 9,771,333 B2
(45) Date of Patent: Sep. 26, 2017

(54) QUINAZOLINE DERIVATIVES AS TAM FAMILY KINASE INHIBITORS

(71) Applicant: SIGNALCHEM LIFESCIENCES CORP., Richmond, British Columbia (CA)

(72) Inventor: Zaihui Zhang, Richmond (CA)

(73) Assignee: SignalChem Lifesciences Corp., Richmond, BC (CA)

( * ) Notice: Subject to any disclaimer, the term of this patent is extended or adjusted under 35 U.S.C. 154(b) by 0 days.

(21) Appl. No.: 15/038,038

(22) PCT Filed: Nov. 19, 2014

(86) PCT No.: PCT/US2014/066467
§ 371 (c)(1),
(2) Date: May 19, 2016

(87) PCT Pub. No.: WO2015/077375
PCT Pub. Date: May 28, 2015

(65) Prior Publication Data
US 2016/0297775 A1 Oct. 13, 2016

Related U.S. Application Data

(60) Provisional application No. 61/906,779, filed on Nov. 20, 2013.

(51) Int. Cl.
| | |
|---|---|
| *C07D 239/88* | (2006.01) |
| *C07D 405/12* | (2006.01) |
| *C07D 239/93* | (2006.01) |
| *C07D 417/12* | (2006.01) |
| *C07D 405/14* | (2006.01) |
| *C07D 413/14* | (2006.01) |
| *C07D 417/14* | (2006.01) |
| *C07D 413/12* | (2006.01) |

(52) U.S. Cl.
CPC ......... *C07D 239/88* (2013.01); *C07D 239/93* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 3,971,783 A * | 7/1976 | Barnish | C07D 417/12 544/283 |
| 5,710,158 A | 1/1998 | Myers et al. | |
| 2007/0082921 A1 | 4/2007 | Hennequin et al. | |
| 2008/0188467 A1* | 8/2008 | Wong | C07D 403/12 514/224.2 |
| 2010/0280042 A1 | 11/2010 | Hennequin et al. | |
| 2011/0034459 A1 | 2/2011 | Adibhatla Kali Satya et al. | |
| 2011/0118245 A1 | 5/2011 | Abraham et al. | |

FOREIGN PATENT DOCUMENTS

| | | |
|---|---|---|
| WO | 2010136475 | 12/2010 |
| WO | 2011056740 | 5/2011 |
| WO | 2013074633 | 5/2013 |

OTHER PUBLICATIONS

PCT International Search Report and Written Opinion for PCT/US2014/066467 dated Jan. 26, 2015.
European Extended Search Report for Application No. 14864125.1 dated Mar. 16, 2017.
Zhang Ying et al., "Synthesis and anticancer activities of 5,6,7-trimethoxy-N-phenyl(ethyl)-4-aminoquinazoline derivatives", European Journal of Medicinal Chemistry, v. 66, Jun. 7, 2013, pp. 335-344.
Santhosh Kumar Bairy et al., "Three-Dimensional Quantitative Structure-Activity Relationship Studies on c-Src Inhibitors Based on Different Docking Methods", Chemical Biology & Drug Design, v. 73, No. 4, Apr. 1, 2009, pp. 416-427.
Rosa M. Suarez et al., "Inhibitors of the TAM subfamily of tyrosine kinases: Synthesis and biological evaluation", European Journal of Medicinal Chemistry, v. 61, Mar. 1, 2013, pp. 2-25.
Barlaam B. et al., "New heterocyclic analogues of 4-(2-chloro-5-methoxyanilino)quinazolines as potent and selective c-Src kinase inhibitors", Bioorganic & Medicinal Chemistry Letters, Pergamon, Amsterdam, NL, v. 15, No. 24, Dec. 15, 2005, pp. 5446-5449.

* cited by examiner

*Primary Examiner* — Kristin Vajda
(74) *Attorney, Agent, or Firm* — BioMed IP

(57) ABSTRACT

Disclosed are compounds, compositions and methods for treating diseases, syndromes, conditions and disorders that are affected by the modulation of the activity of, e.g., the inhibition of, one or more members of the TAM family kinases.

26 Claims, No Drawings

QUINAZOLINE DERIVATIVES AS TAM FAMILY KINASE INHIBITORS

CROSS-REFERENCE TO RELATED APPLICATION

This application is a national phase application under 35 U.S.C. §371 of International Application No. PCT/US2014/066467, filed Nov. 14, 2014, which claims the benefit under 35 U.S.C. §119(e) of U.S. Provisional Patent Application No. 61/906,779 filed Nov. 20, 2013, which applications are incorporated herein by reference in their entirety.

FIELD OF THE INVENTION

The present invention provides compounds that inhibit protein kinases Tyro3, Axl and Mer (TAM family kinases), prodrugs of the compounds, intermediates and methods of synthesizing the compounds and/or prodrugs, pharmaceutical compositions comprising the compounds and/or prodrugs and methods of using the compounds and/or prodrugs in a variety of contexts, including, for example, in the treatment and/or prevention of various diseases that are responsive to TAM family kinase inhibition and/or that are mediated, at least in part, by undesirable TAM family kinase activity.

BACKGROUND

The receptor tyrosine kinases (RTKs) are transmembrane proteins and function as sensors for extracellular ligands, which transduce signals from extracellular medium to the cytoplasm. Their activation leads to the recruitment, phosphorylation, and activation of the downstream signaling pathways, which ultimately regulate cellular functions such as proliferation, growth, differentiation and motility. Abnormal overexpression levels and/or enhanced activities of RTKs have been associated with a variety of human cancers, leading to a strong interest in the development of inhibitors against these kinases.

Tyro-3, Axl, and Mer constitute the TAM family of RTKs characterized by a conserved sequence within the kinase domain and adhesion molecule-like extracellular domains. With varying degree of specificity and affinity, TAM kinases can be activated by the vitamin K-dependent ligand Gas6 and/or Protein S. Strong evidence supports their association with both cancer (gain-in-function) and autoimmunity (loss-of-function). TAM kinase signaling has been implicated in a myriad of cellular responses, many of which are the hallmarks of cancer, including proliferation, survival, migration, invasion and angiogenesis. In addition, TAM plays pivotal roles innate immunity through inhibiting inflammation in macrophages and dendritic cells and promoting the phagocytosis of apoptotic cells. While the oncogenic activity of TAM kinases appears to be mediated via PI3K/AKT pathway, the JAK-STAT pathway is critical for their roles in immune responses. Overexpression of TAM kinases has been observed in over 20 human cancers. The level of their expression was shown to correlate with shorter progression-free and overall survival and their up-regulation has been linked to cancer resistance to cytotoxic drugs and targeted therapies.

While broadly expressed in various human tumor cell lines, Tyro3, Axl, and Mer exhibit their respective tissue-specific expression patterns. Tyro-3 is highly expressed in the nervous system whereas, Axl is expressed ubiquitously. Higher level of Mer is often found in hematopoietic lineages such as in monocytes/macrophages, dendritic cells, NK cells, NKT cells, megakaryocytes, and platelets.

Compared to Axl and Mer, Tyro3 is the least studied kinase of the TAM family. Implication of Tyro3 in tumorigenesis was only recently substantiated by recent studies, which revealed Tyro3 is a potential oncogene in melanoma that is linked to poorer outcome of patients suffering from melanoma regardless the BRAF or NRAS status by conferring survival advantage to melanoma cells. It was also identified as one of kinases significantly up-regulated in lung cancer by a phosphoproteomic screen. High level of Tyro3 expression has also been correlated with thyroid cancer.

As the founding member of the TAM kinase family, Axl was discovered as a transforming gene in chronic myelogenous leukemia (CML). Axl overexpression has since been reported in a wide range of human malignancies and is associated with invasiveness and metastasis in lung, prostate, breast and pancreatic cancer. Axl is also an important regulator of breast cancer metastasis and EMT. Activation of the Axl kinase confers resistance to EGFR targeted therapy in lung cancer. Upregulation of Axl has been implicated as a mechanism of resistance to imatinib in CML and gastrointestinal stromal tumors and to lapatinib in breast cancer. Axl expression has also been associated with chemoresistance in AML, NSCLC and ovarian cancer.

Mer is overexpressed/overactivated in a wide variety of cancers and has been established as a therapeutic target in hematopoietic malignancies and solid tumors including leukemia, non-small cell lung cancer, glioblastoma, melanoma, prostate cancer, breast cancer, colon cancer, gastric cancer, pituitary adenomas, and rhabdomyosarcomas. Oncogenic potential of Mer is mediated through the activation of several canonical oncogenic signaling pathways including the mitogen-activated protein kinase and phosphoinositide 3-kinase pathways, as well as regulation of signal transducer and activator of transcription family members, migration-associated proteins including the focal adhesion kinase and myosin light chain 2, and prosurvival proteins such as survivin and Bcl-2. In neoplastic cells, these signaling events result in functional phenotypes such as decreased apoptosis, increased migration, chemoresistance, increased colony formation, and increased tumor formation in murine models. Conversely, Mer inhibition by genetic or pharmacologic means can reverse these pro-oncogenic phenotypes.

The following literature reports small molecule inhibitors of Tyro3, Axl and Mer: Zhang et al., *J. Med. Chem.*, 2014, 57, 7031-7041; Rho et al., *Cancer Res.*, 2014, 74, 253-262; Traoré et al., *Euro. J. Med. Chem.*, 2013, 70, 789-801; Zhang et al., *J. Med. Chem.*, 2013, 56, 9683-9692; Zhang et al., *J. Med. Chem.*, 2013, 56, 9693-9700; Liu et al. *Euro. J. Med. Chem.*, 2013, 65, 83-93; Powell et al. *Bioorg. Med. Chem. Lett.*, 2013, 23, 1051-1055; Powell et al. *Bioorg. Med. Chem. Lett.*, 2013, 23, 1046-1050; Suárez et al. *Euro. J. Med. Chem.*, 2013, 61, 2-25; M. F. Burbridge et al. *Mol. Cancer Ther.*, 2013, 12, 1749-1762; Powell et al. *Bioorg. Med. Chem. Lett.* 2012, 22, 190-193; Liu et al. *ACS Med. Chem. Lett.*, 2012, 3, 129-134; Mollard et al. *ACS Med. Chem. Lett.*, 2011, 2, 907-912; Holland et al. *Cancer Res.*, 2010, 70(4), 1544-1554.; Ono et al. poster number MEDI-393, 244$^{th}$ ACS National Meeting & Exposition, Philadelphia, Pa., Aug. 19-23, 2012; Zhang et al. poster number MEDI-56, 244$^{th}$ ACS National Meeting & Exposition, Philadelphia, Pa., Aug. 19-23, 2012; Yang et al. poster number MEDI-265, 242$^{nd}$ ACS National Meeting & Exposition, Denver, Colo., Aug. 28-Sep. 1, 2011; Zhang et al. poster number MEDI-62, 242$^{nd}$ ACS National Meeting & Exposition, Denver, Colo., Aug. 28-Sep. 1, 2011; Wang et al.

poster number MEDI-18, 242$^{nd}$ ACS National Meeting & Exposition, Denver, Colo., Aug. 28-Sep. 1, 2011; Huang et al. *J. Stru. Biol.* 2009, 165, 88-96. Axl inhibitors have also been disclosed in US2008188455A1; WO2007030680A2; WO2008045978A1; WO2008080134A2; WO2008083353A1; WO2008083354A1; WO2008083356A1; WO2008083357A1; WO2008083367A2; WO2008128072A2; WO2009007390A2; WO2009024825A1; WO2009047514A1; WO2009053737A2; WO2009054864A1; WO2009127417A1; WO2010005876A2; WO2010005879A1; WO2010083465A1; WO2010090764A1; WO2011045084A1; WO2011138751A2; WO2012028332A1; WO2012135800A1; WO2013074633A1; WO2013115280A1 and WO2013162061A1.

Quinalzolines have been reported in the following literature reports: Besson et. al. *Tetrahedron*, 1998, 54, 6475-6484; Jin et. al. *Bioorg. Med. Chem.* 2005, 13, 5613-5622; Jung et. al. *J. Med. Chem.* 2006, 49, 955-970; Hennequin et. al. *J. Med. Chem.* 2006, 49, 6465-6488; Fray et. al. *Tetrahedron Lett.* 2006, 47, 6365-6368; Jin et. al. *Bioorg. Med. Chem. Lett.* 2006, 16, 5864-5869; Yang et al. *Bioorg. Med. Chem. Lett.* 2007, 17, 2193-2196; Duncton et al. *J. Org. Chem.*, 2009, 74, 6354-6357; Guiles et al. *Bioorg. Med. Chem. Lett.* 2009, 19, 800-802; Zhang et al. *Clin. Cancer Res.* 2011, 17, 4439-50; Li et al. *J. Med. Chem.*, 2012, 55, 3852-3866; Plé et al. *Bioorg. Med. Chem. Lett.* 2012, 22, 262-266; WO2000021955A1; WO2001094341A1; WO2003040109A2; WO2003045395A1; WO2003055491A1; WO2003055866A1; US20040038992A1; WO2004094401A1; WO2006040526A1; WO2006067391A1; WO2006129064A1; WO2007083096A2; WO2007117161A1; WO2009117080A1; WO2010136475A1; CN101747329A; and CN102382065A.

SUMMARY

In various aspects, the present disclosure provides quinazoline compounds that are capable of inhibiting the activity of one or more TAM family kinases. Methods of using such compounds to inhibit the activity of a TAM family kinase(s) and pharmaceutical compositions comprising such compounds are also provided.

In one aspect, the present disclosure provides quinazoline compounds of formula (I):

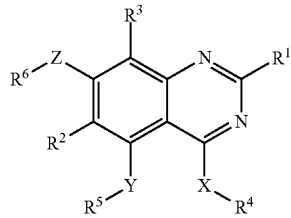

(I)

wherein:
X is selected from —C($R^9$)$_2$—, —N($R^{10}$)—, —O—, and —S(O)$_t$— where t is 0, 1, or 2;
Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^4$ is selected from alkyl, aralkyl, alkenyl, aralkenyl, alkynyl, aralkynyl, cycloalkyl, cycloalkylalkyl and haloalkyl; or $R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, or a prodrug thereof.

In another aspect, the invention provides quinazoline compounds of formula (II):

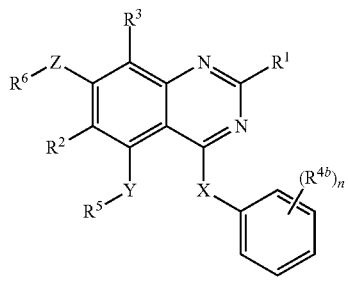

(II)

wherein:
X is selected from —C($R^9$)$_2$—, —O—, and —S(O)$_t$— where t is 0, 1, or 2;
Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^{4b}$ is independently selected from alkyl, cycloalkyl, cycloalkylalkyl, haloalkyl, halo, cyano, amino, alkoxy, hydroxyl and Q-L-$R^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;

n is 0, 1, 2, 3, 4, or 5;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

The present disclosure also provides pharmaceutical compositions containing at least one quinazoline compound as disclosed herein, i.e., a quniazoline compound within the scope of formulae (I) or (II), including subsets of those formulae.

In addition, the present disclosure is directed to a method for preventing, treating or ameliorating a disease, syndrome, condition or disorder that is affected by the inhibition of one or more members of the TMA family of kinases. The method comprises, consists of, and/or consists essentially of administering to a subject in need thereof, a therapeutically effective amount of a quinazoline compound as disclosed herein, i.e., a quinazoline compound with the scope of formula (I) or (II), including subsets of those formulae.

The details of one or more aspects and embodiments are set forth in the description below. Other features, objects and advantages will be apparent from the description and the claims. In addition, the disclosures of all patents and patent applications referenced herein are incorporated by reference in their entirety.

DETAILED DESCRIPTION OF THE INVENTION

Definitions

The following terms are provided solely to aid in the understanding of the invention. Unless defined otherwise, all technical and scientific terms used herein have the same meanings as commonly understood by one skilled in the art to which the disclosed invention belongs. The terms "a" and "the" as used herein are understood to encompass the plural as well as the singular. "Comprising" (and its grammatical variations) as used herein is used in the inclusive sense of "having" or "including" and not in the exclusive sense of "consisting only of." The terms "subject", "patient", "mammal" and "recipient" may be used herein interchangeably. Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Alkenyl" refers to a straight or branched hydrocarbon chain radical group consisting solely of carbon and hydrogen atoms, containing at least one double bond, having from two to twelve carbon atoms, or two to eight carbon atoms, or two to six carbon atoms, and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more (in various options, and independently at each occurrence in the compound, one, or two, or three) of the following groups: alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{14}$, —OC(O)R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, or from two to eight carbon atoms, or from two to six carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkoxy" refers to a radical of the formula —OR$_X$ where R$_X$ is an alkyl radical as defined above. The alkyl part of the alkoxy radical may be optionally substituted as defined above for an alkyl radical.

"Alkoxyalkyl" refers to a radical of the formula —R$_X$—O—R$_X$ where each R$_X$ is independently an alkyl radical as defined above. The oxygen atom may be bonded to any carbon in either alkyl radical. Each alkyl part of the alkoxyalkyl radical may be optionally substituted as defined above for an alkyl group.

"Alkyl" refers to a straight or branched hydrocarbon chain radical consisting solely of carbon and hydrogen atoms, containing no unsaturation, having from one to twelve carbon atoms, one to eight carbon atoms, or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, an alkyl group may be optionally substituted by one or more (in various options, and independently at each occurrence in the compound, one, or two, or three) of the following groups: alkyl, alkenyl, amino, halo, haloalkenyl, cyano, nitro, aryl, cycloalkyl, heterocyclyl, heteroaryl, —OR$^{14}$, —OC(O)R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkylaminoalkyl" refers to a radical of the formula —R$_X$—N(R$^{14}$)—R$_X$ where each R$_X$ is independently an alkyl radical as defined above. The nitrogen atom may be bonded to any carbon in either alkyl radical. Each alkyl part of the alkylaminoalkyl radical may be optionally substituted as defined above for an alkyl group. R$^{14}$ is hydrogen, alkyl, haloalkyl, cycloalkyl, cycloalkylalkyl, aryl, aralkyl, heterocyclyl, heterocyclylalkyl, heteroaryl or heteroarylalkyl.

"Alkylsulfonyl" refers to a radical of the formula —S(O)$_2$R$_X$ where R$_X$ is an alkyl group as defined above. The alkyl part of the alkylsulfonyl radical may be optionally substituted as defined above for an alkyl group.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, or one to eight carbons, or one to six carbon atoms, e.g., methylene, ethylene, propylene, n-butylene, and the like. The alkylene chain may be attached to the rest of the molecule and to the radical group through one carbon within the chain or through any two carbons within the chain.

"Alkylene bridge" refers to a straight or branched divalent hydrocarbon bridge, linking two different carbons of the same ring structure, consisting solely of carbon and hydrogen, containing no unsaturation and having from one to twelve carbon atoms, or from one to eight carbons, or from one to six carbon atoms, e.g., methylene, ethylene, propylene, n-butylene, and the like. The alkylene bridge may link any two carbons within the ring structure.

"Alkynyl" refers to a straight or branched hydrocarbon chain radical group consisting solely of carbon and hydrogen atoms, containing at least one triple bond, optionally containing at least one double bond, having from two to twelve carbon atoms, or one to eight carbon atoms, or one to six carbon atoms, and which is attached to the rest of the molecule by a single bond, for example, ethynyl, propynyl, butynyl, pentynyl, hexynyl, and the like. Unless stated otherwise specifically in the specification, an alkynyl group may be optionally substituted by one or more (in various options, and independently at each occurrence in the compound, one, or two, or three) of the following substituents: alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{14}$, —OC(O)R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)(S(O)$_t$R$^{16}$) (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise stated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, or two to eight carbon atoms, or two to six carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Amino" refers to the —NH$_2$ radical.

"Aralkyloxy" refers to a radical of the formula —OR$_X$ where R$_X$ is an aralkyl group as defined above. The aralkyl part of the aralkyloxy radical may be optionally substituted as defined above.

"Aralkyl" refers to a radical of the formula —R$_X$R$_Y$ where R$_X$ is an alkyl radical as defined above and R$_Y$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Aralkenyl" refers to a radical of the formula —R$_X$R$_Y$ where R$_X$ is an alkenyl radical as defined above and R$_Y$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula —R$_X$R$_Y$ where R$_X$ is an alkynyl radical as defined above and R$_Y$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryl" refers to aromatic monocyclic or multicyclic hydrocarbon ring system consisting only of hydrogen and carbon and containing from 6 to 19 carbon atoms, preferably 6 to 10 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more (in various options, and independently at each occurrence in the compound, one, or two, or three) substituents selected from the group consisting of alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise stated.

"Aryloxy" refers to a radical of the formula $-OR_X$ where $R_X$ is an aryl group as defined above. The aryl part of the aryloxy radical may be optionally substituted as defined above.

"Cyano" refers to the —CN radical.

"Cycloalkyl" refers to a non-aromatic monocyclic or bicyclic hydrocarbon radical consisting solely of carbon and hydrogen atoms, having from three to fifteen carbon atoms, having from three to twelve carbon atoms, or having three to six carbon atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more (in various options, and independently at each occurrence in the compound, one, or two, or three) substituents selected from the group consisting of alkyl, alkenyl, amino, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}N(R^{14})C(O)R^{16}$, $-R^{15}-N(R^{14})(S(O)_tR^{16})$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise stated.

"Cycloalkylalkenyl" refers to a radical of the formula $-R_XR_Y$ where $R_X$ is an alkenyl radical as defined above and $R_Y$ is a cycloalkyl radical as defined above. Either or both of the alkenyl radical and the cycloalkyl radical may be optionally substituted as defined above.

"Cycloalkylalkyl" refers to a radical of the formula $-R_XR_Y$ where $R_X$ is an alkyl radical as defined above and $R_Y$ is a cycloalkyl radical as defined above. The cycloalkyl part of the cycloalkyl radical may be optionally substituted as defined above for a cycloalkyl radical. The alkyl part of the cycloalkyl radical may be optionally substituted as defined above for an alkyl radical.

"Cycloalkylalkynyl" refers to a radical of the formula $-R_XR_Y$ where $R_X$ is an alkynyl radical as defined above and $R_Y$ is a cycloalkyl radical as defined above. Either or both of the alkynyl radical and the cycloalkyl radical may be optionally substituted as defined above.

"Disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Halo" refers to bromo, chloro, fluoro and/or iodo.

"Haloalkenyl" refers to an alkenyl radical as defined above that is substituted by one or more halo radicals, as defined above, e.g., 2-bromoethenyl, 3-bromoprop-1-enyl, and the like. The alkenyl part of the haloalkenyl radical may further be optionally substituted as defined above for an alkyl group.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoro-propyl, 1-bromomethyl-2-bromoethyl, and the like. The alkyl part of the haloalkyl radical may further be optionally substituted as defined above for an alkyl group.

"Haloalkynyl" refers to an alkynyl radical as defined above that is substituted by one or more halo radicals, as defined above. The alkynyl part of the haloalkyl radical may be optionally substituted as defined above for an alkynyl group.

"Heteroaryl" refers to a 5- to 18-membered aromatic ring radical which consists of carbon atoms and from one to five heteroatoms selected from the group consisting of nitrogen, oxygen and sulfur. Optionally, the heteroaryl may be a 5- to 12-membered ring, or a 5- to 8-membered ring, or 5-membered ring, or a 6-membered ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more (in various options, and independently at each occurrence in the compound, one, or two, or three) substituents selected from the group consisting of alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise stated.

"Heteroarylalkenyl" refers to a radical of the formula —$R_X R_Y$ where $R_X$ is an alkenyl radical as defined above and $R_Y$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroarylalkyl" refers to a radical of the formula —$R_X R_Y$ where $R_X$ is an alkyl radical as defined above and $R_Y$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkynyl" refers to a radical of the formula —$R_X R_Y$ where $R_X$ is an alkynyl radical as defined above and $R_Y$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Heteroarylcycloalkyl" refers to a radical of the formula —$R_X R_Y$ where $R_X$ is a cycloalkyl radical as defined above and $R_Y$ is a heteroaryl radical as defined above. The cycloalkyl part of the heteroarylcycloalkyl radical may be optionally substituted as defined above for a cycloalkyl group. The heteroaryl part of the heteroarylcycloalkyl radical may be optionally substituted as defined above for a heteroaryl group.

"Heterocyclyl" refers to a 3- to 18-membered non-aromatic ring radical which consists of carbon atoms and from one to five heteroatoms selected from the group consisting of nitrogen, oxygen and sulfur. Optionally, the heteroyclyl may be a 3- to 12-membered ring, or a 3- to 8-membered ring, or a 5-membered ring, or a 6-membered ring. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more (in various options, and independently at each occurrence in the compound, one, or two, or three) substituents selected from the group consisting of alkyl, alkenyl, amino, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—O$R^{14}$, —$R^{15}$—OC(O)—$R^{14}$, —$R^{15}$—N($R^{14}$)$_2$, —$R^{15}$—C(O)$R^{14}$, —$R^{15}$—C(O)O$R^{14}$, —$R^{15}$—C(O)N($R^{14}$)$_2$, —$R^{15}$—N($R^{14}$)C(O)O$R^{16}$, —$R^{15}$—N($R^{14}$)C(O)$R^{16}$, —$R^{15}$—N($R^{14}$)(S(O)$_t$$R^{16}$) (where t is 1 to 2), —$R^{15}$—S(O)$_t$O$R^{16}$ (where t is 1 to 2), —$R^{15}$—S(O)$_t$$R^{16}$ (where t is 0 to 2), and —$R^{15}$—S(O)$_t$N($R^{14}$)$_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise stated.

"Heterocyclylalkyl" refers to a radical of the formula —$R_X R_Y$ where $R_X$ is an alkyl radical as defined above and $R_Y$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Hydroxyalkenyl" refers to a radical of the formula —$R_X$—OH where $R_X$ is an alkenyl radical as defined above. The hydroxy group may be attached to the alkenyl radical on any carbon within the alkenyl radical. The alkenyl part of the hydroxyalkenyl group may be optionally substituted as defined above for an alkenyl group.

"Hydroxyalkyl" refers to a radical of the formula —$R_X$—OH where $R_X$ is an alkyl radical as defined above. The hydroxy group may be attached to the alkyl radical on any carbon within the alkyl radical. The alkyl part of the hydroxyalkyl group may be optionally substituted as defined above for an alkyl group.

"Hydroxyalkynyl" refers to a radical of the formula —$R_X$—OH where $R_X$ is an alkynyl radical as defined above. The hydroxy group may be attached to the alkynyl radical on any carbon within the alkynyl radical. The alkynyl part of the hydroxyalkynyl group may be optionally substituted as defined above for an alkynyl group.

"Isotopically enriched derivative" refers to a compound wherein one or more atoms are replaced by atoms having the same atomic number but an atomic mass or mass number different from the atomic mass or mass number usually found in nature. Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{38}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{31}$P, $^{32}$P and $^{33}$P, and sulphur, such as $^{35}$S. Substitution with heavier isotopes such as deuterium, i.e. $^2$H, may afford certain therapeutic advantages resulting from greater metabolic stability, for example, increased in vivo half-life or reduced dosage requirements and hence may be preferred in some circumstances. Isotopically-enriched compounds of the invention can generally be prepared by conventional techniques known to those skilled in the art or by processes analogous to those described in the accompanying Examples and Preparations Sections using an appropriate isotopically-enriched reagent in place of the non-enriched reagent previously employed.

"Mammal" includes humans and domestic animals, such as cats, dogs, swine, cattle, sheep, goats, horses, rabbits, and the like.

"Methoxy" refers to the —OCH$_3$ radical.

"Multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to one another through direct bonds or some or all of the rings may be fused to each other. Examples include, but are not limited to a cycloalkyl radical substituted by an aryl group; a cycloalkyl group substituted by an aryl group, which, in turn, is substituted by another aryl group; and so forth.

"Nitro" refers to the —NO$_2$ radical.

"Optional" or "optionally" means that the subsequently described event or circumstances may or may not occur, and that the description includes instances where said event or circumstance occurs and instances in which it does not. The disclosure provides for the situation where the optional event occurs. In addition, the disclosure provides for the case where the optional event does not occur. For example, "optionally substituted aryl" means that the aryl radical may or may not be substituted and that the description includes both substituted aryl radicals and aryl radicals having no substitution.

"Oxo" refers to the =O substituent.

"Pharmaceutical composition" refers to a formulation of a quinazoline compound as disclosed herein and a medium generally accepted in the art for the delivery of biologically active compound to mammals, e.g., humans. Such a medium includes all pharmaceutically acceptable carriers, diluents or excipients therefor.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, or organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., "Design of Prodrugs" (1985), pp. 7-9, 21-24, Elsevier, Amsterdam). The term "prodrug" includes any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like. A discussion of prodrugs is provided in Higuchi, T., et al., "Pro-drugs as Novel Delivery Systems," A.C.S. Symposium Series, Vol. 14 (1987), and in "Bioreversible Carriers in Drug Design", ed. Edward B. Roche, American Pharmaceutical Association and Pergamon Press, 1987, both of which are incorporated in full by reference herein.

"Radical" and "Group" are used herein interchangeably. A radical or group is a stable arrangement of atoms.

"Solvate" refers to an aggregate that comprises one or more molecules of a compound of the invention with one or more molecules of solvent. Often crystallizations produce a solvate of the compound of the invention. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Stable compound" and "stable structure" are meant to indicate a compound that is sufficiently robust to survive isolation to a useful degree of purity from a reaction mixture, and formulation into an efficacious therapeutic agent. Likewise, a "stable arrangement of atoms" is meant to indicate an atomic arrangement that is sufficiently robust to survive isolation to a useful degree of purity from a reaction mixture, and formulation into an efficacious therapeutic agent.

"Stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

"Tautomer" refers to a proton shift from one atom of a molecule to another atom of the same molecule. The present invention includes tautomers of the quinazoline compounds disclosed herein.

"Therapeutically effective amount" refers to that amount of a compound of the invention which, when administered to a mammal, preferably a human, is sufficient to effect treatment, as defined below, of a disease or condition in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Thioxo" refers to the =S substituent.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

"Trifluoromethyl" refers to the —CF$_3$ radical.

"Trihaloalkoxy" refers to a radical of the formula —OR$_X$ where R$_X$ is a trihaloalkyl group as defined above. The trihaloalkyl part of the trihaloalkoxy group may be optionally substituted as defined above for a trihaloalkyl group.

"Trihaloalkyl" refers to an alkyl radical as defined above that is substituted by three halo radicals, as defined above, e.g., trifluoromethyl which is a preferred trihaloalkyl. The alkyl part of the trihaloalkyl radical may further be optionally substituted as defined above for an alkyl group.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

The chemical naming protocol and structure diagrams used herein employ and rely on the chemical naming features as utilized by Chemdraw version 12.0.2.1076 (available from Cambridgesoft Corp., Cambridge, Mass.). For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms which are assumed to be bonded to sufficient hydrogen atoms to complete the valency. For example, a compound of formula (I), as set forth above in the Summary of the Invention, where X is —N(R$^{10}$)—, Y and Z are —O—, —R$^1$, —R$^2$ and —R$^3$ are hydrogen, —R$^4$ is 4-(trifluoromethyl)thiazol-2-yl, —R$^5$ is tetrahydro-2H-pyran-4-yl, —R$^6$ is (1-methylpiperidin-4-yl)methyl, and —R$^{10}$ is hydrogen, i.e., a compound of the following formula:

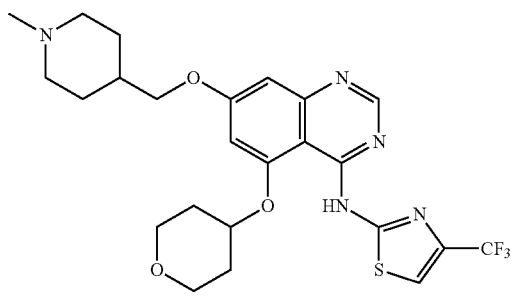

is named herein as N-(7-((1-methylpiperidin-4-yl)methoxy)-5-((tetrahydro-2H-pyran-4-yl)oxy)quinazolin-4-yl)-4-(trifluoromethyl)thiazol-2-amine.

Embodiments of the Invention

In one aspect, the present disclosure provides quinazoline compounds of formula (I):

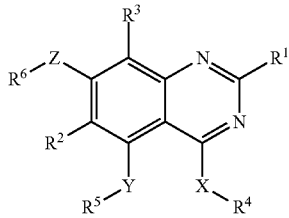

(I)

wherein:

X is selected from —C(R$^9$)$_2$—, —N(R$^{10}$)—, —O—, and —S(O)$_t$— where t is 0, 1, or 2;

Y and Z are independently selected from —C(R$^9$)$_2$—, —N(R$^{10}$)—, —O—, —S(O)$_t$— where t is 0, 1, or 2, and a heterocyclic moiety which contains 1 to 3 heteroatoms independently selected from O, N and S;

R$^1$ is selected from hydrogen, alkyl, cycloalkyl, cycloalkylalkyl, haloalkyl, aryl, heterocyclyl, heteroaryl, cyano, amino, alkoxy, and hydroxyl;

R$^2$ and R$^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

R$^4$ is selected from alkyl, aralkyl, alkenyl, aralkenyl, alkynyl, aralkynyl, cycloalkyl, cycloalkylalkyl and haloalkyl; or R$^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-R$^{4a}$, where R$^4$ is not pyrazole;

Q is a direct bond, or a straight or branched alkylene chain;

L is selected from —N(R$^{10}$)—, —O—, —C(O)—, —C(O)O—, —S(O)$_t$— where t is 0, 1, or 2, —CON(R$^{10}$)—, —N(R$^{10}$)CO—, —SO$_2$N(R$^{10}$)—, —N(R$^{10}$)SO$_2$—, and —N(R$^{10}$)CON(R$^{10}$)—;

R$^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

R$^5$ and R$^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —R$^7$—V—R$^8$ where V is selected from —N(R$^{10}$)—, or —O—;

R$^7$ is a straight or branched alkylene chain;

R$^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

R$^9$ is selected from hydrogen, alkyl, halo, and haloalkyl;

R$^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, or a prodrug thereof.

In another aspect, the invention provides quinazoline compounds of formula (II):

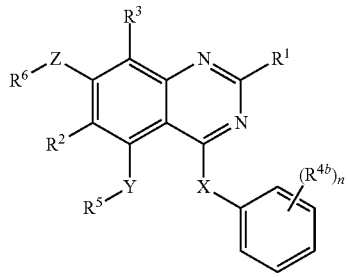

(II)

wherein:

X is selected from —C(R$^9$)$_2$—, —O—, and —S(O)$_t$— where t is 0, 1, or 2;

Y and Z are independently selected from —C(R$^9$)$_2$—, —N(R$^{10}$)—, —O—, —S(O)$_t$— where t is 0, 1, or 2, and a heterocyclic moiety which contains 1 to 3 heteroatoms independently selected from O, N and S;

R$^1$ is selected from hydrogen, alkyl, cycloalkyl, cycloalkylalkyl, haloalkyl, aryl, heterocyclyl, heteroaryl, cyano, amino, alkoxy, and hydroxyl;

R$^2$ and R$^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

R$^{4b}$ is independently selected from alkyl, cycloalkyl, cycloalkylalkyl, haloalkyl, halo, cyano, amino, alkoxy, hydroxyl and Q-L-R$^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;

n is 0, 1, 2, 3, 4, or 5;

Q is a direct bond, or a straight or branched alkylene chain;

L is selected from —N(R$^{10}$)—, —O—, —C(O)—, —C(O)O—, —S(O)$_t$— where t is 0, 1, or 2, —CON(R$^{10}$)—, —N(R$^{10}$)CO—, —SO$_2$N(R$^{10}$)—, —N(R$^{10}$)SO$_2$—, and —N(R$^{10}$)CON(R$^{10}$)—;

R$^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

R$^5$ and R$^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —R$^7$—V—R$^8$ where V is selected from —N(R$^{10}$)—, or —O—;

R$^7$ is a straight or branched alkylene chain;

R$^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

R$^9$ is selected from hydrogen, alkyl, halo, and haloalkyl;

R$^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

In regard to each of formulae (I) and (II), the present disclosure provides subsets of compounds within the scope of formulae (I) and (II). For example, in regard to compounds of formula (I), the present disclosure provides for the following specific embodiments, any one or two or three or four or five or six or more of the embodiments may be combined in order to describe a subset of the compounds of the present disclosure. For example, any one or more of the following alternative options for X may optionally be combined with any one or more of the following alternative options for Y, which may optionally be combined with any one or more of the following alternative options for Z, etc. In various embodiments, X is —C($R^9$)$_2$—, or X is —N($R^{10}$)—, or X is —O—, or X is —S(O)$_t$— where t is 0, 1, or 2. In various embodiments, Y is —C($R^9$)$_2$—, or Y is —N($R^{10}$)—, or Y is —O—, or Y is —S(O)$_t$— where t is 0, 1, or 2, or Y is a heterocyclic moiety which contains 1 or 2 or 3 or 1 to 3 heteroatoms independently selected from O, N and S. In various embodiments, Z is —C($R^9$)$_2$—, or Z is —N($R^{10}$)—, or Z is —O—, or Z is —S(O)$_t$— where t is 0, 1, or 2, or Z is a heterocyclic moiety which contains 1 or 2 or 3 or 1 to 3 heteroatoms independently selected from O, N and S. In various embodiments, $R^1$ is hydrogen, or $R^1$ is alkyl, or $R^1$ is cycloalkyl, or $R^1$ is cycloalkylalkyl, or $R^1$ is haloalkyl, or $R^1$ is aryl, or $R^1$ is heterocyclyl, or $R^1$ is heteroaryl, or $R^1$ is cyano, or $R^1$ is amino, or $R^1$ is alkoxy, or $R^1$ is hydroxyl. In various embodiments, $R^2$ is hydrogen, or $R^2$ is alkyl, or $R^2$ is aralkyl, or $R^2$ is cycloalkyl, or $R^2$ is cycloalkylalkyl, or $R^2$ is haloalkyl, or $R^2$ is halo, or $R^2$ is heterocyclyl, or $R^2$ is heterocyclylalkyl, or $R^2$ is alkoxy, or $R^2$ is alkoxyalkyl. In various embodiments, $R^3$ is hydrogen, or $R^3$ is alkyl, or $R^3$ is aralkyl, or $R^3$ is cycloalkyl, or $R^3$ is cycloalkylalkyl, or $R^3$ is haloalkyl, or $R^3$ is halo, or $R^3$ is heterocyclyl, or $R^3$ is heterocyclylalkyl, or $R^3$ is alkoxy, or $R^3$ is alkoxyalkyl. In various embodiments, $R^4$ is alkyl, or $R^4$ is aralkyl, or $R^4$ is alkenyl, or $R^4$ is aralkenyl, or $R^4$ is alkynyl, or $R^4$ is aralkynyl, or $R^4$ is cycloalkyl, or $R^4$ is cycloalkylalkyl, or $R^4$ is haloalkyl, or $R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole. In various embodiments, Q is a direct bond, or Q is a straight alkylene chain, or Q is a branched alkylene chain. In various embodiments, L is —N($R^{10}$)—, or L is —O—, or L is —C(O)—, or L is —C(O)O—, or L is —S(O)$_t$— where t is 0, 1, or 2, or L is —CON($R^{10}$)—, or L is —N($R^{10}$)CO—, or L is —SO$_2$N($R^{10}$)—, or L is —N($R^{10}$)SO$_2$—, or L is —N($R^{10}$)CON($R^{10}$)—. In various embodiments, $R^{4a}$ is alkyl, or $R^{4a}$ is aralkyl, or $R^{4a}$ is alkenyl, or $R^{4a}$ is aralkenyl, or $R^{4a}$ is alkynyl, or $R^{4a}$ is aralkynyl, or $R^{4a}$ is cycloalkyl, or $R^{4a}$ is cycloalkylalkyl, or $R^{4a}$ is haloalkyl, or $R^{4a}$ is aryl, or $R^{4a}$ is heteroaryl, or $R^{4a}$ is heterocyclyl. In various embodiments, $R^5$ is hydrogen, or $R^5$ is alkyl, or $R^5$ is aralkyl, or $R^5$ is alkenyl, or $R^5$ is aralkenyl, or $R^5$ is alkynyl, or $R^5$ is aralkynyl, or $R^5$ is cycloalkyl, or $R^5$ is cycloalkylalkyl, or $R^5$ is heteroaryl, or $R^5$ is heteroaralkyl, or $R^5$ is heterocyclyl, or $R^5$ is heterocyclylalkyl, or $R^5$ is alkoxyalkyl, or $R^5$ is alkylaminoalkyl, or $R^5$ is —$R^7$—V—$R^8$ where V is —N($R^{10}$)—, or $R^5$ is —$R^7$—V—$R^8$ where V is —O—. In various embodiments, $R^6$ is hydrogen, or $R^6$ is alkyl, or $R^6$ is aralkyl, or $R^6$ is alkenyl, or $R^6$ is aralkenyl, or $R^6$ is alkynyl, or $R^6$ is aralkynyl, or $R^6$ is cycloalkyl, or $R^6$ is cycloalkylalkyl, or $R^6$ is heteroaryl, or $R^6$ is heteroaralkyl, or $R^6$ is heterocyclyl, or $R^6$ is heterocyclylalkyl, or $R^6$ is alkoxyalkyl, or $R^6$ is alkylaminoalkyl, or $R^6$ is —$R^7$—V—$R^8$ where V is —N($R^{10}$)—, or $R^6$ is —$R^7$—V—$R^8$ where V is —O—. In various embodiments, $R^7$ is a straight alkylene chain; or $R^7$ is a straight alkylene chain which is unsubstituted; or $R^7$ is a branched alkylene chain, or $R^7$ is a branched alkylene chain which is unsubstituted. In various embodiments, $R^8$ is hydrogen, or $R^8$ is alkyl, or $R^8$ is aralkyl, or $R^8$ is alkenyl, or $R^8$ is aralkenyl, or $R^8$ is alkynyl, or $R^8$ is aralkynyl, or $R^8$ is cycloalkyl, or $R^8$ is cycloalkylalkyl, or $R^8$ is heteroaryl, or $R^8$ is heteroaralkyl, or $R^8$ is heterocyclyl, or $R^8$ is heterocyclylalkyl, or $R^8$ is alkoxyalkyl, or $R^8$ is alkylaminoalkyl. In various embodiments, $R^9$ is hydrogen, or $R^9$ is alkyl, or $R^9$ is halo, or $R^9$ is haloalkyl. In various embodiments, $R^{10}$ is hydrogen, or $R^{10}$ is alkyl, or $R^{10}$ is cycloalkyl, or $R^{10}$ is cycloalkylalkyl, or $R^{10}$ is haloalkyl. In various embodiments, the compound of formula (I) is a specific stereoisomer, a specific enantiomer, a specific set of tautomers, an isotopically enriched compound, a pharmaceutically acceptable salt, a prodrug of a compound of formula (I).

In one aspect, the present disclosure provides quinazoline compounds of formula (II):

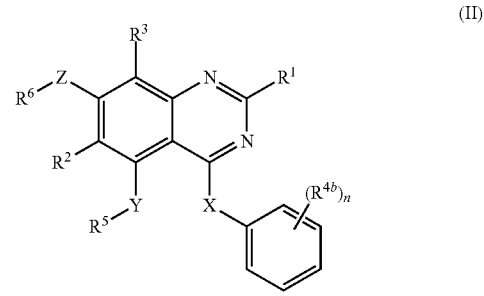

(II)

wherein:

X is selected from —C($R^9$)$_2$—, —O—, and —S(O)$_t$— where t is 0, 1, or 2;

Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^{4b}$ is independently selected from alkyl, cycloalkyl, cycloalkylalkyl, haloalkyl, halo, cyano, amino, alkoxy, hydroxyl and Q-L-$R^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;

n is 0, 1, 2, 3, 4, or 5;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —$N(R^{10})$—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

As mentioned previously, in regard to each of formulae (I) and (II), the present disclosure provides subsets of compounds within the scope of formulae (I) and (II). For example, in regard to compounds of formula (II), the present disclosure provides for the following specific embodiments, any one or two or three or four or five or six or more of the embodiments may be combined in order to describe a subset of the compounds of the present disclosure. For example, any one or more of the alternative options for X may optionally be combined with any one or more alternative options from Y, which may optionally be combined with any one or more alternative options for Z, etc. In various embodiments, X is —$C(R^9)_2$—, or X is —O—, or X is —$S(O)_t$— where t is 0, 1, or 2. In various embodiments, Y is —$C(R^9)_2$—, or Y is —$N(R^{10})$—, or Y is —O—, or Y is —$S(O)_t$— where t is 0, 1, or 2, or Y is a heterocyclic moiety which contains 1 or 2 or 3 or 1 to 3 heteroatoms independently selected from O, N and S. In various embodiments, Z is —$C(R^9)_2$—, or Z is —$N(R^{10})$—, or Z is —O—, or Z is —$S(O)_t$— where t is 0, 1, or 2, or Z is a heterocyclic moiety which contains 1 or 2 or 3 or 1 to 3 heteroatoms independently selected from O, N and S. In various embodiments, $R^1$ is hydrogen, or $R^1$ is alkyl, or $R^1$ is cycloalkyl, or $R^1$ is cycloalkylalkyl, or $R^1$ is haloalkyl, or $R^1$ is aryl, or $R^1$ is heterocyclyl, or $R^1$ is heteroaryl, or $R^1$ is cyano, or $R^1$ is amino, or $R^1$ is alkoxy, or $R^1$ is hydroxyl. In various embodiments, $R^2$ is hydrogen, or $R^2$ is alkyl, or $R^2$ is aralkyl, or $R^2$ is cycloalkyl, or $R^2$ is cycloalkylalkyl, or $R^2$ is haloalkyl, or $R^2$ is halo, or $R^2$ is heterocyclyl, or $R^2$ is heterocyclylalkyl, or $R^2$ is alkoxy, or $R^2$ is alkoxyalkyl. In various embodiments, $R^3$ is hydrogen, or $R^3$ is alkyl, or $R^3$ is aralkyl, or $R^3$ is cycloalkyl, or $R^3$ is cycloalkylalkyl, or $R^3$ is haloalkyl, or $R^3$ is halo, or $R^3$ is heterocyclyl, or $R^3$ is heterocyclylalkyl, or $R^3$ is alkoxy, or $R^3$ is alkoxyalkyl. In various embodiments, $R^{4b}$ is alkyl, or $R^{4b}$ is cycloalkyl, or $R^{4b}$ is cycloalkylalkyl, or $R^{4b}$ is haloalkyl, or $R^{4b}$ is halo, or $R^{4b}$ is cyano, or $R^{4b}$ is amino, or $R^{4b}$ is alkoxy, or $R^{4b}$ is hydroxyl or $R^{4b}$ is Q-L-$R^{4a}$; or $R^{4b}$ indicates that two substituent groups at adjacent carbon atoms together to form a ring structure wherein the ring structure may be unsaturated or saturated, may be non-aromatic or aromatic, and may contain 1 to 2 heteroatoms selected from N, O, and S. In various embodiments, n is 0, or n is 1, or n is 2, or n is 3, or n is 4, or n is 5. In various embodiments, Q is a direct bond, or Q is a straight alkylene chain, or Q is a branched alkylene chain. In various embodiments, L is —$N(R^{10})$—, or L is —O—, or L is —C(O)—, or L is —C(O)O—, or L is —$S(O)_t$— where t is 0, 1, or 2, or L is —$CON(R^{10})$—, or L is —$N(R^{10})CO$—, or L is —$SO_2N(R^{10})$—, or L is —$N(R^{10})SO_2$—, or L is —$N(R^{10})CON(R^{10})$—. In various embodiments, $R^{4a}$ is alkyl, or $R^{4a}$ is aralkyl, or $R^{4a}$ is alkenyl, or $R^{4a}$ is aralkenyl, or $R^{4a}$ is alkynyl, or $R^{4a}$ is aralkynyl, or $R^{4a}$ is cycloalkyl, or $R^{4a}$ is cycloalkylalkyl, or $R^{4a}$ is haloalkyl, or $R^{4a}$ is aryl, or $R^{4a}$ is heteroaryl, or $R^{4a}$ is heterocyclyl. In various embodiments, $R^5$ is hydrogen, or $R^5$ is alkyl, or $R^5$ is aralkyl, or $R^5$ is alkenyl, or $R^5$ is aralkenyl, or $R^5$ is alkynyl, or $R^5$ is aralkynyl, or $R^5$ is cycloalkyl, or $R^5$ is cycloalkylalkyl, or $R^5$ is heteroaryl, or $R^5$ is heteroaralkyl, or $R^5$ is heterocyclyl, or $R^5$ is heterocyclylalkyl, or $R^5$ is alkoxyalkyl, or $R^5$ is alkylaminoalkyl, or $R^5$ is —$R^7$—V—$R^8$ where V is —$N(R^{10})$—, or $R^5$ is —$R^7$—V—$R^8$ where V is —O—. In various embodiments, $R^6$ is hydrogen, or $R^6$ is alkyl, or $R^6$ is aralkyl, or $R^6$ is alkenyl, or $R^6$ is aralkenyl, or $R^6$ is alkynyl, or $R^6$ is aralkynyl, or $R^6$ is cycloalkyl, or $R^6$ is cycloalkylalkyl, or $R^6$ is heteroaryl, or $R^6$ is heteroaralkyl, or $R^6$ is heterocyclyl, or $R^6$ is heterocyclylalkyl, or $R^6$ is alkoxyalkyl, or $R^6$ is alkylaminoalkyl, or $R^6$ is —$R^7$—V—$R^8$ where V is —$N(R^{10})$—, or $R^6$ is —$R^7$—V—$R^8$ where V is —O—. In various embodiments, $R^7$ is a straight alkylene chain; or $R^7$ is a straight alkylene chain which is unsubstituted; or $R^7$ is a branched alkylene chain, or $R^7$ is a branched alkylene chain which is unsubstituted. In various embodiments, $R^8$ is hydrogen, or $R^8$ is alkyl, or $R^8$ is aralkyl, or $R^8$ is alkenyl, or $R^8$ is aralkenyl, or $R^8$ is alkynyl, or $R^8$ is aralkynyl, or $R^8$ is cycloalkyl, or $R^8$ is cycloalkylalkyl, or $R^8$ is heteroaryl, or $R^8$ is heteroaralkyl, or $R^8$ is heterocyclyl, or $R^8$ is heterocyclylalkyl, or $R^8$ is alkoxyalkyl, or $R^8$ is alkylaminoalkyl. In various embodiments, $R^9$ is hydrogen, or $R^9$ is alkyl, or $R^9$ is halo, or $R^9$ is haloalkyl. In various embodiments, $R^{10}$ is hydrogen, or $R^{10}$ is alkyl, or $R^{10}$ is cycloalkyl, or $R^{10}$ is cycloalkylalkyl, or $R^{10}$ is haloalkyl. In various embodiments, the compound of formula (I) is a specific stereoisomer, a specific enantiomer, a specific set of tautomers, an isotopically enriched compound, a pharmaceutically acceptable salt, a prodrug of a compound of formula (II).

As mentioned previously, the present disclosure provides quinazoline compounds having isotopic enrichment at one or more atoms. Isotopic enrichment is a process by which the relative abundance of the isotopes of a given element are altered, thus producing a form of the element that has been enriched in one particular isotope and depleted in its other isotopic forms. Isotopic enrichment of a drug are used for the following applications: reducing or eliminating unwanted metabolites; increasing the half-life of the parent drug; decreasing the number of doses needed to achieve a desired effect; decreasing the amount of a dose necessary to achieve a desired effect; increasing the formation of active metabolites, if any are formed; and/or decreasing the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect. For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect (Foster et. al., *Adv. Drug Res.*, 1985, 14, 1-36; Kushner et. al., *Can. J. Physiol. Pharmacol.*, 1999, 77, 79-88).

Improvement of metabolism, pharmacokinetics, pharmacodynamics, and toxicity profiles of pharmaceuticals by isotopic enrichment such as deuteration has been demonstrated by the following examples: Lijinsky et. al., *J. Nat. Cancer Inst.*, 1982, 69, 1127-1133; Gately et. al., *J. Nucl. Med.*, 1986, 27, 388-394; Gordon et. al., *Drug Metab.*

Dispos., 1987, 15, 589-594; Mangold et. al., *Mutation Res.*, 1994, 308, 33-42; Zello et. al., *Metabolism*, 1994, 43, 487-491; Wade D., *Chem. Biol. Interact.*, 1999, 117, 191-217.

Thus, the present disclosure provides the following numbered embodiments, which are exemplary of the embodiments provided herein:

1. A compound of formula (I):

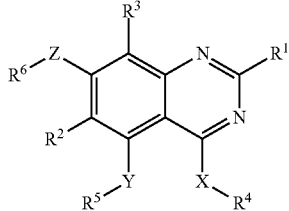

(I)

wherein:

X is selected from —C($R^9$)$_2$—, —N($R^{10}$)—, —O—, and —S(O)$_t$— where t is 0, 1, or 2;

Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^4$ is selected from alkyl, aralkyl, alkenyl, aralkenyl, alkynyl, aralkynyl, cycloalkyl, cycloalkylalkyl and haloalkyl; or $R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, or a prodrug thereof.

2. A compound of formula (II):

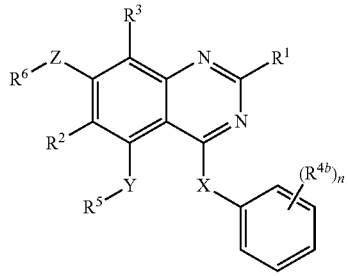

(II)

wherein:

X is selected from —C($R^9$)$_2$—, —O—, and —S(O)$_t$— where t is 0, 1, or 2;

Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^{4b}$ is independently selected from alkyl, cycloalkyl, cycloalkylalkyl, haloalkyl, halo, cyano, amino, alkoxy, hydroxyl and Q-L-$R^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;

n is 0, 1, 2, 3, 4, or 5;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

3. A compound of embodiments 1 or 2 wherein X is —C(R$^9$)$_2$—.

4. A compound of embodiment 1 wherein X is —N(R$^{10}$)—.

5. A compound of embodiments 1 or 2 wherein X is —O—.

6. A compound of embodiments 1 or 2 wherein X is —S(O)$_t$— where t is 0, 1, or 2.

7. A compound of embodiments 1 or 2 wherein Y is —C(R$^9$)$_2$—.

8. A compound of embodiments 1 or 2 wherein Y is —N(R$^{10}$)—.

9. A compound of embodiments 1 or 2 wherein Y is —O—.

10. A compound of embodiments 1 or 2 wherein Y is —S(O)$_t$— where t is 0, 1, or 2.

11. A compound of embodiments 1 or 2 wherein Y is a heterocyclic moiety which contains 1 to 3 heteroatoms independently selected from O, N and S.

12. A compound of embodiments 1 or 2 wherein Z is —C(R$^9$)$_2$—.

13. A compound of embodiments 1 or 2 wherein Z is —N(R$^{10}$)—.

14. A compound of embodiments 1 or 2 wherein Z is —O—.

15. A compound of embodiments 1 or 2 wherein Z is —S(O)$_t$— where t is 0, 1, or 2.

16. A compound of embodiments 1 or 2 wherein Z is a heterocyclic moiety which contains 1 to 3 heteroatoms independently selected from O, N and S.

17. A compound of embodiments 1 or 2 wherein R$^1$ is hydrogen.

18. A compound of embodiments 1 or 2 wherein R$^1$ is alkyl.

19. A compound of embodiments 1 or 2 wherein R$^1$ cycloalkyl.

20. A compound of embodiments 1 or 2 wherein R$^1$ is cycloalkylalkyl.

21. A compound of embodiments 1 or 2 wherein R$^1$ is haloalkyl.

22. A compound of embodiments 1 or 2 wherein R$^1$ is aryl.

23. A compound of embodiments 1 or 2 wherein R$^1$ is heterocyclyl.

24. A compound of embodiments 1 or 2 wherein R$^1$ is heteroaryl.

25. A compound of embodiments 1 or 2 wherein R$^1$ is cyano.

26. A compound of embodiments 1 or 2 wherein R$^1$ is amino.

27. A compound of embodiments 1 or 2 wherein R$^1$ is alkoxy.

28. A compound of embodiments 1 or 2 wherein R$^1$ is hydroxyl.

29. A compound of embodiments 1 or 2 wherein R$^2$ is hydrogen.

30. A compound of embodiments 1 or 2 wherein R$^2$ is alkyl.

31. A compound of embodiments 1 or 2 wherein R$^2$ is aralkyl.

32. A compound of embodiments 1 or 2 wherein R$^2$ is cycloalkyl.

33. A compound of embodiments 1 or 2 wherein R$^2$ is cycloalkylalkyl.

34. A compound of embodiments 1 or 2 wherein R$^2$ is haloalkyl.

35. A compound of embodiments 1 or 2 wherein R$^2$ is halo.

36. A compound of embodiments 1 or 2 wherein R$^2$ is heterocyclyl.

37. A compound of embodiments 1 or 2 wherein R$^2$ is heterocyclylalkyl.

38. A compound of embodiments 1 or 2 wherein R$^2$ is alkoxy.

39. A compound of embodiments 1 or 2 wherein R$^2$ is alkoxyalkyl.

40. A compound of embodiments 1 or 2 wherein R$^3$ is hydrogen.

41. A compound of embodiments 1 or 2 wherein R$^3$ is alkyl.

42. A compound of embodiments 1 or 2 wherein R$^3$ is aralkyl.

43. A compound of embodiments 1 or 2 wherein R$^3$ is cycloalkyl.

44. A compound of embodiments 1 or 2 wherein R$^3$ is cycloalkylalkyl.

45. A compound of embodiments 1 or 2 wherein R$^3$ is haloalkyl.

46. A compound of embodiments 1 or 2 wherein R$^3$ is halo.

47. A compound of embodiments 1 or 2 wherein R$^3$ is heterocyclyl.

48. A compound of embodiments 1 or 2 wherein R$^3$ is heterocyclylalkyl.

49. A compound of embodiments 1 or 2 wherein R$^3$ is alkoxy.

50. A compound of embodiments 1 or 2 wherein R$^3$ is alkoxyalkyl.

51. A compound of embodiment 1 wherein R$^4$ is alkyl.

52. A compound of embodiment 1 wherein R$^4$ is aralkyl.

53. A compound of embodiment 1 wherein R$^4$ is alkenyl.

54. A compound of embodiment 1 wherein R$^4$ is aralkenyl.

55. A compound of embodiment 1 wherein R$^4$ is alkynyl.

56. A compound of embodiment 1 wherein R$^4$ is aralkynyl.

57. A compound of embodiment 1 wherein R$^4$ is cycloalkyl.

58. A compound of embodiment 1 wherein R$^4$ is cycloalkylalkyl.

59. A compound of embodiment 1 wherein R$^4$ is haloalkyl.

60. A compound of embodiment 1 wherein R$^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-R$^{4a}$, where R$^4$ is not pyrazole.

61. A compound of embodiment 2 wherein R$^{4b}$ is alkyl.

62. A compound of embodiment 2 wherein R$^{4b}$ is cycloalkyl.

63. A compound of embodiment 2 wherein R$^{4b}$ is cycloalkylalkyl.

64. A compound of embodiment 2 wherein R$^{4b}$ is haloalkyl.

65. A compound of embodiment 2 wherein R$^{4b}$ is halo.

66. A compound of embodiment 2 wherein R$^{4b}$ is cyano.

67. A compound of embodiment 2 wherein R$^{4b}$ is amino.

68. A compound of embodiment 2 wherein R$^{4b}$ is alkoxy.

69. A compound of embodiment 2 wherein $R^{4b}$ is hydroxyl.

70. A compound of embodiment 2 wherein $R^{4b}$ is Q-L-$R^{4a}$.

71. A compound of embodiment 2 wherein $R^{4b}$ is two substituent groups at adjacent carbon atoms together which form a ring structure wherein the ring structure may be unsaturated or saturated, may be non-aromatic or aromatic, and may contain 1 to 2 heteroatoms selected from N, O, and S.

72. A compound of embodiment 2 wherein n is 0.

73. A compound of embodiment 2 wherein n is 1.

74. A compound of embodiment 2 wherein n is 2.

75. A compound of embodiments 1 or 2 wherein Q is a direct bond.

76. A compound of embodiments 1 or 2 wherein Q is a straight or branched alkylene chain.

77. A compound of embodiments 1 or 2 wherein L is —N($R^{10}$)—.

78. A compound of embodiments 1 or 2 wherein L is —O—.

79. A compound of embodiments 1 or 2 wherein L is —C(O)—.

80. A compound of embodiments 1 or 2 wherein L is —C(O)O—.

81. A compound of embodiments 1 or 2 wherein L is —S(O)$_t$— where t is 0, 1, or 2.

82. A compound of embodiments 1 or 2 wherein L is —CON($R^{10}$)—.

83. A compound of embodiments 1 or 2 wherein L is —N($R^{10}$)CO—.

84. A compound of embodiments 1 or 2 wherein L is —SO$_2$N($R^{10}$)—.

85. A compound of embodiments 1 or 2 wherein L is —N($R^{10}$)SO$_2$—.

86. A compound of embodiments 1 or 2 wherein L is —N($R^{10}$)CON($R^{10}$)—.

87. A compound of embodiments 1 or 2 wherein $R^{4a}$ is alkyl.

88. A compound of embodiments 1 or 2 wherein $R^{4a}$ is aralkyl.

89. A compound of embodiments 1 or 2 wherein $R^{4a}$ is alkenyl.

90. A compound of embodiments 1 or 2 wherein $R^{4a}$ is aralkenyl.

91. A compound of embodiments 1 or 2 wherein $R^{4a}$ is alkynyl.

92. A compound of embodiments 1 or 2 wherein $R^{4a}$ is aralkynyl.

93. A compound of embodiments 1 or 2 wherein $R^{4a}$ is cycloalkyl.

94. A compound of embodiments 1 or 2 wherein $R^{4a}$ is cycloalkylalkyl.

95. A compound of embodiments 1 or 2 wherein $R^{4a}$ is haloalkyl.

96. A compound of embodiments 1 or 2 wherein $R^{4a}$ is aryl.

97. A compound of embodiments 1 or 2 wherein $R^{4a}$ is heteroaryl.

98. A compound of embodiments 1 or 2 wherein $R^{4a}$ is heterocyclyl.

99. A compound of embodiments 1 or 2 wherein $R^5$ is hydrogen.

100. A compound of embodiments 1 or 2 wherein $R^5$ is alkyl.

101. A compound of embodiments 1 or 2 wherein $R^5$ is aralkyl.

102. A compound of embodiments 1 or 2 wherein $R^5$ is alkenyl.

103. A compound of embodiments 1 or 2 wherein $R^5$ is aralkenyl.

104. A compound of embodiments 1 or 2 wherein $R^5$ is alkynyl.

105. A compound of embodiments 1 or 2 wherein $R^5$ is aralkynyl.

106. A compound of embodiments 1 or 2 wherein $R^5$ is cycloalkyl.

107. A compound of embodiments 1 or 2 wherein $R^5$ is cycloalkylalkyl.

108. A compound of embodiments 1 or 2 wherein $R^5$ is heteroaryl.

109. A compound of embodiments 1 or 2 wherein $R^5$ is heteroaralkyl.

110. A compound of embodiments 1 or 2 wherein $R^5$ is heterocyclyl.

111. A compound of embodiments 1 or 2 wherein $R^5$ is heterocyclylalkyl.

112. A compound of embodiments 1 or 2 wherein $R^5$ is alkoxyalkyl.

113. A compound of embodiments 1 or 2 wherein $R^5$ is alkylaminoalkyl.

114. A compound of embodiments 1 or 2 wherein $R^5$ is —$R^7$—V—$R^8$ where V is —N($R^{10}$)—.

115. A compound of embodiments 1 or 2 wherein $R^5$ is —$R^7$—V—$R^8$ where V is —O—.

116. A compound of embodiments 1 or 2 wherein $R^8$ is hydrogen.

117. A compound of embodiments 1 or 2 wherein $R^8$ is alkyl.

118. A compound of embodiments 1 or 2 wherein $R^8$ is aralkyl.

119. A compound of embodiments 1 or 2 wherein $R^8$ is alkenyl.

120. A compound of embodiments 1 or 2 wherein $R^8$ is aralkenyl.

121. A compound of embodiments 1 or 2 wherein $R^8$ is alkynyl.

122. A compound of embodiments 1 or 2 wherein $R^8$ is aralkynyl.

123. A compound of embodiments 1 or 2 wherein $R^8$ is cycloalkyl.

124. A compound of embodiments 1 or 2 wherein $R^8$ is cycloalkylalkyl.

125. A compound of embodiments 1 or 2 wherein $R^8$ is heteroaryl.

126. A compound of embodiments 1 or 2 wherein $R^8$ is heteroaralkyl.

127. A compound of embodiments 1 or 2 wherein $R^8$ is heterocyclyl.

128. A compound of embodiments 1 or 2 wherein $R^8$ is heterocyclylalkyl.

129. A compound of embodiments 1 or 2 wherein $R^8$ is alkoxyalkyl.

130. A compound of embodiments 1 or 2 wherein $R^8$ is alkylaminoalkyl.

131. A compound of embodiments 1 or 2 wherein $R^9$ is hydrogen.

132. A compound of embodiments 1 or 2 wherein $R^9$ is alkyl.

133. A compound of embodiments 1 or 2 wherein $R^9$ is halo.

134. A compound of embodiments 1 or 2 wherein $R^9$ is haloalkyl.

135. A compound of embodiments 1 or 2 wherein $R^{10}$ is hydrogen.

136. A compound of embodiments 1 or 2 wherein $R^{10}$ is alkyl.

137. A compound of embodiments 1 or 2 wherein $R^{10}$ is cycloalkyl.

138. A compound of embodiments 1 or 2 wherein $R^{10}$ is cycloalkylalkyl.

139. A compound of embodiments 1 or 2 wherein $R^{10}$ is haloalkyl.

140. A compound of embodiments 1 or 2 wherein the compound is an isolated stereoisomer.

141. A compound of embodiments 1 or 2 wherein the compound is an isolated, enantiomer.

142. A compound of embodiments 1 or 2 wherein the compound is an isotopically enriched compound.

143. A compound of embodiments 1 or 2 wherein the compound is a pharmaceutically acceptable salt of a compound of formula (I) or (II).

144. A compound of embodiments 1 or 2 wherein the compound is a prodrug of a compound of formula (I) or (II).

For example, the present disclosure provides the numbered embodiments:

1) A compound of embodiment 1 wherein $R^1$ is hydrogen.
2) A compound of embodiments 1 and 1) wherein $R^2$ is hydrogen.
3) A compound of embodiments 1 and 1) wherein $R^2$ is alkoxy.
4) A compound of embodiments 1 and 1-3) wherein $R^3$ is hydrogen.
5) A compound of embodiments 1 and 1-4) wherein $R^4$ is selected from alkyl, aralkyl, alkenyl, aralkenyl, alkynyl, aralkynyl, cycloalkyl, cycloalkylalkyl and haloalkyl.
6) A compound of embodiments 1 and 1-4) wherein $R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole.
7) A compound of embodiments 1 and 1-6) wherein X is —O—.
8) A compound of embodiments 1 and 1-7) wherein Y is —O—.
9) A compound of embodiments 1 and 1-8) wherein $R^5$ is heterocyclyl.
10) A compound of embodiments 1 and 1-9) wherein $R^6$ is —$R^7$—V—$R^8$ where V is selected from —N($R^{10}$)—, or —O—.
11) A pharmaceutical composition comprising a compound of embodiments 1 and 1-10).
12) A method of treating or ameliorating a disease, syndrome, condition or disorder that is affected by modulating the activity of a TAM kinase, comprising administering to a subject in need thereof, a therapeutically effective amount of a compound of embodiments 1-10) or a composition of embodiment 11).

In addition, the present disclosure provides the numbered embodiments:

13) A compound of embodiment 2 wherein $R^1$ is hydrogen.
14) A compound of embodiments 2 and 13) wherein $R^2$ is hydrogen.
15) A compound of embodiments 2 and 13) wherein $R^2$ is alkoxy.
16) A compound of embodiments 2 and 13-15) wherein $R^3$ is hydrogen.
17) A compound of embodiments 2 and 13-16) wherein $R^{4b}$ is halo and n is 1 or 2 or 3 or 4 or 5.
18) A compound of embodiments 2 and 13-17) wherein n is zero.
19) A compound of embodiments 2 and 13-18) wherein X is —O—.
20) A compound of embodiments 2 and 13-19) wherein Y is —O—.
21) A compound of embodiments 2 and 13-20) wherein $R^5$ is heterocyclyl.
22) A compound of embodiments 2 and 13-21) wherein $R^6$ is —$R^7$—V—$R^8$ where V is selected from —N($R^{10}$)—, or —O—.
23) A pharmaceutical composition comprising a compound of embodiments 2 and 13-22).
24) A method of treating or ameliorating a disease, syndrome, condition or disorder that is affected by modulating the activity of a TAM kinase, comprising administering to a subject in need thereof, a therapeutically effective amount of a compound of embodiments 2 and 13-22) or a composition of embodiment 23).

Preparation of the Compounds of the Invention

It is understood that in the following description, combinations of substituents and/or variables of the depicted formulae are permissible only if such contributions result in stable compounds. It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R'' (where R'' is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wutz, Protective Groups in Organic Synthesis (1999), 3rd Ed., Wiley. The protecting group may also be a polymer resin such as a Wang resin or a 2-chlorotritylchloride resin. It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make quinazoline compounds of the present disclosure. It is understood that one of those skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

In general, compounds of formula (I) and formula (II) where X is —N(R10)-, —O—, and —S—, Y and Z are —O— may be synthesized following the general procedure as described in Reaction Scheme 1.

REACTION SCHEME 1

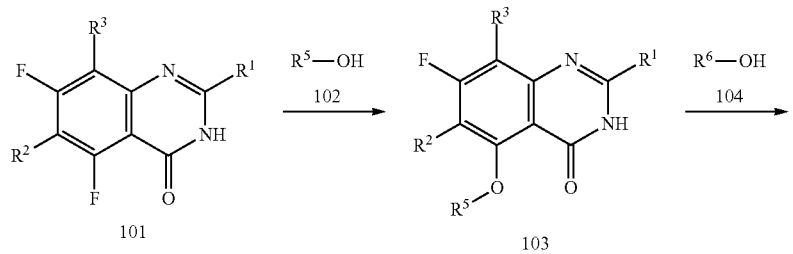

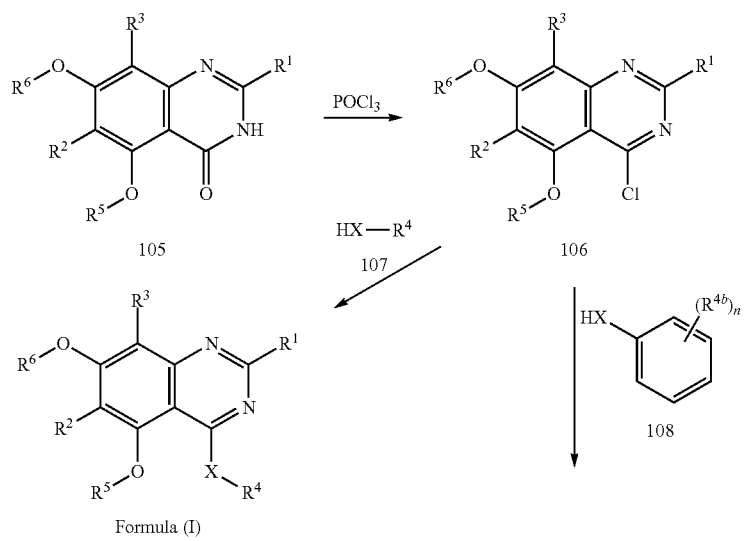

Formula (I)

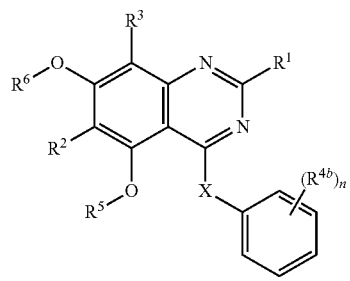

Formula (II)

The starting materials for the above reaction scheme are commercially available or can be prepared according to methods known to one skilled in the art or by methods disclosed herein. In general, the compounds of the invention are prepared in the above reaction scheme as follows:

The starting alcohol 102 is treated with sodium metal or sodium hydride to generate the alkoxy anion which reacts with 5,7-difluoroquinazolinone 101 to replace the 5-F group to generate compound 103. Alcohol 104 is treated with a base, such as, but not limited to, potassium t-butoxide and then reacts with 103 to replace the 7-F group to afford quinazolinone 105. Treatment of compound 105 with POCl₃ generates chloride 106. The chloro group is subsequently replaced by compound 107 in the presence of a base, such as, but not limited to, N,N-diisopropylethylamine to afford the compound of formula (I) where X is —N(R$^{10}$)—, —O—, and —S—, Y and Z are —O—. Alternatively, compound 106 reacts with compound 108 to generate the compound of formula (II) where X is —N(R$^{10}$)—, —O—, and —S—, Y and Z are —O—.

Alternatively, compounds of formula (I) and formula (II) where X is —N(R$^{10}$)—, —O—, and —S—, Y is —O— and Z is —N(R$^{10}$)— can be synthesized following the general procedure as described in Reaction Scheme 2.

REACTION SCHEME 2

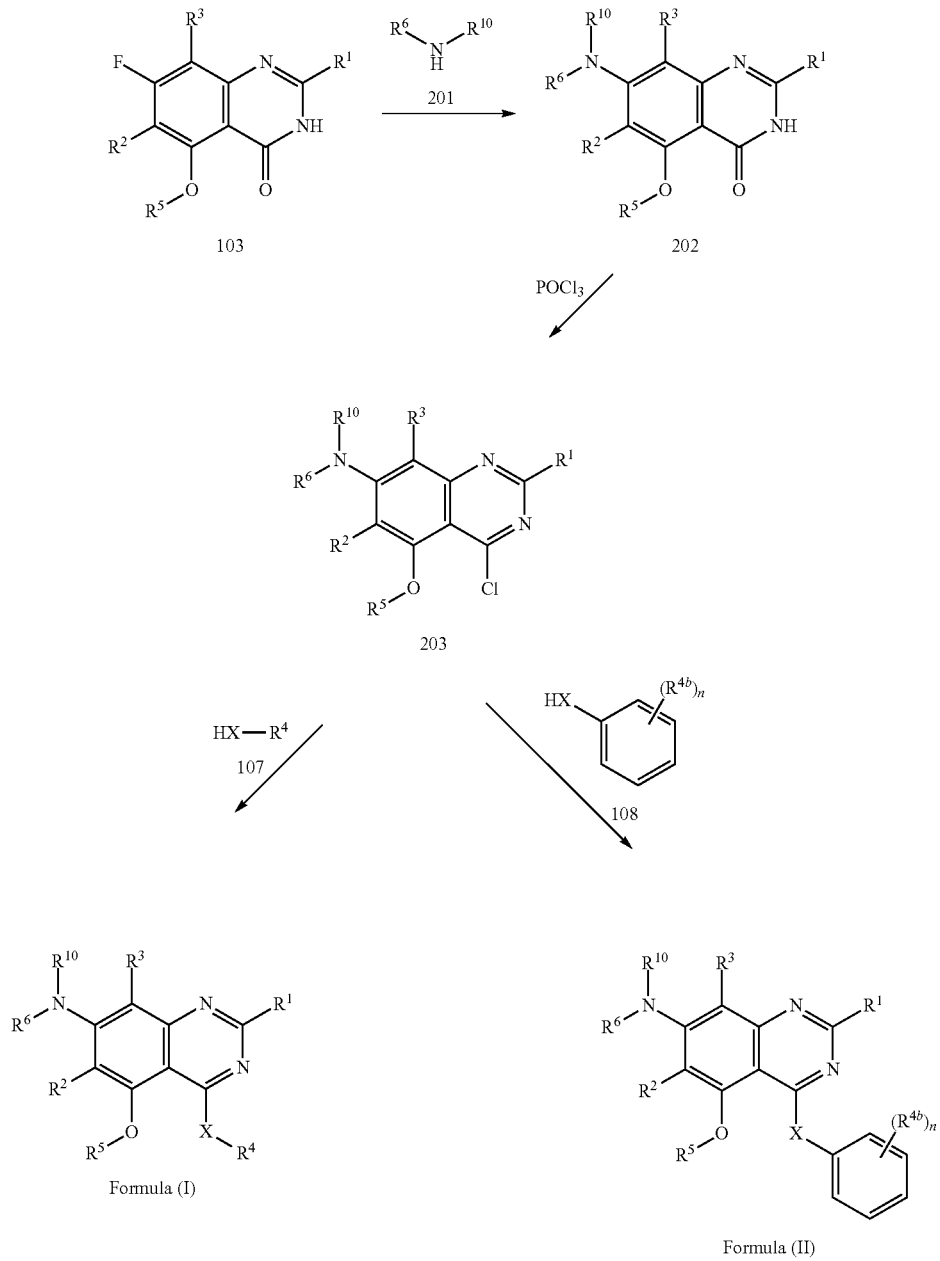

Formula (I)

Formula (II)

The starting materials for the above reaction scheme are commercially available or can be prepared according to methods known to one skilled in the art or by methods disclosed herein. In general, the compounds of the invention are prepared in the above reaction scheme as follows:

Amine 201 is treated with a base, such as, but not limited to, potassium t-butoxide and then reacts with compound 103 to replace the 7-F group to afford quinazolinone 202. Treatment of compound 202 with $POCl_3$ generates chloride 203. The chloro group is subsequently replaced by compound 107 in the presence of a base, such as, but not limited to, N,N-diisopropylethylamine to afford the compound of formula (I) where X is —$N(R^{10})$—, —O—, and —S—, Y is —O— and Z is —$N(R^{10})$—. Alternatively, compound 203 reacts with compound 204 to generate compound of formula (II) of the invention where X is —$N(R^{10})$—, —O—, and —S—, Y is —O— and Z is —$N(R^{10})$—.

Although anyone skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

Pharmaceutical Compositions and Administration

The present disclosure also relates to pharmaceutical composition containing the quinazoline compounds disclosed herein. In one embodiment, the present invention relates to a composition comprising compounds of the invention in a pharmaceutically acceptable carrier and in an amount effective to modulate the activity of Tyro3, Axl and Mer individually or in any combination of them or to treat diseases related to angiogenesis and/or cell proliferation and migration, and especially cancer, inflammatory diseases, autoimmune diseases, neurodisorders and the like when administered to an animal, preferably a mammal, most preferably a human patient. In an embodiment of such composition, the patient has hyperproliferative disease, and especially cancer, inflammatory diseases, autoimmune diseases, neurodisorders and the like, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are also familiar with determining administration methods (oral, intravenous, inhalation, subcutaneous, etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile. A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume). The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol. The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome. The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols. The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The present disclosure provides a process of preparing a pharmaceutical composition comprising the step of intimately mixing a pharmaceutically acceptable carrier with a therapeutically effective amount of a compound as defined by formulae (I) or (II) or a subset thereof.

The compounds of the invention can be used in combination with other therapeutic agents. Examples of alkylating agents that can be carried out in combination with include, but not limited to, fluorouracil (5-FU) alone or in further combination with leukovorin; other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Examples of antimetabolite chemotherapeutic agents that can be carried out in combination with include, but not limited to, folic acid analogs, e.g., methotrexate (used in the treatment of acute lymphocytic leukemia, choriocarcinoma, mycosis fungiodes, breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. Examples of natural product-based chemotherapeutic agents that can be carried out in combination with include, but not limited to, the vinca alkaloids, e.g., vinblastine (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

Examples of other signal transduction inhibiting agents that can be carried out in combination with include, but not limited to, gefitinib, erlotinib, sorafenib, herceptin, imatinib, dasatinib, sunitinib, nilotinib, lapatinib, pazopanib, vandetanib, vemurafenib, crizotinib, ruxolitinib, axitinib, bosutinib, regorafenib, tofacitinib, cabozantinib, ponatinib, dabrafenib, trametinib, and afatinib.

Other agents can be used in combination with the compound of the invention include, but not limited to, COX-II inhibitors, such as, but not limited to, Vioxx, Celebrex (celecoxib), valdecoxib, paracoxib, rofecoxib; matrix metalloproteinase inhibitors, such as, but not limited to, AG-3340, RO 32-3555, and RS 13-0830.

Utility and Testing of the Compounds of the Invention

The present invention relates to quinazoline compounds, pharmaceutical compositions and methods of using the compounds and pharmaceutical compositions for the treatment and/or prevention of diseases and conditions mediated by the kinase activity of Tyro3, Axl or Mer individually or by any combination of them, preferably diseases and conditions related to or characterized by angiogenesis and/or cell proliferation and migration, and especially a disease and condition related to cancer, inflammatory diseases, autoimmune diseases, neurodisorders, and the like, by administering an effective amount of a quinazoline compound.

The quinazoline compounds may be used to modulate, preferably inhibit, the activity of human Tyro3, Axl or Mer individually or any combination of them. The extent to which a quinazoline compound may modulate or inhibit the activity of Tyro3, Axl or Mer individually or in any combination can be determined using the assay described in Example 9.

The quinazoline compounds disclosed herein are useful as inhibitors of Tyro3, Axl or Mer individually or inhibitors of any combination of them and are useful for treating diseases and disorders in humans and other organisms, including all those human diseases and disorders which are the result of abnormal kinase activity of Tyro3, Axl or Mer individually or any combination of them or which may be ameliorated by modulation of the kinase activity of Tyro3, Axl or Mer individually or any combination of them.

As defined herein, a disease or condition mediated by an abnormal kinase activity of Tyro3, Axl or Mer individually or any combination of them is defined as any disease or condition in which the activity of Tyro3, Axl or Mer individually or any combination of them is elevated and/or where inhibition of the activity of Tyro3, Axl or Mer individually or any combination of them can be demonstrated to bring about symptomatic improvements for the individual so treated. As defined herein, a disease or condition mediated by the abnormal activity of Tyro3, Axl or Mer individually or any combination of them includes, but is not limited to, a disease or condition which is, or is related to cancer, inflammatory diseases, autoimmune diseases, and neurodisorders.

For purposes of the present disclosure, diseases, syndromes, disorders and conditions which are alleviated or ameliorated by the modulation of (for example, the inhibition of) the activity of Tyro3, Axl or Mer individually or any combination of them include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias particularly myeloid leukemias and lymphomas; endometriosis; vascular disease/injury including, but not limited to, restenosis, atherosclerosis and thrombosis; psoriasis; visual impairment due to macular degeneration; diabetic retinopathy and retinopathy of prematurity; kidney disease including, but not limited to, glomerulonephritis, diabetic nephropathy and renal transplant rejection, rheumatoid arthritis; osteoarthritis, osteoporosis and cataracts.

In addition to the foregoing, the quinazoline compounds of the present disclosure may be used in treating diseases and conditions which are affected by the following biological processes: invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostatasis as manifested in osteoporosis or osteoarthritis; viral infection as manifested, for example, in ebola virus infection; or differentiation as manifested in obesity. The quinazoline compounds disclosed herein may also be used to modulate inflammatory processes by treating sepsis, acting as vaccine adjuvants, and/or potentiating the immune response in immuno-compromised patients.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human cancer cell lines which express Tyro3 or Axl or Mer or co-expressing any combination of these three kinases including, but not limited to, A549, K562, HeLa, MDA-MB-231, SK-OV-3, OVCAR-8, DU145, H1299, ACHN, A498 and Caki-1.

The compounds of the invention may be tested for their use in treating leukemias in the xenograft in SCID or nu/nu mouse model using human AML and CML leukemia cell lines.

The compounds of the invention may be tested for their use in treating endometriosis by using the syngenic mouse model of endometriosis (see Somigliana, E. et al., "Endometrial ability to implant in ectopic sites can be prevented by interleukin-12 in a murine model of endometriosis", Hum. Reprod. 1999, 14(12), 2944-2950). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", Fertil. Steril., 2004, 82 Suppl 3, 1008-1013).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", Circulation, 2004, 109 (12), 1558-1563). The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", Arterioscler. Thromb. Vasc. Biol., 2004, 24(2), 357-362).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", Arterioscler. Thromb., 1994, 14(1), 133-140).

The compounds of the invention may also be tested for their use in treating thrombosis using the collagen-epinephrin-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", J. Clin. Invest., 2005, 115, 237-246).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", Am. J. Pathol., 1995, 146(3), 580-588).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. Exp. Eye. Res., 2005, 80(3), 435-442) or the laser-induced mouse choroidal neovasculation model (see Bora, P. S., et al., "Immunotherapy for choroidal neovascularization in a laser-induced mouse model simulating exudative (wet) macular degeneration", Proc. Natl. Acad. Sci. U.S.A., 2003, 100(5), 2679-2684).

The compounds of the invention may be tested for their use in treating retinopathy of prematurity in the mouse retinopathy of prematurity model (see Smith, L. E. et al., "Oxygen-induced retinopathy in the mouse", Invest. Ophthalmol. Vis. Sci., 1994, 35(1), 101-111). The compounds of the invention may be tested for their use in treating glomerulonephritis or diabetic nephropathy in the rat anti-Thy1.1-induced experimental mesengial proliferative glomerulonephritis model (see Smith, L. E. et al. cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", Transplantation, 2002, 73(4), 657-660).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", Immunopharmacology, 1985, 10(1), 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", Arthritis. Rheum., 1998, 41(9), 1639-1644).

The compounds of the invention may be tested for their use in treating osteoporosis by using the ovariectomized rat model (see Wronski, T J. et al., "Endocrine and pharmacological suppressors of bone turnover protect against osteopenia in ovariectomized rats", Endocrinology, 1989, 125(2), 810-816) or the ovariectomized mouse model (see Alexander, J. M. et al., "Human parathyroid hormone 1-34 reverses bone loss in ovariectomized mice", J Bone Miner Res., 2001, 16(9), 1665-1673; Fujioka, M. et al., "Equol, a metabolite of daidzein, inhibits bone loss in ovariectomized mice", J. Nut., 2004, 134(10), 2623-2627).

The compounds of the invention may be tested for their use in treating cataracts by using the H2O2-induced model (see Kadoya, K. et al., "Role of calpain in hydrogen peroxide induced cataract", Curr. Eye Res., 1993, 12(4), 341-346) or the Emory mouse model (see Sheets, N. L. et al., "Cataract- and lens-specific upregulation of ARK receptor tyrosine kinase in Emory mouse cataract", Invest. Ophthalmol. Vis. Sci., 2002, 43(6), 1870-1875).

Typically, a successful inhibitory therapeutic agent of the activity of Tyro3, Axl or Mer individually or any combination of them will meet some or all of the following criteria. Oral availability should be at or above 20% Animal model efficacy is less than about 20 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of the kinase activity, over a specific time period, in a kinase activity assay. Any process for measuring the kinase activity of Tyro3, Axl or Mer, preferably human Tyro3, Axl or Mer, may be utilized to assay the activity of the compounds useful in the methods of the invention in inhibiting said Tyro3, Axl or Mer activity. Compounds of the invention demonstrate an $IC_{50}$ in a 15 to 60 minute recombinant human kinase assay of preferably less than 10 mM, less than 5 µM, less than 2.5 µM, less than 1 µM. less than 750 nM, less than 500 nM, less than 250 nM, less than 100 nM, less than 50 nM, and most preferably less than 20 nM. Compounds of the invention may show reversible inhibition (i.e. competitive inhibition) or irreversible inhibition and preferably do not inhibit other protein kinases.

The identification of compounds of the invention as Tyro3, Axl or Mer inhibitors was readily accomplished using the recombinant human Tyro3, Axl and Mer proteins and employing the $^{33}P$-radiolabeled phosphate transfer assay for which the procedure is known to someone skilled in the art or as described in Example 9. When tested in this assay, compounds of the invention had greater than 50% inhibitory activity at 10 µM concentration of the test compound, preferably greater than 60% inhibitory activity at 10 µM concentration of the test compound, more preferably greater than 70% inhibitory activity at 10 µM concentration of the test compound, and even more preferably greater than 80% inhibitory activity at 10 µM concentration of the test compound, and the most preferably greater than 90% inhibitory activity at 10 µM concentration of the test compound, thereby demonstrating that the compounds of the invention are potent inhibitors of the kinase activity of Tyro3, Axl and Mer.

These results provide the basis for analysis of the structure-activity relationship (SAR) between test compounds and the kinase activity of Tyro3, Axl and Mer. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit Tyro3, Axl and Mer activity may be accomplished in vivo. In one such embodiment this is accomplished by administering said chemical agent to an animal afflicted with a certain tumor graft model and subsequently detecting a change in tumor growth rate in said animal thereby identifying a therapeutic agent useful in treating the said tumors. In such embodiment, the animal may be a human, such as a human patient afflicted with such a disorder and in need of treatment of said disorder.

In specific embodiments of such in vivo processes, said change in Tyro3, Axl or Mer activity in said animal is a decrease in activity, preferably wherein said Tyro3, Axl or Mer inhibiting agent does not substantially inhibit the biological activity of other kinases.

In one aspect, the present disclosure provides a method of treating or ameliorating a disease, syndrome, condition or disorder, such as those described above, that is affected by modulating the activity of a TAM kinase, comprising administering to a subject in need thereof, a therapeutically effective amount of a compound within the scope of formulae (I) or (II) and a pharmaceutical composition comprising such a compound. In another aspect, the present disclosure provides a method of treating a subject suffering from or diagnosed with a disease, disorder or medical condition mediated by a TAM kinase, such as those described above, comprising administering to a subject in need of such treatment an effective amount of at least one chemical entity selected from compounds of formulae (I) or (II).

EXAMPLES AND PREPARATIONS

Preparation 1

Preparation of 2-((2-methoxyethyl)(methyl)amino)ethanol

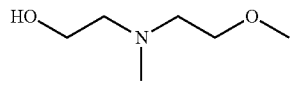

To a solution of 2-((2-hydroxyethyl)methylamino)ethanol (1.00 g, 8.40 mmol) in 50 mL of N,N-dimethylformamide at 0° C. was added sodium hydride in portions. The mixture was warmed up to room temperature and stirred for 10 min, and then cooled to 0° C. Methyl iodide was added dropwise. After the addition was completed, the mixture was warmed up to room temperature and stirred overnight. The solvent was removed in vacuo and the residue was purified by column chromatography eluted with 0.5:5:94.5 $NH_4OH$:methanol:dichloromethane to afford 2-((2-methoxyethyl)-(methyl)-amino)ethanol as a pale yellow oil in 32% yield (0.40 g). $^1H$ NMR (300 MHz, $CDCl_3$): δ4.08 (t, J=4.6 Hz, 2H), 3.91 (t, J=4.6 Hz, 2H), 3.54-3.42 (m, 4H), 3.41 (s, 3H), 3.02 (s, 3H).

Preparation 2

Preparation of 7-fluoro-5-((tetrahydro-2H-pyran-4-yl)oxy)quinazolin-4(3H)-one

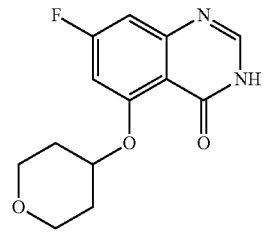 [SMILES: O=c1[nH]cnc2cc(F)cc(OC3CCOCC3)c12]

To a cold (0° C.) solution of tetrahydro-2H-pyran-4-ol (0.90 g, 8.78 mmol) in 10 mL of N,N-dimethylformamide was added sodium hydride (60% in mineral oil, 0.77 g, 19.2 mmol) in portions under nitrogen atmosphere. The mixture was warmed up to room temperature and stirred for 30 min to yield pale yellow slurry. The slurry was cooled to 0° C. and 5,7-difluoroquinazolin-4(3H)-one (1.00 g, 5.49 mmol) was added in portions. After the completion of the addition, the mixture was warmed up to room temperature and stirred for 2 h and then poured into ice-cold water and neutralized with acetic acid to pH 6-7 to yield pale brown precipitates. The precipitates were collected by filtration and washed with cold water (2×20 mL), diethyl ether (2×20 mL) and dried to afford 7-fluoro-5-((tetrahydro-2H-pyran-4-yl)oxy)quinazolin-4(3H)-one as a pale yellow powder in 73% yield (1.05 g). $^1$H NMR (300 MHz, CDCl$_3$): δ10.27 (br s, 1H), 7.95 (s, 1H), 7.00 (dd, J=9.4, 2.4 Hz, 1H), 6.68 (dd, J=9.4, 2.4 Hz, 1H), 4.75-4.65 (m, 1H), 4.15-4.05 (m, 2H), 3.72-3.62 (m, 2H), 2.19-1.90 (m, 4H).

Preparation 2.1

Preparation of 7-fluoro-5-(2-methoxyethoxy)quinazolin-4(3H)-one

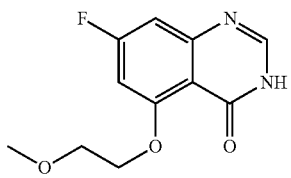 [SMILES: COCCOc1cc(F)cc2nc[nH]c(=O)c12]

Following the procedure as described in Preparation 2, replacing tetrahydro-2H-pyran-4-ol with 2-methoxyethanol to react with 5,7-difluoroquinazolin-4(3H)-one, 7-fluoro-5-(2-methoxyethoxy)quinazolin-4(3H)-one was obtained as a white solid in yield 70%. $^1$H NMR (300 MHz, DMSO-d$_6$): δ 8.55 (s, 1H), 7.95 (s, 1H), 7.71-7.67 (m, 1H), 6.75-6.70 (m, 1H), 4.15-4.05 (m, 2H), 3.75-3.65 (m, 2H), 3.50 (s, 3H).

Preparation 3

Preparation of 7-fluoro-5-methoxyquinazolin-4(3H)-one

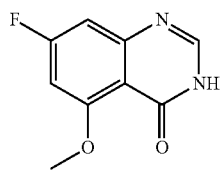

To a cold (0° C.) solution of methanol (3.52 g, 0.11 mol) was added sodium (5.06 g, 0.22 mol) in portions under nitrogen atmosphere. The resulting mixture was stirred at 0° C. for 30 min, followed by the addition of 5,7-difluoroquinazolin-4(3H)-one (4.00 g, 0.22 mol) in 50 mL of N,N-dimethylformamide. The mixture was warmed up to room temperature and stirred for 1 h and then poured into ice-cold water and the solution was neutralized to pH 6-7 with acetic acid (25 mL) to yield pale brown precipitates. The precipitates were collected by suction filtration and washed with cold water (3×20 mL), ethyl ether (2×20 mL) and dried to afford 7-fluoro-5-methoxy-quinazolin-4(3H)-one as a pale yellow solid in 94% yield (4.02 g). $^1$H NMR (300 MHz, CDCl$_3$): δ10.73 (br s, 1H), 8.00 (s, 1H), 6.98 (dd, J=9.3, 2.4 Hz, 1H), 6.66 (dd, J=9.3, 2.4 Hz, 1H), 4.01 (s, 3H).

Preparation 4

Preparation of 5-methoxy-7-((1-methylpiperidin-4-yl)methoxy)quinazolin-4(3H)-one

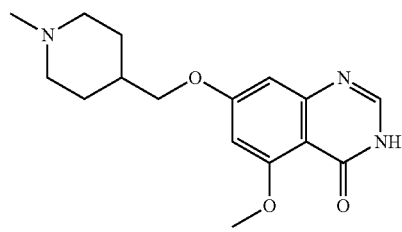 [SMILES: COc1cc(OCC2CCN(C)CC2)cc2nc[nH]c(=O)c12]

To a solution of 7-fluoro-5-methoxyquinazolin-4(3H)-one (0.10 g, 0.56 mmol) in 2 mL of N,N-dimethylformamide were added (1-methylpiperidin-4-yl)methanol (0.15 g, 1.12 mmol) and sodium hydride (60% in mineral oil, 0.11 g, 2.80 mmol). The mixture was heated at 95° C. for 1 h and dried in vacuo. The residue was purified by column chromatography eluted with 0.5:5:94.5 NH$_4$OH:methanol:dichloromethane to afford 5-methoxy-7-((1-methylpiperidin-4-yl)methoxy)quinazolin-4(3H)-one as a white foamy solid in 70% yield (0.12 g). $^1$H NMR (300 MHz, CDCl$_3$): δ 8.05 (s, 1H), 6.78 (d, J=2.3 Hz, 1H), 6.54 (d, J=2.3 Hz, 1H), 4.03 (s, 3H), 3.98 (d, J=5.8 Hz, 2H), 2.96-2.85 (m, 2H), 2.30 (s, 3H), 2.04-1.91 (m, 2H), 1.90-1.75 (m, 3H), 1.57-1.38 (m, 2H).

Preparation 5

Preparation of 7-(2-(piperidin-1-yl)ethoxy)-5-((tetrahydro-2H-pyran-4-yl)oxy)quinazolin-4(3H)-one

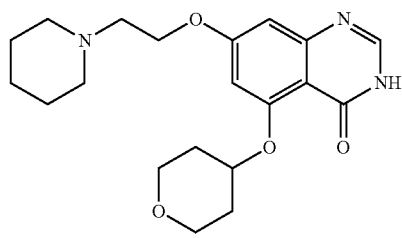 [SMILES: O=c1[nH]cnc2cc(OCCN3CCCCC3)cc(OC3CCOCC3)c12]

To a mixture of 7-fluoro-5-((tetrahydro-2H-pyran-4-yl)oxy)quinazolin-4(3H)-one (0.30 g, 1.14 mmol) and 2-(piperidin-1-yl)ethanol (0.18 g, 1.39 mmol) in 5 mL of N,N-dimethylformamide was added t-BuOK (0.78 g, 6.84 mmol). The solution was heated at 100° C. for 2 h, and then cooled to room temperature. The solvent was removed in vacuo and the residue was purified by column chromatography eluted with 0.5:5:94.5 NH$_4$OH:methanol:dichloromethane to afford 7-(2-(piperidin-1-yl)-ethoxy)-5-((tetrahydro-2H-pyran-4-yl)oxy)quinazolin-4(3H)-one as a pale yellow powder in 40% yield (0.17 g). $^1$H NMR (300 MHz, CDCl$_3$): δ7.92 (s, 1H), 6.96 (br s, 1H), 6.67 (d, J=2.4 Hz, 1H), 6.49 (d, J=2.4 Hz, 1H), 4.67-4.57 (m, 1H), 4.19 (t, J=5.9 Hz, 2H), 4.11-3.99 (m, 2H), 3.64-3.52 (m, 2H), 2.80 (t, J=5.9 Hz, 2H), 2.57-2.44 (m, 4H), 2.10-1.83 (m, 4H), 1.66-1.54 (m, 4H), 1.50-1.39 (m, 2H).

The intermediates listed below were prepared following the procedure as described in Preparation 5.

Preparation 5.1

Preparation of 7-(2-morpholinoethoxy)-5-((tetrahydro-2H-pyran-4-yl)oxy)quinazolin-4(3H)-one

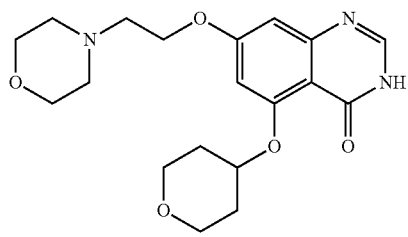 [SMILES: O=c1[nH]cnc2cc(OCCN3CCOCC3)cc(OC3CCOCC3)c12]

Following the procedure as described in Preparation 5, replacing 2-(piperidin-1-yl)ethanol with 2-morpholinoethanol to react with 7-fluoro-5-((tetrahydro-2H-pyran-4-yl)oxy)quinazolin-4(3H)-one, 7-(2-morpholinoethoxy)-5-((tetrahydro-2H-pyran-4-yl)oxy)-quinazolin-4(3H)-one was obtained as a pale yellow solid in 34% yield. $^1$H NMR (300 MHz, CDCl$_3$): δ7.92 (s, 1H), 6.76 (d, J=2.4 Hz, 1H), 6.53 (d, J=2.4 Hz, 1H), 4.70-4.60 (m, 1H), 4.21 (t, J=5.7 Hz, 2H), 4.23-4.00 (m, 2H), 3.80-3.71 (m, 4H), 3.70-3.60 (m, 2H), 2.84 (t, J=5.7 Hz, 2H), 2.59 (m, 4H), 2.20-2.00 (m, 4H).

Preparation 5.2

Preparation of 7-(2-(1-methylpiperidin-4-yl)ethoxy)-5-((tetrahydro-2H-pyran-4-yl)oxy)quinazolin-4(3H)-one

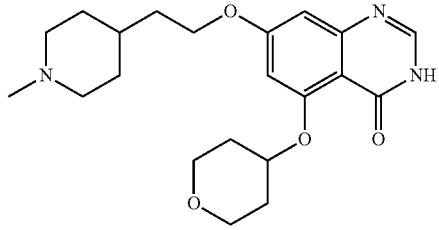 [SMILES: CN1CCC(CCOc2cc(OC3CCOCC3)c3c(=O)[nH]cnc3c2)CC1]

Following the procedure as described in Preparation 5, replacing 2-(piperidin-1-yl)ethanol with 2-(1-methylpiperidin-4-yl)ethanol to react with 7-fluoro-5-((tetrahydro-2H-pyran-4-yl)oxy)quinazolin-4(3H)-one, 7-(2-(1-methylpiperidin-4-yl)ethoxy)-5-((tetrahydro-2H-pyran-4-yl)oxy)quinazolin-4(3H)-one was obtained as a pale yellow solid in 39% yield. $^1$H NMR (300 MHz, CDCl$_3$): δ7.92 (s, 1H), 6.75 (d, J=2.4 Hz, 1H), 6.49 (d, J=2.4 Hz, 1H), 4.72-4.61 (m, 1H), 4.17-4.02 (m, 4H), 3.75-3.57 (m, 2H), 3.92-2.79 (m, 2H), 2.27 (s, 3H), 2.15-2.01 (m, 2H), 2.03-1.88 (m, 4H), 1.82-1.68 (m, 4H), 1.60-1.20 (m, 3H).

Preparation 5.3

Preparation of 7-(2-(2-(dimethylamino)ethoxy)ethoxy)-5-((tetrahydro-2H-pyran-4-yl)oxy)quinazolin-4(3H)-one

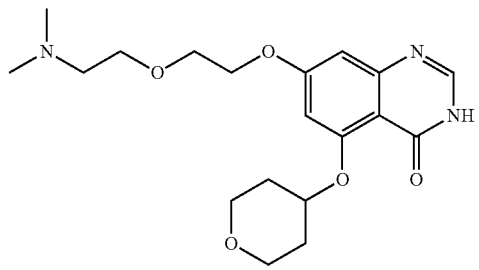 [SMILES: CN(C)CCOCCOc1cc(OC2CCOCC2)c2c(=O)[nH]cnc2c1]

Following the procedure as described in Preparation 5, replacing 2-(piperidin-1-yl)ethanol with 2-(2-dimethylaminoethoxy)ethanol to react with 7-fluoro-5-((tetrahydro-2H-pyran-4-yl)oxy)quinazolin-4(3H)-one, 7-(2-(2-(dimethylamino)-ethoxy)ethoxy)-5-((tetrahydro-2H-pyran-4-yl)oxy)quinazolin-4(3H)-one was obtained as a pale yellow solid in 47% yield. $^1$H NMR (300 MHz, CDCl$_3$): δ7.90 (s, 1H), 6.63 (d, J=2.0 Hz, 1H), 6.45 (d, J=2.0 Hz, 1H), 4.60-4.52 (m, 1H), 4.22-4.10 (m, 2H), 4.10-3.90 (m, 2H), 3.90-3.75 (m, 2H), 3.75-3.66 (t, J=5.7 Hz, 2H), 3.58-3.45 (m, 2H), 2.57 (t, J=5.7 Hz, 2H), 2.29 (s, 6H), 2.13-1.95 (m, 2H), 1.95-1.79 (m, 2H).

Preparation 5.4

Preparation of 7-(2-((2-methoxyethyl)(methyl)amino)ethoxy)-5-((tetrahydro-2H-pyran-4-yl)oxy)quinazolin-4(3H)-one

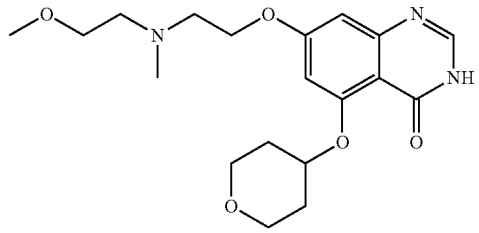 [SMILES: COCCN(C)CCOc1cc(OC2CCOCC2)c2c(=O)[nH]cnc2c1]

Following the procedure as described in Preparation 5, making necessary variations to replace 2-(piperidin-1-yl)ethanol with 2-((2-methoxyethyl)(methyl)-amino)ethanol to react with 7-fluoro-5-((tetrahydro-2H-pyran-4-yl)oxy)quinazolin-4(3H)-one, 7-(2-((2-methoxy-ethyl)(methyl)-amino)ethoxy)-5-((tetrahydro-2H-pyran-4-yl)oxy)-quinazolin-4(3H)-one was obtained as a yellow solid in 20% yield. $^1$H NMR (300 MHz, CDCl$_3$): δ7.98 (s, 1H), 6.72 (d, J=2.1 Hz, 1H), 6.59 (d, J=2.1 Hz, 1H), 4.70-4.58 (m, 1H), 4.27 (t, J=5.1 Hz, 2H), 4.12-4.00 (m, 2H), 3.68-3.52 (m, 4H), 3.33 (s, 3H), 3.13 (t, J=5.1 Hz, 2H), 2.93 (t, J=5.1 Hz, 2H), 2.57 (s, 3H), 2.12-1.99 (m, 2H), 1.97-1.81 (m, 2H).

Preparation 5.5

Preparation of 7-(2-(2-methoxyethoxy)ethoxy)-5-((tetrahydro-2H-pyran-4-yl)oxy)quinazolin-4(3H)-one

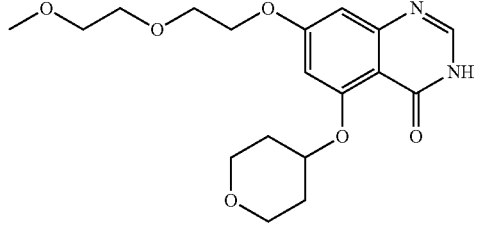 [SMILES: COCCOCCOc1cc(OC2CCOCC2)c2c(=O)[nH]cnc2c1]

Following the procedure as described in Preparation 5, replacing 2-(piperidin-1-yl)ethanol with 2-((2-methoxyethyl)methyl-amino)ethanol to react with 7-fluoro-5-((tetrahydro-2H-pyran-4-yl)oxy)quinazolin-4(3H)-one, 7-(2-(2-methoxyethoxy)ethoxy)-5-((tetrahydro-2H-pyran-4-yl)oxy)-quinazolin-4(3H)-one was obtained as a pale yellow solid in 40% yield. $^1$H NMR (300 MHz, CDCl$_3$): δ 10.32 (br s, 1H), 7.92 (s, 1H), 6.75 (d, J=2.4 Hz, 1H), 6.57 (d, J=2.4 Hz, 1H), 4.70-4.60 (m, 1H), 4.26-4.20 (m, 2H), 4.15-4.04 (m, 2H), 3.94-3.87 (m, 2H), 3.76-3.70 (m, 2H), 3.68-3.56 (m, 4H), 3.40 (s, 3H), 2.16-2.04 (m, 2H), 2.03-1.87 (m, 2H).

Preparation 5.6

Preparation of 7-(3-morpholinopropoxy)-5-((tetrahydro-2H-pyran-4-yl)oxy)quinazolin-4(3H)-one

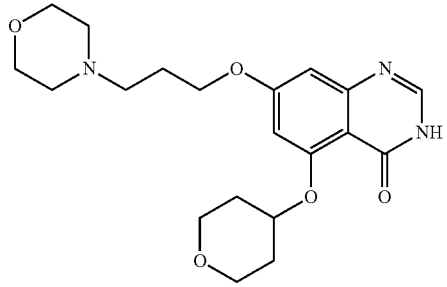 [SMILES: O=c1[nH]cnc2cc(OCCCN3CCOCC3)cc(OC3CCOCC3)c12]

Following the procedure as described in Preparation 5, replacing 2-(piperidin-1-yl)ethanol with 3-morpholin-4-yl-propan-1-ol to react with 7-fluoro-5-((tetrahydro-2H-pyran-4-yl)oxy)quinazolin-4(3H)-one, 7-(3-morpholinopropoxy)-5-((tetrahydro-2H-pyran-4-yl)oxy)quinazolin-4(3H)-one was obtained as a white solid in 35% yield. $^1$H NMR (300 MHz, CDCl$_3$): δ7.96 (s, 1H), 6.77 (d, J=2.4 Hz, 1H), 6.50 (d, J=2.4 Hz, 1H), 4.71-4.62 (m, 1H), 4.15-4.05 (m, 4H), 3.74-3.59 (m, 6H), 2.51-2.42 (m, 4H), 2.15-1.89 (m, 6H), 1.97-1.81 (m, 2H).

Preparation 5.7

Preparation of 7-(2-(4-methylpiperazin-1-yl)ethoxy)-5-((tetrahydro-2H-pyran-4-yl)oxy)quinazolin-4(3H)-one

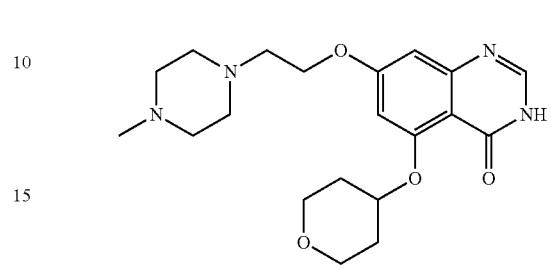

Following the procedure as described in Preparation 5, replacing 2-(piperidin-1-yl)ethanol with 2-(4-methylpiperazin-1-yl)ethanol to react with 7-fluoro-5-((tetrahydro-2H-pyran-4-yl)oxy)quinazolin-4(3H)-one, 7-(2-(4-methylpiperazin-1-yl)ethoxy)-5-((tetrahydro-2H-pyran-4-yl)oxy)quinazolin-4(3H)-one was obtained as a pale yellow solid in 55% yield. $^1$H NMR (300 MHz, CDCl$_3$): δ7.93 (s, 1H), 6.76 (d, J=2.3 Hz, 1H), 6.53 (d, J=2.3 Hz, 1H), 4.70-4.60 (m, 1H), 4.21 (t, J=5.6 Hz, 2H), 4.14-4.04 (m, 2H), 3.68-3.60 (m, 2H), 2.86 (t, J=5.6 Hz, 2H), 2.70-2.56 (m, 4H), 2.56-2.40 (m, 4H), 2.30 (s, 3H), 2.14-2.01 (m, 2H), 2.00-1.95 (m, 2H).

Preparation 5.8

Preparation of (S)-7-((2,2-dimethyl-1,3-dioxolan-4-yl)methoxy)-5-((tetrahydro-2H-pyran-4-yl)oxy)quinazolin-4(3H)-one

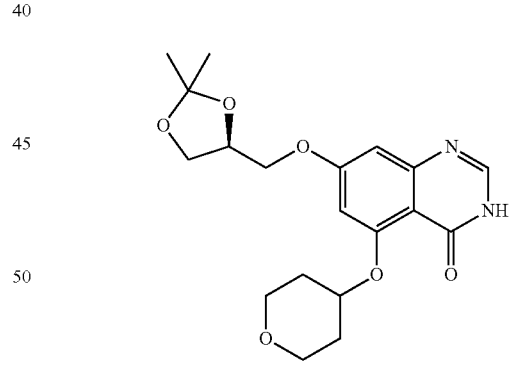

Following the procedure as described in Preparation 5, replacing 2-(piperidin-1-yl)ethanol with (S)-(+)-1,2-isopropylideneglycerol to react with 7-fluoro-5-((tetrahydro-2H-pyran-4-yl)oxy)quinazolin-4(3H)-one, (S)-7-((2,2-dimethyl-1,3-dioxolan-4-yl)-methoxy)-5-((tetrahydro-2H-pyran-4-yl)oxy)quinazolin-4(3H)-one was obtained as a pale yellow foamy solid in 19% yield. $^1$H NMR (300 MHz, CDCl$_3$): δ7.94 (s, 1H), 6.77 (d, J=2.4 Hz, 1H), 6.56 (d, J=2.4 Hz, 1H), 4.70-4.62 (m, 1H), 4.53 (m, 1H), 4.19 (dd, J=8.6, 6.4 Hz, 1H), 4.16-4.04 (m, 4H), 3.90 (dd, J=8.6, 5.7 Hz, 1H), 3.68-3.60 (m, 2H), 2.14-1.90 (m, 4H), 1.48 (s, 3H), 1.42 (s, 3H).

Preparation 5.9

Preparation of 5-methoxy-7-(2-(4-methylpiperazin-1-yl)ethoxy)quinazolin-4(3H)-one

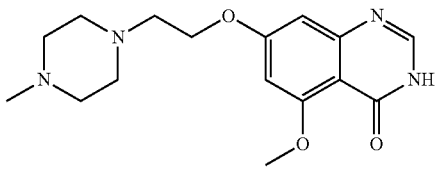 [SMILES: COc1cc(OCCN2CCN(C)CC2)cc2nc[nH]c(=O)c12]

Following the procedure as described in Preparation 5, replacing 7-fluoro-5-((tetrahydro-2H-pyran-4-yl)oxy)quinazolin-4(3H)-one with 7-fluoro-5-methoxy-quinazolin-4(3H)-one to react with 2-(4-methylpiperazin-1-yl)ethanol, 5-methoxy-7-(2-(4-methylpiperazin-1-yl)ethoxy)quinazolin-4(3H)-one was obtained as a foamy solid in 45% yield. $^1$H NMR (CDCl$_3$): δ7.98 (s, 1H), 6.74 (d, J=2.1 Hz, 1H), 6.53 (d, J=2.1 Hz, 1H), 4.22 (t, J=5.8 Hz, 2H), 3.98 (s, 3H), 2.87 (t, J=5.8 Hz, 2H), 2.70-2.61 (m, 4H), 2.61-2.44 (m, 4H), 2.31 (s, 3H).

Preparation 5.10

Preparation of 5-(2-methoxyethoxy)-7-(2-(4-methylpiperazin-1-yl)ethoxy)quinazolin-4(3H)-one

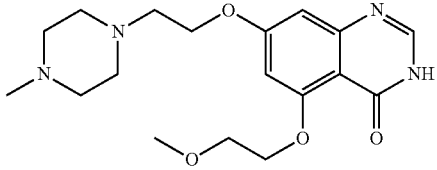 [SMILES: COCCOc1cc(OCCN2CCN(C)CC2)cc2nc[nH]c(=O)c12]

Following the procedure as described in Preparation 5, replacing 7-fluoro-5-((tetrahydro-2H-pyran-4-yl)oxy)quinazolin-4(3H)-one with 7-fluoro-5-(2-methoxy-ethoxy)quinazolin-4(3H)-one to react with 2-(4-methylpiperazin-1-yl)ethanol, 5-(2-methoxyethoxy)-7-(2-(4-methylpiperazin-1-yl)-ethoxy)-quinazolin-4(3H)-one was obtained as a foamy solid in 37% yield. $^1$H NMR (300 MHz, CDCl$_3$): δ7.96 (s, 1H), 6.78 (d, J=2.1 Hz, 1H), 6.58 (d, J=2.1 Hz, 1H), 4.30-4.15 (m, 4H), 3.95 (t, J=5.1 Hz, 2H), 3.53 (s, 3H), 2.90 (t, J=5.1 Hz, 2H), 2.2.70-2.45 (m, 8H), 2.35 (s, 3H).

Preparation 5.11

Preparation of 7-(2-((2-(dimethylamino)ethyl)(methyl)amino)ethoxy)-5-((tetrahydro-2H-pyran-4-yl)oxy)quinazolin-4(3H)-one

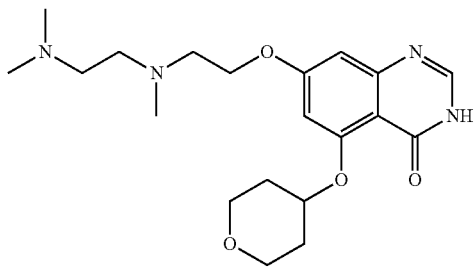 [SMILES: CN(C)CCN(C)CCOc1cc(OC2CCOCC2)c2c(=O)[nH]cnc2c1]

Following the procedure as described in Preparation 5, replacing 2-(piperidin-1-yl)ethanol with 2-((2-(dimethylamino)ethyl)(methyl)amino)ethanol to react with 7-fluoro-5-((tetrahydro-2H-pyran-4-yl)oxy)quinazolin-4(3H)-one, 7-(2-((2-(dimethyl-amino)ethyl)-(methyl)amino)ethoxy)-5-((tetrahydro-2H-pyran-4-yl)oxy)quinazolin-4(3H)-one was obtained as a foamy solid in 60% yield. $^1$H NMR (300 MHz, CDCl$_3$): δ7.93 (s, 1H), 6.75 (d, J=2.3 Hz, 1H), 6.53 (d, J=2.3 Hz, 1H), 4.70-4.60 (m, 1H), 4.20-4.11 (m, 2H), 4.10-4.00 (m, 2H), 3.65-3.55 (m, 2H), 2.95-2.85 (m, 2H), 2.65-2.56 (m, 2H), 2.55-2.45 (m, 2H), 2.38 (s, 3H), 2.25 (s, 6H), 2.20-2.10 (m, 2H), 2.20-2.19 (m, 2H).

Preparation 5.12

Preparation of 5-methoxy-7-(3-morpholinopropoxy)quinazolin-4(3H)-one

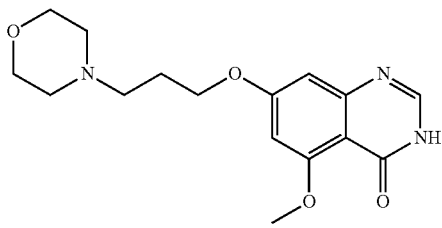 [SMILES: COc1cc(OCCCN2CCOCC2)cc2nc[nH]c(=O)c12]

Following the procedure as described in Preparation 5, replacing 7-fluoro-5-((tetrahydro-2H-pyran-4-yl)oxy)quinazolin-4(3H)-one with 7-fluoro-5-methoxy-quinazolin-4(3H)-one to react with 3-morpholin-4-yl-propan-1-ol, 5-methoxy-7-(3-morpholinopropoxy)quinazolin-4(3H)-one was obtained as a white solid in 36% yield. $^1$H NMR (300 MHz, CDCl$_3$): δ8.02 (s, 1H), 6.74 (d, J=2.1 Hz, 1H), 6.48 (d, J=2.1 Hz, 1H), 4.14 (t, J=6.3 Hz, 2H), 3.97 (s, 3H), 3.76-3.64 (m, 4H), 2.60-2.42 (m, 6H), 2.08-1.96 (m, 2H).

Preparation 5.13

Preparation of 7-((1-methylpiperidin-4-yl)methoxy)-5-((tetrahydro-2H-pyran-4-yl)oxy)quinazolin-4(3H)-one

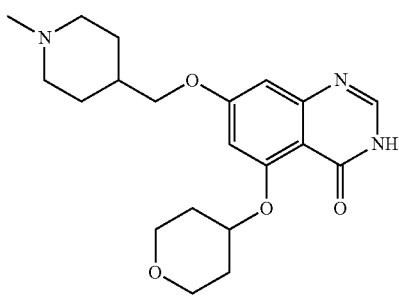 [SMILES: CN1CCC(COc2cc(OC3CCOCC3)c3c(=O)[nH]cnc3c2)CC1]

Following the procedure as described in Preparation 5, replacing 2-(piperidin-1-yl)ethanol with (1-methylpiperidin-4-yl)methanol to react with 7-fluoro-5-((tetrahydro-2H-pyran-4-yl)oxy)quinazolin-4(3H)-one, 7-((1-methylpiperidin-4-yl)methoxy)-5-((tetrahydro-2H-pyran-4-yl)oxy)quinazolin-4(3H)-one was obtained as a foamy solid in 50% yield. $^1$H NMR (300 MHz, CDCl$_3$): δ7.94 (s, 1H), 6.75 (d, J=1.8 Hz, 1H), 6.51 (d, J=1.8 Hz, 1H), 4.72-4.63 (m, 1H), 4.17-4.08 (m, 2H), 3.93 (d, J=5.2 Hz, 2H), 3.72-3.60 (m, 2H), 2.98-2.85 (m, 2H), 2.31 (s, 3H), 2.15-2.05 (m, 2H), 2.05-1.92 (m, 4H), 1.90-1.78 (m, 3H), 1.56-1.40 (m, 2H).

Preparation 6

Preparation of 7-(4-(2-methoxyethyl)piperazin-1-yl)-5-((tetrahydro-2H-pyran-4-yl)oxy)quinazolin-4(3H)-one

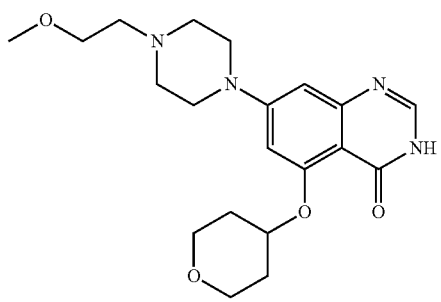 [SMILES: COCCN1CCN(c2cc(OC3CCOCC3)c3c(=O)[nH]cnc3c2)CC1]

A mixture of 7-fluoro-5-(tetrahydro-2H-pyran-4-yloxy)quinazolin-4(3H)-one (0.25 g, 0.95 mmol) and 1-(2-methoxyethyl)piperazine (0.22 g, 1.52 mmol) in 1 mL of N,N-dimethylformamide was refluxed overnight. The crude product was purified by column chromatography eluted with 0.5:5:94.5 NH$_4$OH:methanol:dichloromethane to afford 7-(4-(2-methoxyethyl)piperazin-1-yl)-5-((tetrahydro-2H-pyran-4-yl)oxy)-quinazolin-4(3H)-one as a yellow oil in 18% yield (65 mg). $^1$H NMR (400 MHz, CDCl$_3$): δ7.88 (s, 1H), 6.72 (d, J=2.0 Hz, 1H), 6.50 (d, J=2.0 Hz, 1H), 4.65-4.57 (m, 1H), 4.13-4.06 (m, 2H), 3.65-3.50 (m, 4H), 3.45-3.40 (m, 2H), 3.38 (s, 3H), 3.37-3.32 (m, 2H), 2.70-2.62 (m, 6H), 2.12-2.03 (m, 2H), 2.00-1.90 (m, 2H).

Preparation 6.1

Preparation of 7-(4-(2-(dimethylamino)ethyl)piperidin-1-yl)-5-((tetrahydro-2H-pyran-4-yl)oxy)quinazolin-4(3H)-one

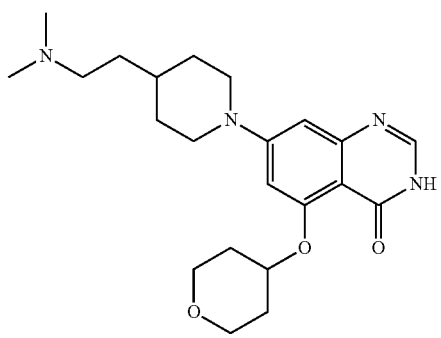 [SMILES: CN(C)CCC1CCN(c2cc(OC3CCOCC3)c3c(=O)[nH]cnc3c2)CC1]

Following the procedure as described in Preparation 6, replacing 1-(2-methoxyethyl)piperazine with N,N-dimethyl-2-(piperidin-4-yl)ethanamine to react with 7-fluoro-5-((tetrahydro-2H-pyran-4-yl)oxy)quinazolin-4(3H)-one, 7-(4-(2-(dimethyl-amino)ethyl)piperidin-1-yl)-5-((tetrahydro-2H-pyran-4-yl)oxy)quinazolin-4(3H)-one was obtained as a yellow foam in 47% yield. $^1$H NMR (400 MHz, CDCl$_3$): δ8.01 (s, 1H), 7.83 (s, 1H), 6.70 (d, J=2.4 Hz, 1H), 6.48 (d, J=2.4 Hz, 1H), 4.65-4.55 (m, 1H), 4.13-4.06 (m, 2H), 3.95-3.85 (m, 2H), 3.65-3.55 (m, 2H), 2.97-2.87 (m, 2H), 2.36-2.27 (m, 2H), 2.23 (s, 6H), 2.12-2.03 (m, 2H), 2.00-1.90 (m, 2H), 1.85-1.70 (m, 2H), 1.70-1.55 (m, 1H), 1.50-1.40 (m, 2H), 1.40-1.23 (m, 2H).

Preparation 7

Preparation of 4-chloro-7-(2-(piperidin-1-yl)ethoxy)-5-((tetrahydro-2H-pyran-4-yl)oxy)quinazoline

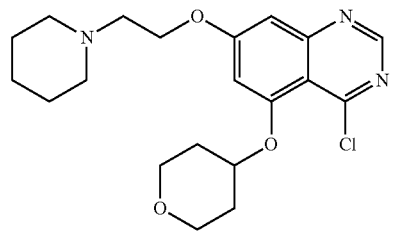 [SMILES: Clc1ncnc2cc(OCCN3CCCCC3)cc(OC3CCOCC3)c12]

To a solution of 7-(2-(piperidin-1-yl)ethoxy)-5-((tetrahydro-2H-pyran-4-yl)oxy)-quinazolin-4(3H)-one (0.05 g, 0.13 mmol) in 5 mL 1,2-dichloroethane were added N,N-diisopropylethylamine (0.12 mL, 0.71 mmol) and POCl$_3$ (0.03 mL, 0.34 mmol). The mixture was refluxed for 2 h and the solvent and excess POCl$_3$ was removed in vacuo. The residue was purified by column chromatography eluted with 0.5:5:94.5 NH$_4$OH:methanol:dichloromethane to afford 4-chloro-7-(2-(piperidin-1-yl)ethoxy)-5-((tetrahydro-2H-pyran-4-yl)oxy)quinazoline as a brown oil in 19% yield (17 mg). $^1$H NMR (300 MHz, CDCl$_3$): δ8.80 (s, 1H), 6.94 (d, J=2.3 Hz, 1H), 6.65 (d, J=2.3 Hz, 1H), 4.83-4.70 (m, 1H), 4.29 (t, J=5.8 Hz, 2H), 4.10-4.00 (m, 2H), 3.74-3.60 (m, 2H), 2.91 (t, J=5.8 Hz, 2H), 2.63-2.55 (m, 4H), 2.17-2.03 (m, 2H), 2.03-1.91 (m, 2H), 1.73-1.60 (m, 4H), 1.54-1.45 (m, 2H).

Preparation 7.1

Preparation of 4-chloro-7-methoxy-5-((tetrahydro-2H-pyran-4-yl)oxy)quinazoline

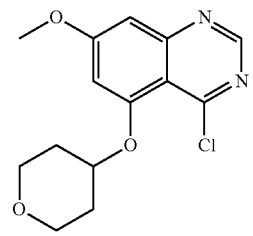 [SMILES: COc1cc(OC2CCOCC2)c2c(Cl)ncnc2c1]

Following the procedure as described in Preparation 7, replacing 7-(2-(piperidin-1-yl)ethoxy)-5-((tetrahydro-2H-pyran-4-yl)oxy)quinazolin-4(3H)-one with 7-methoxy-5-((tetrahydro-2H-pyran-4-yl)oxy)quinazolin-4(3H)-one, 4-chloro-7-methoxy-5-((tetrahydro-2H-pyran-4-yl)oxy)quinazoline was obtained as a white solid in 36% yield. $^1$H NMR (300 MHz, CDCl$_3$): δ8.82 (s, 1H), 6.97 (d, J=2.3 Hz, 1H), 6.61 (d, J=2.3 Hz, 1H), 4.80-4.70 (m, 1H), 4.10-4.05 (m, 2H), 3.95 (s, 3H), 3.70-3.60 (m, 2H), 2.10-2.20 (m, 2H), 1.95-2.15 (m, 2H).

Preparation 7.2

Preparation of 4-chloro-7-((1-methylpiperidin-4-yl)methoxy)-5-((tetrahydro-2H-pyran-4-yl)oxy)quinazoline

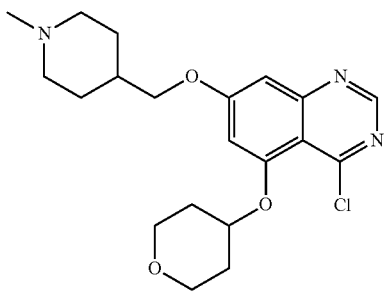 [SMILES: CN1CCC(COc2cc(OC3CCOCC3)c3c(Cl)ncnc3c2)CC1]

Following the procedure as described in Preparation 7, replacing 7-(2-(piperidin-1-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one, 4-chloro-7-((1-methylpiperidin-4-yl)methoxy)-5-((tetrahydro-2H-pyran-4-yl)oxy)-quinazoline was obtained as a white foamy solid in 13% yield. $^1$H NMR (300 MHz, CDCl$_3$): δ8.80 (s, 1H), 6.92 (d, J=2.4 Hz, 1H), 6.59 (d, J=2.4 Hz, 1H), 4.80-4.68 (m, 1H), 4.12-4.02 (m, 2H), 3.98 (d, J=5.7 Hz, 2H), 3.75-3.64 (m, 2H), 3.00-2.88 (m, 2H), 2.34 (s, 3H), 2.19-1.93 (m, 7H), 1.92-1.80 (m, 2H), 1.65-1.46 (m, 2H).

Preparation 8

Preparation of 4-chloro-7-(2-(4-methylpiperazin-1-yl)ethoxy)-5-((tetrahydro-2H-pyran-4-yl)oxy)quinazoline

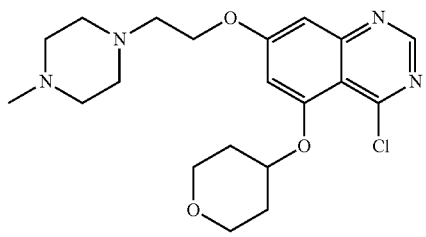 [SMILES: CN1CCN(CCOc2cc(OC3CCOCC3)c3c(Cl)ncnc3c2)CC1]

To a solution of 7-(2-(4-methylpiperazin-1-yl)ethoxy)-5-((tetrahydro-2H-pyran-4-yl)oxy)quinazolin-4(3H)-one (0.29 g, 0.74 mmol) in 12 mL of dichloroethane was added triphenylphosphine (0.58 g, 2.21 mmol), followed by the addition of carbon tetrachloride (0.43 mL, 4.42 mmol). The mixture was heated at 75° C. for 3 h. The volatiles were removed in vacuo and the residue was purified by column chromatography eluted with 0.5:5:94.5 NH$_4$OH:methanol:dichloromethane to afford 4-chloro-7-(2-(4-methylpiperazin-1-yl)ethoxy)-5-((tetrahydro-2H-pyran-4-yl)oxy)-quinazoline as a pale yellow solid in 90% yield (0.27 g). $^1$H NMR (300 MHz, CDCl$_3$): δ8.81 (s, 1H), 6.94 (d, J=2.3 Hz, 1H), 6.63 (d, J=2.3 Hz, 1H), 4.80-4.70 (m, 1H), 4.30-4.20 (m, 2H), 4.10-4.00 (m, 2H), 3.65-3.75 (m, 2H), 2.95-2.85 (m, 2H), 2.75-2.55 (m, 8H), 2.38 (s, 3H), 2.20-2.10 (m, 2H), 2.00-1.90 (m, 2H).

Preparation 8.1

Preparation of 4-chloro-5-(2-methoxyethoxy)-7-(2-(4-methylpiperazin-1-yl)ethoxy)quinazoline

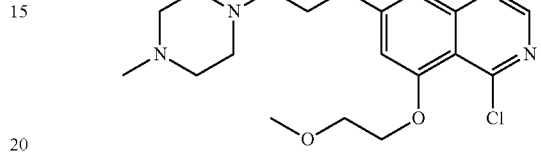

Following the procedure as described in Preparation 8, replacing 7-(2-(4-methylpiperazin-1-yl)ethoxy)-5-((tetrahydro-2H-pyran-4-yl)oxy)quinazolin-4(3H)-one with 5-(2-methoxyethoxy)-7-(2-(4-methylpiperazin-1-yl)ethoxy)quinazolin-4(3H)-one, 4-chloro-5-(2-methoxyethoxy)-7-(2-(4-methylpiperazin-1-yl)ethoxy)quinazoline was obtained as a foamy solid in 74% yield. $^1$H NMR (300 MHz, CDCl$_3$): δ8.90 (s, 1H), 7.00 (d, J=2.3 Hz, 1H), 6.70 (d, J=2.3 Hz, 1H), 4.40-4.30 (m, 4H), 4.00-3.90 (m, 2H), 3.55 (s, 3H), 3.00-2.95 (m, 2H), 2.70-2.50 (m, 8H), 2.38 (s, 3H).

Preparation 9

Preparation of 5-morpholino-7-(3-morpholinopropoxy)quinazolin-4(3H)-one

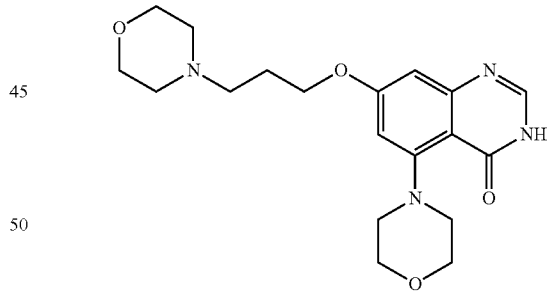

A mixture of 5,7-difluoroquinazolin-4(3H)-one (0.30 g, 1.65 mmol) and morpholine (0.29 mL, 3.30 mmol) in 2 mL of N,N-dimethylformamide was refluxed at 110° C. for 2 h. After the reaction solution was cooled down to room temperature, 3-morpholinopropan-1-ol (0.26 g, 1.82 mmol) and t-BuOK (0.74 g, 6.60 mmol) were added. The resulting reaction mixture was refluxed at 110° C. for 6 h. After removal of solvent in vacuo, the yellow solid residue was purified by column chromatography eluted with 0.5:5:94.5 NH$_4$OH:methanol:dichloromethane to afford 5-morpholino-7-(3-morpholinopropoxy)-quinazolin-4(3H)-one as a yellow foamy solid in 32% yield (0.20 g). $^1$H NMR (300 MHz, CDCl$_3$): δ7.94 (s, 1H), 6.81 (d, J=2.4 Hz, 1H), 6.54 (d, J=2.4

Hz, 1H), 4.15 (t, J=6.3 Hz, 2H), 4.02-3.94 (m, 4H), 3.78-3.68 (m, 4H), 3.14 (br s, 4H), 2.58-2.40 (m, 6H), 2.08-1.96 (m, 2H).

Preparation 9.1

Preparation of 5-(4-methylpiperazin-1-yl)-7-(3-morpholinopropoxy)quinazolin-4(3H)-one

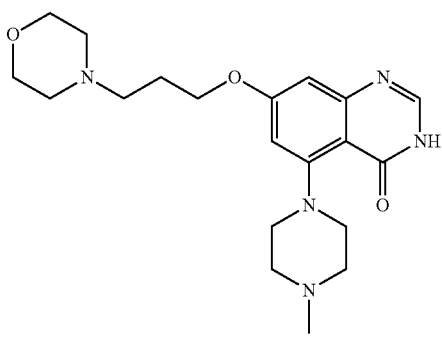 [SMILES: CN1CCN(c2cc(OCCCN3CCOCC3)cc3nc[nH]c(=O)c23)CC1]

Following the procedure as described in Preparation 9, replacing morpholine with 1-methylpiperazine, 5-morpholino-7-(3-morpholinopropoxy)quinazolin-4(3H)-one was obtained as a pale yellow foamy solid in 47% yield. $^1$H NMR (300 MHz, CDCl$_3$): δ7.94 (s, 1H), 6.79 (d, J=2.4 Hz, 1H), 6.56 (d, J=2.4 Hz, 1H), 4.14 (t, J=6.6 Hz, 2H), 3.80-3.70 (m, 4H), 3.18 (br s, 4H), 2.71 (br s, 4H), 2.60-2.48 (m, 6H), 2.40 (s, 3H), 2.10-1.96 (m, 2H).

Preparation 10

Preparation of 5-methoxy-7-morpholinoquinazolin-4(3H)-one

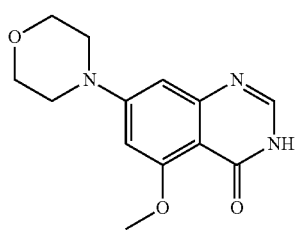 [SMILES: COc1cc(N2CCOCC2)cc2nc[nH]c(=O)c12]

A solution of 7-fluoro-5-methoxyquinazolin-4(3H)-one (0.20, 1.03 mmol) in 3 mL of morpholine was refluxed at 120° C. overnight. After removal of excess morpholine, the residue was purified by column chromatography eluted with 5:95 methanol:dichloromethane to afford 5-methoxy-7-morpholinoquinazolin-4(3H)-one as a yellowish foam in 97% yield (0.26 g). $^1$H NMR (300 MHz, CDCl$_3$): δ7.98 (s, 1H), 6.68 (d, J=2.1 Hz, 1H), 6.42 (d, J=2.1 Hz, 1H), 4.00 (s, 3H), 3.91-3.82 (m, 4H), 3.42-3.35 (m, 4H).

Preparation 11

Preparation of 5-methoxy-7-(4-methylpiperazin-1-yl)quinazolin-4(3H)-one

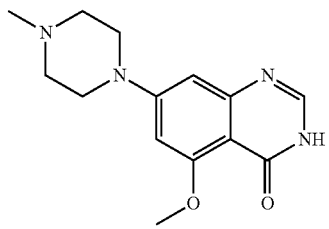 [SMILES: COc1cc(N2CCN(C)CC2)cc2nc[nH]c(=O)c12]

A solution of 7-fluoro-5-methoxyquinazolin-4(3H)-one (0.15 g, 0.77 mmol) in 2 mL of 1-methylpiperazine was refluxed at 90° C. overnight. After removal of excess 1-methylpiperazine, the residue was purified by column chromatography eluted with 5:95 methanol:dichloromethane to afford 5-methoxy-7-(4-methylpiperazin-1-yl)quinazolin-4(3H)-one as a yellow oil in 75% yield (0.15 g). $^1$H NMR (300 MHz, CDCl$_3$): δ7.97 (s, 1H), 6.67 (d, J=2.4 Hz, 1H), 6.42 (d, J=2.4 Hz, 1H), 3.99 (s, 3H), 3.46-3.37 (m, 4H), 2.62-2.50 (m, 4H), 2.36 (s, 3H).

Preparation 12

Preparation of methyl 3-hydroxybenzoate

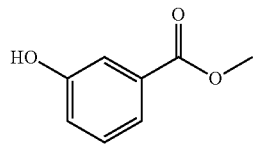

3-hydroxylbenzoic acid (3.45 g, 25.00 mmol) in 50 mL of methanol was heated at reflux with 1 mL of concentrated H$_2$SO$_4$ for 15 h and methanol was removed in vacuo. The residue was diluted with 100 mL of water and extracted with 50 mL of ethyl acetate. The organic layer was separated, washed with water and concentrated to afford methyl 3-hydroxybenzoate as a colourless oil in 95% yield (3.60 g). $^1$H NMR (300 MHz, CDCl$_3$): δ7.65-7.55 (m, 2H), 7.35-7.25 (m, 1H), 7.10-7.05 (m, 1H), 3.32 (s, 3H).

Preparation 12.1

Preparation of methyl 2-(3-hydroxyphenyl)acetate

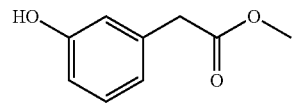

Following the procedure as described in Preparation 12, replacing methyl 3-hydroxybenzoate with 2-(3-hydroxyphenyl)acetic acid, methyl 2-(3-hydroxyphenyl)-acetate was obtained as a colourless oil in 93% yield. $^1$H NMR (300

MHz, CDCl$_3$): δ7.25-7.15 (m, 1H), 6.85-6.75 (m, 3H), 5.50-5.30 (m, 1H), 3.72 (s, 3H), 3.60 (s, 2H).

Preparation 13

Preparation of N-benzyl-3-hydroxybenzamide

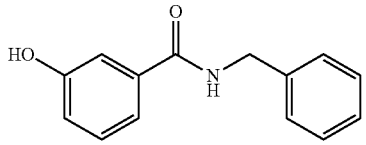 [SMILES: O=C(NCc1ccccc1)c1cccc(O)c1]

To a solution of 3-hydroxybenzoic acid (3.45 g, 25.00 mmol) in 100 mL of dichloromethane was added benzylamine (2.68 g, 25.00 mmol), followed by the addition of 1-ethyl-3-(3-dimethylaminopropyl)carbodiimide (7.20 g, 37.50 mmol). The mixture was stirred at room temperature for 24 h and the solvent was removed in vacuo. The residue was dissolved in 100 mL of ethyl acetate and washed with water. The organic layer was separated, concentrated and purified by column (1:1 to 1:2 hexane/ethyl acetate) to afford N-benzyl-3-hydroxybenzamide as a white solid in 60% yield (3.43 g). $^1$H NMR (300 MHz, CDCl$_3$): δ7.65-7.60 (m, 1H), 7.40-7.20 (m, 5H), 7.10-7.00 (m, 2H), 7.00 (m, 1H), 6.50-6.45 (m, 1H), 4.65 (d, J=5.7 Hz, 2H).

Preparation 13.1

Preparation of N-benzyl-2-(3-hydroxyphenyl)acetamide

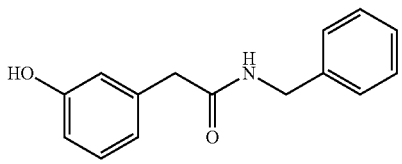 [SMILES: O=C(Cc1cccc(O)c1)NCc1ccccc1]

Following the procedure as described in Preparation 13, replacing 3-hydroxy-benzoic acid with 2-(3-hydroxyphenyl) acetic acid, N-benzyl-2-(3-hydroxyphenyl)-acetamide was obtained as a white solid in 30% yield. $^1$H NMR (300 MHz, CDCl$_3$): δ7.40-7.30 (m, 3H), 7.25-7.15 (m, 3H), 7.00-6.95 (m, 1H), 6.85-6.75 (m, 3H), 5.87 (br s, 1H), 4.42 (d, J=4.5 Hz, 2H), 3.56 (s, 2H).

Preparation 14

Preparation of 4-(trifluoromethyl)thiazole-2-thiol

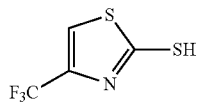

A 500 ml 3-necked round-bottomed flask was equipped with a gas dispersion tube, thermometer, connection to a hydrogen chloride scrubber unit and magnetic stirring bar. Carbon disulphide (8.75 g) and tetrahydrofuran (125 mL) were charged to the flask and the stirred contents cooled to 5-10° C. Ammonia (5.25 g) was bubbled into the reaction mixture at 5-10° C. over the course of 1.5 hours. After this time ammonia was seen to be bubbling through the scrubber solution indicating the end of the reaction. During the course of the reaction a yellow solid formed in the reaction flask. The reaction mixture was allowed to warm to room temperature over 30 minutes, the solid collected by filtration and washed with diethyl ether (2×70 mL). The yellow solid was placed in a Buchi flask and dried on a rotary evaporator at 40° C. to give the product ammonium dithiocarbamate as a pale yellow solid (10.5 g, 82.9% yield). This material was used without further purification. $^1$H NMR (400 MHz, DMSO-d$_6$): δ 7.45 (br s, 2H), 7.06 (br s, 4H).

1-Bromo-3,3,3-trifluoropropan-2-one (2.50 g, 22.68 mmol) in ter-butanol (10 mL) was treated with ammonium dithiocarbamate (1.45 g, 22.28 mmol). The mixture was stirred at ambient temperature for 18 hours, poured into water, extracted with ethyl acetate and the organic layer driedover magnesium sulfate and filtered. The filtrate was concentrated under reduced pressure and the residue purified by chromatography eluted with hexanes:ethyl acetate 17:3 to 7:3 by volume) to afford the hydrate (1.08 g). The hydrate was added to toluene (10 mL) containing p-toluene sulfonic acid (0.0025 g) and heated under reflux for 4 hours. The water was removed using Dean-Stark apparatus. The solution was cooled to ambient temperature, washed with water, dried over magnesium sulfate and filtered. The filtrate was concentrated under reduced pressure to afford 4-(trifluoromethyl)thiazole-2-thiol in 8% yield (355 mg). $^1$H NMR (400 MHz, CDCl$_3$): δ 7.10 (s, 1H).

Preparation 15

Preparation of 4-methylthiazole-2-thiol

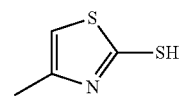

1-chloropropan-2-one (2.10 g, 22.68 mmol) in t-butanol (10 mL) was treated with ammonium dithiocarbamate (1.45 g, 22.28 mmol). The mixture was stirred at ambient temperature for 18 hours, poured into water, extracted with ethyl acetate and the organic layer dried over magnesium sulfate and filtered. The filtrate was evaporated under reduced pressure and the residue was purified by chromatography eluted with hexanes:ethyl acetate 17:3 to 7:3 by volume to afford 4-(trifluoromethyl)-thiazole-2-thiol in 52% yield (1.56 g). $^1$H NMR (400 MHz, CDCl$_3$): δ 6.22 (q, J=1.2 Hz, 1H), 2.22 (d, J=1.2 Hz, 3H).

Example 1

Synthesis of 4-(2-chloro-4-fluorophenoxy)-7-(2-(piperidin-1-yl)ethoxy)-5-((tetrahydro-2H-pyran-4-yl)oxy)quinazoline

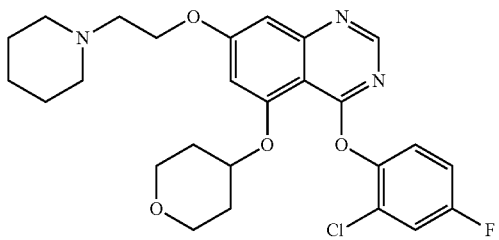 [SMILES: Fc1ccc(Oc2ncnc3cc(OCCN4CCCCC4)cc(OC4CCOCC4)c23)c(Cl)c1]

To a mixture of 4-chloro-7-(2-(piperidin-1-yl)ethoxy)-5-((tetrahydro-2H-pyran-4-yl)oxy)quinazoline (15 mg, 0.038 mmol) and 2-chloro-4-fluorophenol (12 µL, 0.12 mmol) in 0.5 mL of N,N-dimethylformamide was added sodium hydride (7.6 mg, 0.19 mmol). The mixture was heated at 100° C. for 2 h, and the solvent was removed in vacuo. The residue was purified by preparative thin layer chromatography developed with 0.5:5:94.5 NH$_4$OH:methanol:dichloromethane to afford the title compound as a white solid in 74% yield (14 mg). $^1$H NMR (300 MHz, CDCl$_3$): δ8.54 (s, 1H), 7.29-7.21 (m, 2H), 7.12-7.05 (m, 1H), 6.93 (d, J=2.4 Hz, 1H), 6.63 (d, J=2.4 Hz, 1H), 4.83-4.73 (m, 1H), 4.28 (t, J=6.3 Hz, 2H), 4.02-3.93 (m, 2H), 3.70-3.60 (m, 2H), 2.87 (t, J=6.3 Hz, 2H), 2.57 (m, 4H), 2.13-1.99 (m, 2H), 1.99-1.86 (m, 2H), 1.70-1.57 (m, 4H), 1.53-1.41 (m, 2H); MS (ES+): m/z 502.4 and 504.4 (M+1).

Example 2

Synthesis of 4-(2-chloro-4-fluorophenoxy)-7-(2-(1-methylpiperidin-4-yl)ethoxy)-5-((tetrahydro-2H-pyran-4-yl)oxy)quinazoline

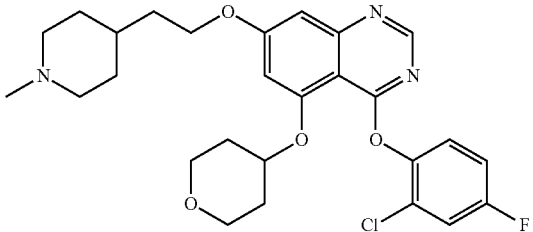 [SMILES: CN1CCC(CCOc2cc(OC3CCOCC3)c3c(Oc4ccc(F)cc4Cl)ncnc3c2)CC1]

To a solution of 7-(2-(1-methylpiperidin-4-yl)ethoxy)-5-((tetrahydro-2H-pyran-4-yl)oxy)quinazolin-4(3H)-one (0.16 g, 0.40 mmol) in 5 mL of 1,2-dichloroethane was added N,N-diisopropylethylamine (0.37 mL, 2.12 mmol) and POCl$_3$ (0.09 mL, 1.00 mmol). The mixture was refluxed for 2 h and the solvent and excess POCl$_3$ was removed in vacuo. The residue was dissolved in 5 mL of dichloroethane, followed by the addition of N,N-diisopropylethylamine (0.12 mL, 0.71 mmol) and 2-chloro-4-fluorophenol (0.06 g, 0.41 mmol). The mixture was refluxed overnight and the solvent was removed in vacuo. The residue was purified by column chromatography eluted with 0.5:5:94.5 NH$_4$OH:methanol:dichloromethane to afford the title compound as a white solid in 8% yield (13 mg). $^1$H NMR (300 MHz, CDCl$_3$): δ8.55 (s, 1H), 7.30-7.20 (m, 2H), 7.14-7.06 (m, 1H), 6.92 (d, J=2.4 Hz, 1H), 6.59 (d, J=2.4 Hz, 1H), 4.84-4.76 (m, 1H), 4.17 (t, J=6.5 Hz, 2H), 4.04-3.74 (m, 2H), 3.70-3.62 (m, 2H), 2.96-2.86 (m, 2H), 2.31 (s, 3H), 2.142.14-2.04 (m, 2H), 2.04-1.90 (m, 4H), 1.86-1.72 (m, 4H), 1.64-1.48 (m, 1H), 1.48-1.34 (m, 2H); MS (ES+): m/z 516.4 and 518.4 (M+1).

The compounds listed below were prepared following the procedure as described in Example 2.

Example 2.1

Synthesis of 4-(2-((4-(2-chloro-4-fluorophenoxy)-5-((tetrahydro-2H-pyran-4-yl)oxy)-quinazolin-7-yl)oxy)ethyl)morpholine

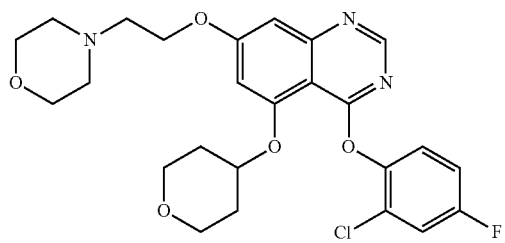 [SMILES: Fc1ccc(Oc2ncnc3cc(OCCN4CCOCC4)cc(OC4CCOCC4)c23)c(Cl)c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-morpholinoethoxy)-5-((tetrahydro-2H-pyran-4-yl)oxy)quinazolin-4(3H)-one to react with POCl$_3$ to generate the corresponding chloride then react with 2-chloro-4-fluorophenol, the title compound was obtained as a white solid in 37% yield. $^1$H NMR (300 MHz, CDCl$_3$): δ8.54 (s, 1H), 7.33-7.20 (m, 2H), 7.18-7.01 (m, 1H), 6.90 (d, J=2.3 Hz, 1H), 6.63 (d, J=2.3 Hz, 1H), 4.83-4.71 (m, 1H), 4.27 (t, J=5.7 Hz, 2H), 4.02-3.93 (m, 2H), 3.80-3.70 (m, 4H), 3.69-3.60 (m, 2H), 2.88 (t, J=5.7 Hz, 2H), 2.63-2.59 (m, 4H), 2.14-2.01 (m, 2H), 2.00-1.89 (m, 2H); MS (ES+): m/z 504.4 and 506.4 (M+1).

Example 2.2

Synthesis of 2-(2-((4-(2-chloro-4-fluorophenoxy)-5-((tetrahydro-2H-pyran-4-yl)oxy)quinazolin-7-yl)oxy)ethoxy)-N,N-dimethylethanamine

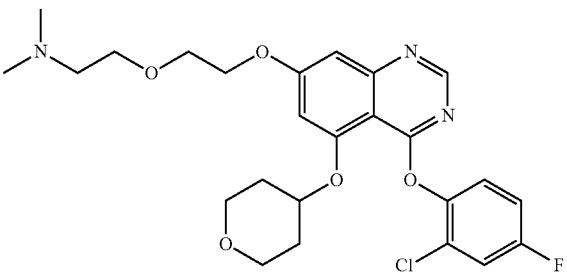 [SMILES: CN(C)CCOCCOc1cc(OC2CCOCC2)c2c(Oc3ccc(F)cc3Cl)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-

(2-(dimethylamino)ethoxy)ethoxy)-5-((tetrahydro-2H-pyran-4-yl)oxy)quinazolin-4(3H)-one to react with POCl₃ to generate the corresponding chloride then to react with 2-chloro-4-fluorophenol, the title compound was obtained as a white solid in 2% yield. ¹H NMR (300 MHz, CDCl₃): δ8.54 (s, 1H), 7.30-7.20 (m, 2H), 7.14-7.04 (m, 1H), 6.92 (d, J=2.3 Hz, 1H), 6.65 (d, J=2.3 Hz, 1H), 4.84-4.72 (m, 1H), 4.34-4.22 (m, 2H), 4.04-3.4 (m, 4H), 3.72-3.58 (m, 4H), 2.57 (t, J=5.8 Hz, 2H), 2.29 (s, 6H), 2.14-2.01 (m, 2H), 2.00-1.85 (m, 2H); MS (ES+): m/z 506.4 and 508.4 (M+1).

Example 2.3

Synthesis of 2-((4-(2-chloro-4-fluorophenoxy)-5-((tetrahydro-2H-pyran-4-yl)oxy)quinazolin-7-yl)oxy)-N-(2-methoxyethyl)-N-methylethanamine

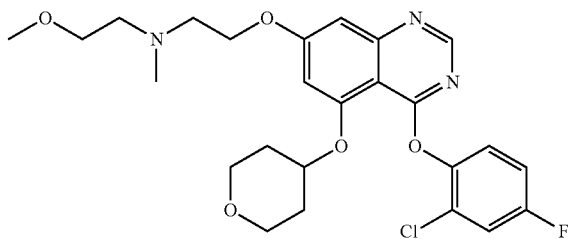 [SMILES: COCCN(C)CCOc1cc(OC2CCOCC2)c2c(Oc3ccc(F)cc3Cl)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-((2-methoxyethyl)(methyl)amino)ethoxy)-5-((tetrahydro-2H-pyran-4-yl)oxy)quinazolin-4(3H)-one to react with POCl₃ to generate the corresponding chloride then to react with 2-chloro-4-fluorophenol, the title compound was obtained as a white solid in 6% yield. ¹H NMR (300 MHz, CDCl₃): δ8.54 (s, 1H), 7.30-7.20 (m, 2H), 7.14-7.04 (m, 1H), 6.93 (d, J=2.2 Hz, 1H), 6.64 (d, J=2.2 Hz, 1H), 4.70-4.40 (m, 1H), 4.25 (t, J=5.7 Hz, 2H), 4.10-3.82 (m, 2H), 3.70-3.58 (m, 2H), 3.54 (t, J=5.7 Hz, 2H), 3.37 (s, 3H), 2.96 (t, J=5.7 Hz, 2H), 2.75 (t, J=5.7 Hz, 2H), 2.44 (s, 3H), 2.15-2.01 (m, 2H), 2.00-1.85 (m, 2H); MS (ES+): m/z 506.4 and 508.4 (M+1).

Example 2.4

Synthesis of 4-(2-chloro-4-fluorophenoxy)-7-(2-(2-methoxyethoxy)ethoxy)-5-((tetrahydro-2H-pyran-4-yl)oxy)quinazoline

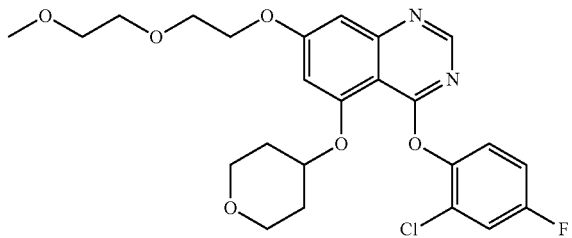 [SMILES: COCCOCCOc1cc(OC2CCOCC2)c2c(Oc3ccc(F)cc3Cl)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(2-methoxyethoxy)ethoxy)-5-((tetrahydro-2H-pyran-4-yl)oxy)quinazolin-4(3H)-one to react with POCl₃ to generate the corresponding chloride then to react with 2-chloro-4-fluorophenol, the title compound was obtained as a pale yellow solid in 15% yield. ¹H NMR (300 MHz, CDCl₃): δ8.53 (s, 1H), 7.30-7.20 (m, 2H), 7.13-7.03 (m, 1H), 6.91 (d, J=2.2 Hz, 1H), 6.65 (d, J=2.2 Hz, 1H), 4.83-4.66 (m, 1H), 4.32-4.25 (m, 2H), 4.02-3.90 (m, 4H), 3.76-3.70 (m, 2H), 3.69-3.55 (m, 4H), 3.40 (s, 3H), 2.15-1.81 (m, 4H); MS (ES+): m/z 515.3 and 517.3 (M+Na).

Example 2.5

Synthesis of 4-(3-((4-(2-chloro-4-fluorophenoxy)-5-((tetrahydro-2H-pyran-4-yl)oxy)quinazolin-7-yl)oxy)propyl)morpholine

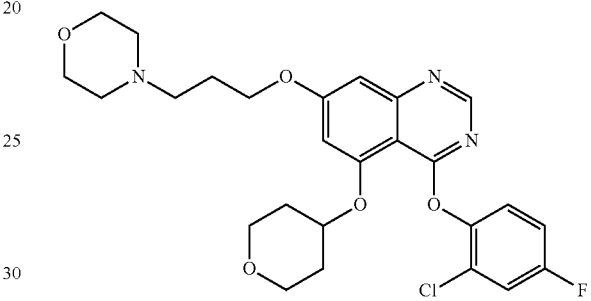

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)quinazolin-4(3H)-one to react with POCl₃ to generate the corresponding chloride then to react with 2-chloro-4-fluorophenol, the title compound was obtained as a pale yellow solid in 14% yield. ¹H NMR (300 MHz, CDCl₃): δ8.54 (s, 1H), 7.30-7.20 (m, 2H), 7.14-7.04 (m, 1H), 6.94 (d, J=2.2 Hz, 1H), 6.59 (d, J=2.2 Hz, 1H), 4.84-4.75 (m, 1H), 4.19 (t, J=6.5 Hz, 2H), 4.04-3.40 (m, 2H), 3.77-3.69 (m, 4H), 3.70-3.60 (m, 2H), 2.56 (t, J=6.5 Hz, 2H), 2.53-2.44 (m, 4H), 2.15-2.03 (m, 4H), 2.02-1.80 (m, 2H); MS (ES+): m/z 518.3 and 520.4 (M+1).

Example 2.6

Synthesis of 4-((1-methyl-1H-imidazol-2-yl)thio)-7-(2-(4-methylpiperazin-1-yl)ethoxy)-5-((tetrahydro-2H-pyran-4-yl)oxy)quinazoline

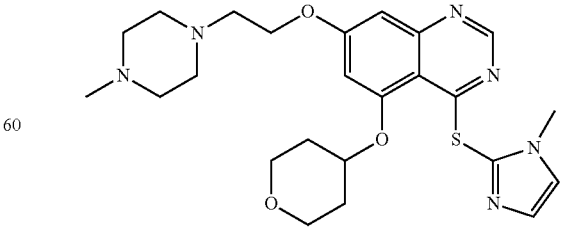

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl₃ to generate the corresponding chloride then to react with 1-methyl-1H-imidazole-2-thiol, the title compound was obtained as a white solid in 27% yield. ¹H NMR (300 MHz, CDCl₃): δ8.60 (s, 1H), 7.26 (d, J=2.1 Hz, 1H), 7.20 (d, J=2.1 Hz, 1H), 6.83 (d, J=2.3 Hz, 1H), 6.58 (d, J=2.3 Hz, 1H), 4.82-4.71 (m, 1H), 4.22 (t, J=5.8 Hz, 2H), 4.18-4.08 (m, 2H), 3.73-3.59 (m, 5H), 2.87 (t, J=5.8 Hz, 2H), 2.76-2.49 (m, 8H), 2.31 (s, 3H), 2.26-2.19 (m, 2H), 2.18-1.99 (m, 2H); MS (ES+): m/z 485.5 (M+1).

Example 2.7

Synthesis of 4-((1H-imidazol-2-yl)thio)-7-(2-(4-methylpiperazin-1-yl)ethoxy)-5-((tetrahydro-2H-pyran-4-yl)oxy)quinazoline

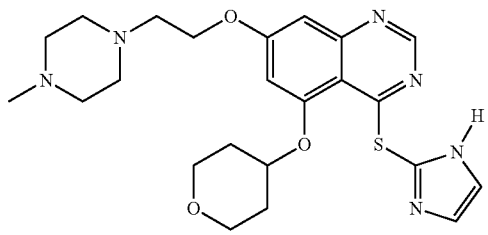 [SMILES: CN1CCN(CCOc2cc(OC3CCOCC3)c3c(Sc4ncc[nH]4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl₃ to generate the corresponding chloride then to react with 1H-imidazole-2-thiol, the title compound was obtained as a pale yellow solid in 4% yield. ¹H NMR (300 MHz, CDCl₃): δ9.13 (s, 1H), 7.04 (d, J=2.1 Hz, 1H), 6.96 (d, J=2.4 Hz, 1H), 6.84 (d, J=2.4 Hz, 1H), 6.62 (d, J=2.1 Hz, 1H), 4.60-4.43 (m, 1H), 4.30-4.28 (m, 2H), 3.95-3.80 (m, 2H), 3.55-3.40 (m, 2H), 2.90 (t, J=5.7 Hz, 2H), 2.70-2.56 (m, 4H), 2.55-2.42 (m, 4H), 2.32 (s, 3H), 2.15-1.90 (m, 2H), 1.60-1.45 (m, 2H); MS (ES+): m/z 471.5 (M+1).

Example 2.8

Synthesis of 7-(2-(4-methylpiperazin-1-yl)ethoxy)-4-((5-(pyridin-3-yl)-4H-1,2,4-triazol-3-yl)thio)-5-((tetrahydro-2H-pyran-4-yl)oxy)quinazoline

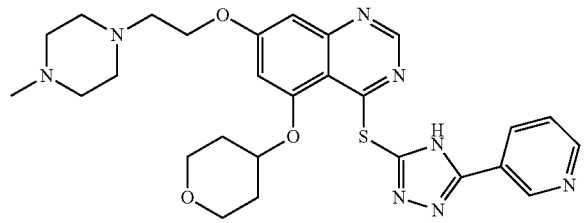 [SMILES: CN1CCN(CCOc2cc(OC3CCOCC3)c3c(Sc4nnc(-c5cccnc5)[nH]4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl₃ to generate the corresponding chloride then to react with 5-(pyridin-3-yl)-4H-1,2,4-triazole-3-thiol, the title compound was obtained as a yellow solid in 48% yield. ¹H NMR (300 MHz, CDCl₃): δ9.40 (d, J=2.1 Hz, 1H), 8.86 (s, 1H), 8.66 (dd, J=4.8, 2.1 Hz, 1H), 8.44-8.40 (m, 1H), 7.39 (dd, J=4.8, 2.1 Hz, 1H), 6.92 (d, J=2.1 Hz, 1H), 6.64 (d, J=2.1 Hz, 1H), 4.85-4.70 (m, 1H), 4.27 (t, J=5.4 Hz, 2H), 4.20-4.10 (m, 2H), 3.74-3.60 (m, 2H), 2.90 (t, J=5.4 Hz, 2H), 2.78-2.40 (m, 8H), 2.31 (s, 3H), 2.30-2.27 (m, 2H), 2.20-2.05 (m, 2H); MS (ES+): m/z 549.5 (M+1).

Example 2.9

Synthesis of (S)-4-(2-chloro-4-fluorophenoxy)-7-((2,2-dimethyl-1,3-dioxolan-4-yl)methoxy)-5-((tetrahydro-2H-pyran-4-yl)oxy)quinazoline

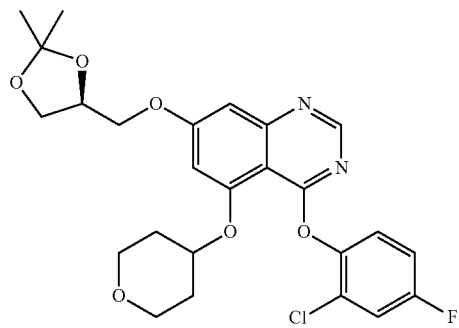 [SMILES: CC1(C)OC[C@H](COc2cc(OC3CCOCC3)c3c(Oc4ccc(F)cc4Cl)ncnc3c2)O1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with (S)-7-((2,2-dimethyl-1,3-dioxolan-4-yl)methoxy)-5-((tetrahydro-2H-pyran-4-yl)oxy)-quinazolin-4(3H)-one to react with POCl₃ to generate the corresponding chloride then to react with 2-chloro-4-fluorophenol, the title compound was obtained as a yellow foamy solid in 15% yield. ¹H NMR (300 MHz, CDCl₃): δ8.55 (s, 1H), 7.32-7.18 (m, 2H), 7.15-7.04 (m, 1H), 6.92 (d, J=2.3 Hz, 1H), 6.65 (d, J=2.3 Hz, 1H), 4.93-4.78 (m, 1H), 4.60-4.55 (m, 1H), 4.25-4.07 (m, 3H), 4.04-3.87 (m, 3H), 3.70-3.58 (m, 2H), 2.15-2.02 (m, 2H), 2.01-1.88 (m, 2H), 1.49 (s, 3H), 1.43 (s, 3H); MS (ES+): m/z 505.4 and 507.4 (M+1).

Example 2.10

Synthesis of 4-(2-chloro-4-fluorophenoxy)-7-(4-(2-methoxyethyl)piperazin-1-yl)-5-((tetrahydro-2H-pyran-4-yl)oxy)quinazoline

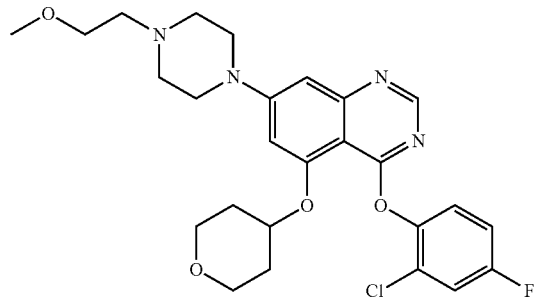 [SMILES: COCCN1CCN(c2cc(OC3CCOCC3)c3c(Oc4ccc(F)cc4Cl)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(4-

(2-methoxyethyl)piperazin-1-yl)-5-((tetrahydro-2H-pyran-4-yl)oxy)quinazolin-4(3H)-one to react with POCl₃ to generate the corresponding chloride then to react with 2-chloro-4-fluorophenol, the title compound was obtained as a yellow foamy solid in 15% yield. ¹H NMR (300 MHz, CDCl₃): δ 8.47 (s, 1H), 7.28-7.19 (m, 2H), 7.13-7.03 (m, 1H), 6.87 (d, J=2.3 Hz, 1H), 6.63 (d, J=2.3 Hz, 1H), 4.84-4.72 (m, 1H), 4.05-3.93 (m, 2H), 3.65-3.55 (m, 4H), 3.54-3.43 (m, 4H), 3.39 (s, 3H), 2.78-2.64 (m, 6H), 2.13-2.00 (m, 2H), 1.99-1.88 (m, 2H); MS (ES+): m/z 517.4 and 519.4 (M+1).

Example 2.11

Synthesis of 4,5-dimethyl-2-((7-(2-(4-methylpiperazin-1-yl)ethoxy)-5-((tetrahydro-2H-pyran-4-yl)oxy)quinazolin-4-yl)thio)oxazole

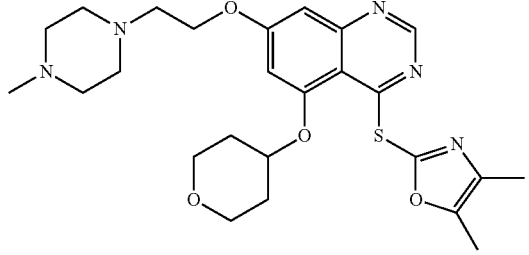

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl₃ to generate the corresponding chloride then to react with 4,5-dimethyloxazole-2-thiol, the title compound was obtained as a yellow solid in 31% yield. ¹H NMR (300 MHz, CDCl₃): δ 8.66 (s, 1H), 8.84 (d, J=2.1 Hz, 1H), 6.57 (d, J=2.1 Hz, 1H), 4.83-4.69 (m, 1H), 4.23 (t, J=5.7 Hz, 2H), 4.18-4.07 (m, 2H), 3.72-3.60 (m, 2H), 2.90 (t, J=5.7 Hz, 2H), 2.82-2.53 (m, 8H), 2.41 (s, 3H), 2.36 (s, 3H), 2.24-2.18 (m, 5H), 2.17-1.98 (m, 2H). MS (ES+): m/z 500.5 (M+1).

Example 2.12

Synthesis of 4-(2-chloro-4-fluorophenoxy)-5-methoxy-7-(2-(4-methylpiperazin-1-yl)ethoxy)quinazoline

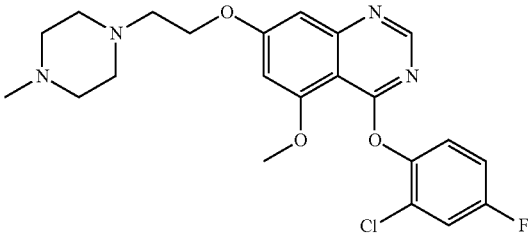 [SMILES: COc1cc(OCCN2CCN(C)CC2)cc2ncnc(Oc3ccc(F)cc3Cl)c12]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(2-(4-methylpiperazin-1-yl)ethoxy)-quinazolin-4(3H)-one to react with POCl₃ to generate the corresponding chloride then to react with 2-chloro-4-fluorophenol, the title compound was obtained as a white solid in 22% yield. ¹H NMR (300 MHz, CDCl₃): δ 8.54 (s, 1H), 7.32-7.24 (m, 2H), 7.15-7.05 (m, 1H), 6.92 (d, J=1.8 Hz, 1H), 6.62 (d, J=1.8 Hz, 1H), 4.27 (t, J=4.0 Hz, 2H), 4.00 (s, 3H), 2.95 (t, J=4.0 Hz, 2H), 2.92-2.74 (m, 8H), 2.52 (s, 3H); MS (ES+): m/z 447.4 and 449.4 (M+1).

Example 2.13

Synthesis of N-(5-methoxy-7-((1-methylpiperidin-4-yl)methoxy)quinazolin-4-yl)-4-(trifluoromethyl)thiazol-2-amine

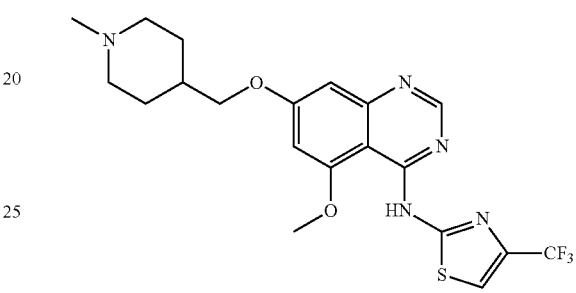

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-((1-methylpiperidin-4-yl)methoxy)quinazolin-4(3H)-one to react with POCl₃ to generate the corresponding chloride then to react with 2-amino-4-trifluoromethylthiazole, the title compound was obtained as a white solid in 13% yield. ¹H NMR (300 MHz, CDCl₃): δ 8.77 (s, 1H), 7.42 (s, 1H), 6.90 (d, J=2.2 Hz, 1H), 6.59 (d, J=2.2 Hz, 1H), 4.14 (s, 3H), 3.99 (d, J=5.8 Hz, 2H), 3.08-2.91 (m, 2H), 2.37 (s, 3H), 2.17-1.96 (m, 2H), 1.95-1.78 (m, 3H), 1.68-1.49 (m, 2H); MS (ES+): m/z 454.5 (M+1).

Example 2.14

Synthesis of N-(7-(2-(4-methylpiperazin-1-yl)ethoxy)-5-((tetrahydro-2H-pyran-4-yl)oxy)quinazolin-4-yl)thiazol-2-amine

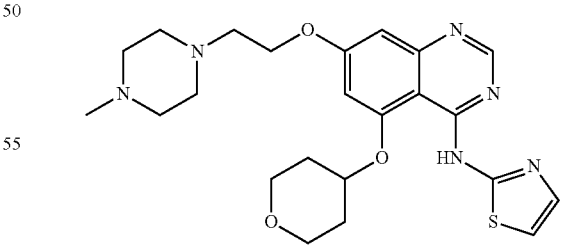

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy]-5-((tetrahydro-2H-pyran-4-yl)oxy)quinazolin-4(3H)-one to react with POCl₃ to generate the corresponding chloride then to react with 2-aminothiazole, the title compound was obtained as a white solid in 14% yield. $^1$H NMR (300 MHz, CDCl$_3$): δ8.75 (s, 1H), 7.52 (d, J=3.7 Hz, 1H), 7.01 (d, J=3.7 Hz, 1H), 6.89 (d, J=2.2 Hz, 1H), 6.61 (d, J=2.2 Hz, 1H), 4.87-4.78 (m, 1H), 4.24 (t, J=5.9 Hz, 2H), 4.18-4.09 (m, 2H), 3.75-3.65 (m, 2H), 2.88 (t, J=5.9 Hz, 2H), 2.72-2.43 (m, 8H), 2.31 (s, 3H), 2.30-2.17 (m, 2H), 2.16-2.02 (m, 2H); MS (ES+): m/z 471.5 (M+1).

Example 2.15

Synthesis of N$^1$-(2-((4-(2-chloro-4-fluorophenoxy)-5-((tetrahydro-2H-pyran-4-yl)oxy)quinazolin-7-yl)oxy)ethyl)-N$^1$,N$^2$,N$^2$-trimethylethane-1,2-diamine

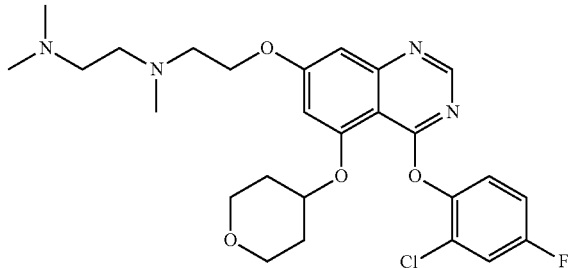 [SMILES: CN(C)CCN(C)CCOc1cc(OC2CCOCC2)c2c(Oc3ccc(F)cc3Cl)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-((2-(dimethylamino)ethyl)(methyl)amino)ethoxy)-5-((tetrahydro-2H-pyran-4-yl)oxy)-quinazolin-4(3H)-one to react with POCl$_3$ to generate the corresponding chloride then to react with 2-chloro-4-fluorophenol, the title compound was obtained as a white solid in 18% yield. $^1$H NMR (300 MHz, CDCl$_3$): δ8.54 (s, 1H), 7.32-7.20 (m, 2H), 7.14-7.04 (m, 1H), 6.93 (d, J=2.1 Hz, 1H), 6.64 (d, J=2.1 Hz, 1H), 4.84-4.74 (m, 1H), 4.23 (t, J=5.7 Hz, 2H), 4.04-3.92 (m, 2H), 3.70-3.58 (m, 2H), 2.92 (t, J=5.7 Hz, 2H), 2.64 (t, J=6.6 Hz, 2H), 2.47 (t, J=6.6 Hz, 2H), 2.40 (s, 3H), 2.28 (s, 6H), 2.14-2.02 (m, 2H), 2.01-1.88 (m, 2H); MS (ES+): m/z 519.4 and 521.4 (M+1).

Example 2.16

Synthesis of 2-(2-((4-methoxy-5-((tetrahydro-2H-pyran-4-yl)oxy)quinazolin-7-yl)oxy)ethoxy)-N,N-dimethylethanamine

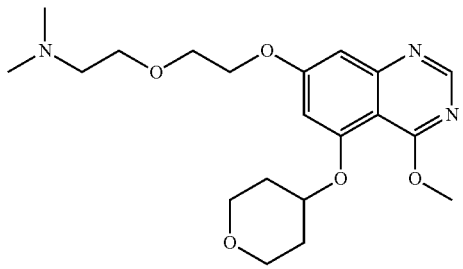

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(2-(dimethylamino)ethoxy)ethoxy)-5-((tetrahydro-2H-pyran-4-yl)oxy)quinazolin-4(3H)-one to react with POCl$_3$ to generate the corresponding chloride then to react with methanol, the title compound was obtained as a pale yellow solid in 31% yield. $^1$H NMR (300 MHz, CDCl$_3$): δ8.62 (s, 1H), 6.85 (d, J=2.0 Hz, 1H), 6.57 (d, J=2.0 Hz, 1H), 4.70-4.65 (m, 1H), 4.27-4.21 (m, 2H), 4.12 (s, 3H), 4.06-3.97 (m, 2H), 3.90-3.84 (m, 2H), 3.72-3.62 (m, 4H), 2.56 (t, J=5.8 Hz, 2H), 2.29 (s, 6H), 2.13-2.01 (m, 2H), 2.00-1.83 (m, 2H).

Example 2.17

Synthesis of 4-(3-((4-(2-chloro-4-fluorophenoxy)-5-methoxyquinazolin-7-yl)oxy)propyl)morpholine

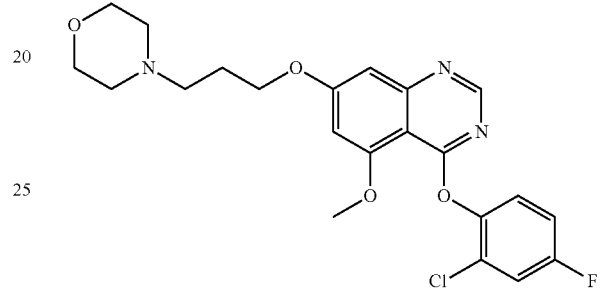

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(3-morpholin-4-yl-propoxy)-3H-quinazolin-4-one to react with POCl$_3$ to generate the corresponding chloride then to react with 2-chloro-4-fluorophenol, the title compound was obtained as a white solid in 8% yield. $^1$H NMR (300 MHz, CDCl$_3$): δ8.54 (s, 1H), 7.30-7.22 (m, 2H), 7.11-7.05 (m, 1H), 6.94 (d, J=2.2 Hz, 1H), 6.60 (d, J=2.2 Hz, 1H), 4.20 (t, J=6.7 Hz, 2H), 3.99 (s, 3H), 3.78-3.70 (m, 4H), 2.57 (t, J=7.1 Hz, 2H), 2.52-2.45 (m, 4H), 2.10-2.01 (m, 2H); MS (ES+): m/z 447.1 and 449.1 (M+1).

Example 2.18

Synthesis of N-(7-(3-morpholinopropoxy)-5-((tetrahydro-2H-pyran-4-yl)oxy)quinazolin-4-yl)-4-(trifluoromethyl)thiazol-2-amine

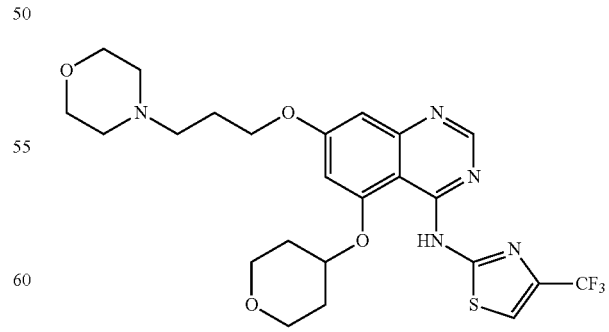

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)

quinazolin-4(3H)-one to react with POCl₃ to generate the corresponding chloride then to react with 4-trifluoromethylthiazol-2-ylamine, the title compound was obtained as a white solid in 5% yield. ¹H NMR (300 MHz, CDCl₃): δ8.80 (s, 1H), 7.45 (s, 1H), 6.97 (d, J=2.1 Hz, 1H), 6.62 (d, J=2.1 Hz, 1H), 4.94-4.83 (m, 1H), 4.28-4.13 (m, 4H), 3.86-3.70 (m, 6H), 2.66-2.50 (m, 6H), 2.38-2.26 (m, 2H), 2.20-2.04 (m, 4H); MS (ES+): m/z 540.2 (M+1).

Example 2.19

Synthesis of N-(7-(3-morpholinopropoxy)-5-((tetrahydro-2H-pyran-4-yl)oxy)quinazolin-4-yl)-1,3,4-thiadiazol-2-amine

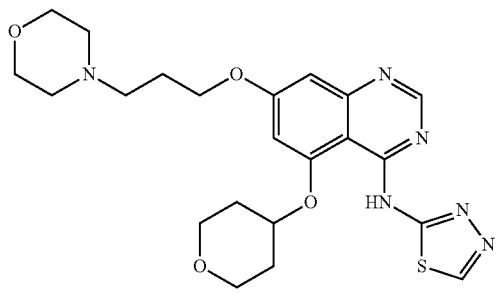 [SMILES: c1nc(Nc2nncs2)c2c(OC3CCOCC3)cc(OCCCN3CCOCC3)cc2n1]

Following the procedure as described in Example 2, replacing 7-(2-(1-methylpiperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)quinazolin-4(3H)-one to react with POCl₃ to generate the corresponding chloride then to react with 1,3,4-thiadiazol-2-amine, the title compound was obtained as a colourless oil in 4% yield. ¹H NMR (300 MHz, CDCl₃): δ8.86 (s, 1H), 8.75 (s, 1H), 6.94 (d, J=2.1 Hz, 1H), 6.60 (d, J=2.1 Hz, 1H), 4.90-4.79 (m, 1H), 4.25-4.10 (m, 4H), 3.80-3.67 (m, 6H), 2.62-2.45 (m, 6H), 2.38-2.25 (m, 2H), 2.20-2.02 (m, 4H); MS (ES+): m/z 473.5 (M+1).

Example 2.20

Synthesis of 5-methyl-N-(7-(3-morpholinopropoxy)-5-((tetrahydro-2H-pyran-4-yl)oxy)quinazolin-4-yl)-1,3,4-thiadiazol-2-amine

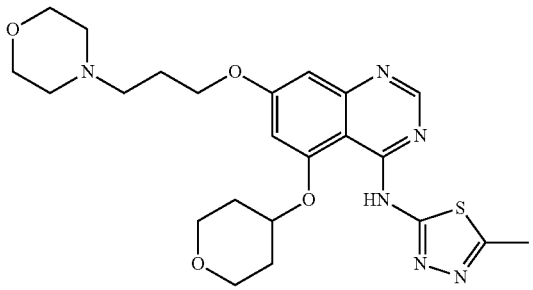 [SMILES: Cc1nnc(Nc2ncnc3cc(OCCCN4CCOCC4)cc(OC4CCOCC4)c23)s1]

Following the procedure as described in Example 2, replacing 7-(2-(1-methylpiperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)

quinazolin-4(3H)-one to react with POCl₃ to generate the corresponding chloride then to react with 5-methyl-(1,3,4)-thiadiazol-2-amine, the title compound was obtained as a colourless oil in 6% yield. ¹H NMR (300 MHz, CDCl₃): δ8.69 (s, 1H), 6.92 (d, J=2.1 Hz, 1H), 6.57 (d, J=2.1 Hz, 1H), 4.88-4.77 (m, 1H), 4.22-4.06 (m, 4H), 3.80-3.65 (m, 6H), 2.72 (s, 3H), 2.60-2.40 (m, 6H), 2.34-2.22 (m, 2H), 2.17-1.98 (m, 4H); MS (ES+): m/z 487.4 (M+1).

Example 2.21

Synthesis of N-(7-(3-morpholinopropoxy)-5-((tetrahydro-2H-pyran-4-yl)oxy)quinazolin-4-yl)thiazol-2-amine

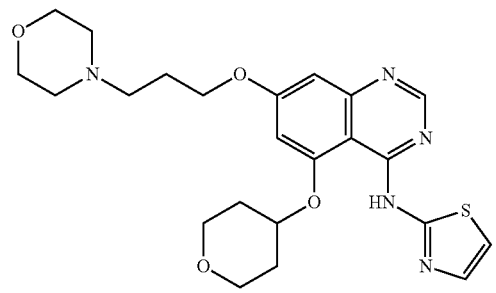 [SMILES: c1csc(Nc2ncnc3cc(OCCCN4CCOCC4)cc(OC4CCOCC4)c23)n1]

Following the procedure as described in Example 2, replacing 7-(2-(1-methylpiperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)quinazolin-4(3H)-one to react with POCl₃ to generate the corresponding chloride then to react with thiazol-2-amine, the title compound was obtained as a white solid in 5% yield. ¹H NMR (300 MHz, CDCl₃): δ8.79 (s, 1H), 7.56 (d, J=3.6 Hz, 1H), 7.06 (d, J=3.6 Hz, 1H), 6.95 (d, J=2.1 Hz, 1H), 6.61 (d, J=2.1 Hz, 1H), 4.92-4.82 (m, 1H), 4.26-4.13 (m, 4H), 3.82-3.70 (m, 6H), 2.64-2.48 (m, 6H), 2.38-2.26 (m, 2H), 2.20-2.02 (m, 4H); MS (ES+): m/z 472.5 (M+1).

Example 2.22

Synthesis of N-(7-(3-morpholinopropoxy)-5-((tetrahydro-2H-pyran-4-yl)oxy)quinazolin-4-yl)-5-(trifluoromethyl)-1,3,4-thiadiazol-2-amine

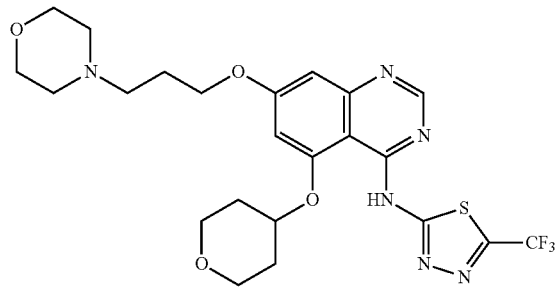 [SMILES: FC(F)(F)c1nnc(Nc2ncnc3cc(OCCCN4CCOCC4)cc(OC4CCOCC4)c23)s1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)

quinazolin-4(3H)-one to react with POCl$_3$ to generate the corresponding chloride then to react with 5-(trifluoromethyl)-1,3,4-thiadiazol-2-amine, the title compound was obtained as a white solid in 17% yield. $^1$H NMR (300 MHz, CDCl$_3$): δ8.78 (s, 1H), 6.97 (d, J=2.1 Hz, 1H), 6.63 (d, J=2.1 Hz, 1H), 4.93-4.82 (m, 1H), 4.25-4.18 (m, 4H), 3.80-3.68 (m, 6H), 2.66-2.50 (m, 6H), 2.38-2.25 (m, 2H), 2.20-2.00 (m, 4H); MS (ES+): m/z 541.4 (M+1).

Example 2.23

Synthesis of N-(7-((1-methylpiperidin-4-yl)methoxy)-5-((tetrahydro-2H-pyran-4-yl)oxy)quinazolin-4-yl)-4-(trifluoromethyl)thiazol-2-amine

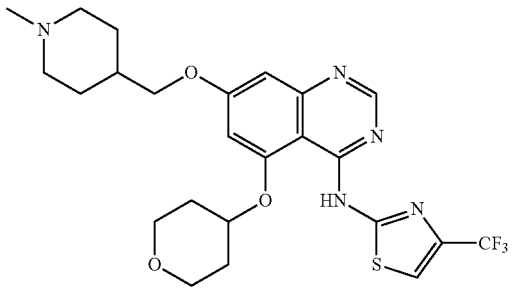 [SMILES: CN1CCC(COc2cc(OC3CCOCC3)c3c(Nc4nc(C(F)(F)F)cs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl$_3$ to generate the corresponding chloride then to react with 4-(trifluoromethyl)thiazol-2-amine, the title compound was obtained as a white solid in 23% yield. $^1$H NMR (300 MHz, CDCl$_3$): δ8.76 (s, 1H), 7.40 (s, 1H), 6.90 (d, J=1.8 Hz, 1H), 6.59 (d, J=1.8 Hz, 1H), 4.88-4.78 (m, 1H), 4.20-4.10 (m, 2H), 3.97 (d, J=5.7 Hz, 2H), 3.77-3.66 (m, 2H), 3.00-2.88 (m, 2H), 2.40-2.22 (m, 5H), 2.18-1.95 (m, 5H), 1.95-1.80 (m, 2H), 1.65-1.45 (m, 2H); MS (ES+): m/z 524.4 (M+1).

Example 2.24

Synthesis of N-(5-methoxy-7-morpholinoquinazolin-4-yl)-4-(trifluoromethyl)thiazol-2-amine

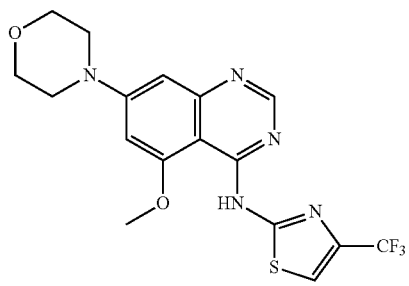 [SMILES: COc1cc(N2CCOCC2)cc2ncnc(Nc3nc(C(F)(F)F)cs3)c12]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-morpholinoquinazolin-4(3H)-one to react with POCl$_3$ to generate the corresponding chloride then to react with 4-(trifluoromethyl)-thiazol-2-amine, the title compound was obtained as a white solid in 3% yield. $^1$H NMR (300 MHz, CDCl$_3$): δ10.80 (s, 1H), 8.71 (s, 1H), 7.41 (s, 1H), 6.85 (d, J=1.8 Hz, 1H), 6.57 (d, J=1.8 Hz, 1H), 4.15 (s, 3H), 3.93-3.87 (m, 4H), 3.43-3.36 (m, 4H); MS (ES+): m/z 413.4 (M+1).

Example 2.25

Synthesis of N-(5-methoxy-7-(4-methylpiperazin-1-yl)quinazolin-4-yl)-4-(trifluoromethyl)thiazol-2-amine

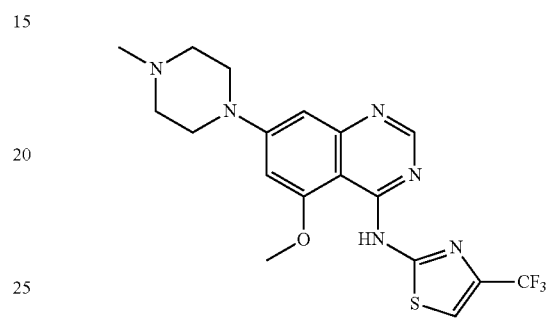

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-morpholinoquinazolin-4(3H)-one to react with POCl$_3$ to generate the corresponding chloride then to react with 4-(trifluoromethyl)-thiazol-2-amine, the title compound was obtained as a yellowish solid in 18% yield. $^1$H NMR (300 MHz, CDCl$_3$): δ10.83 (s, 1H), 8.74 (s, 1H), 7.45 (s, 1H), 6.90 (d, J=2.4 Hz, 1H), 6.63 (d, J=1.8 Hz, 1H), 4.19 (s, 3H), 3.60-3.48 (m, 4H), 2.78-2.60 (m, 4H), 2.46 (s, 3H); MS (ES+): m/z 425.3 (M+1).

Example 2.26

Synthesis of methyl 3-((5-methoxy-7-(3-morpholinopropoxy)quinazolin-4-yl)oxy)benzoate

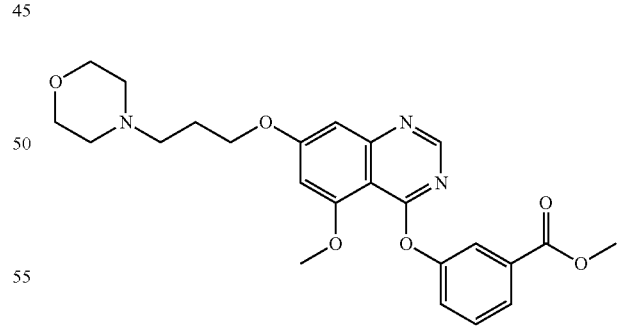

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(3-morpholinopropoxy)quinazolin-4(3H)-one to react with POCl$_3$ to generate the corresponding chloride then to react with methyl 3-hydroxybenzoate, the title compound was obtained as a gummy solid in 5% yield. $^1$H NMR (300 MHz, CDCl$_3$): δ8.55 (s, 1H), 8.00-7.95 (m, 1H), 7.90-7.85 (m, 1H), 7.55-7.50 (m, 1H), 7.45-7.40 (m, 1H), 6.94 (d, J=2.1 Hz, 1H), 6.59 (d, J=2.1 Hz, 1H), 4.25-4.15 (m, 2H), 3.98 (s, 3H), 3.90 (s, 3H), 3.80-3.70 (m, 4H), 2.60-2.45 (m, 6H), 2.15-2.05 (m, 2H); MS (ES+): m/z 454.2 (M+1).

Example 2.27

Synthesis of methyl 2-(3-((5-methoxy-7-(3-morpholinopropoxy)quinazolin-4-yl)oxy)phenyl)acetate

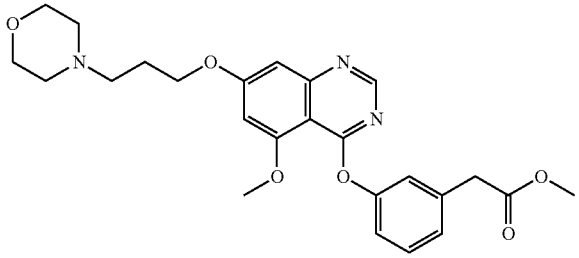 [SMILES: COC(=O)Cc1cccc(Oc2ncnc3cc(OCCCN4CCOCC4)cc(OC)c23)c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(3-morpholinopropoxy)quinazolin-4(3H)-one to react with methyl 2-(3-hydroxyphenyl)acetate, the title compound was obtained as a gummy solid in 16% yield. $^1$H NMR (300 MHz, CDCl$_3$): δ8.56 (s, 1H), 7.45-7.40 (m, 1H), 7.22-7.12 (m, 3H), 6.93 (d, J=2.1 Hz, 1H), 6.58 (d, J=2.1 Hz, 1H), 4.25-4.15 (m, 2H), 3.98 (s, 3H), 3.80-3.75 (m, 4H), 3.70 (s, 3H), 3.68 (s, 2H), 2.60-2.45 (m, 6H), 2.10-2.00 (m, 2H); MS (ES+): m/z 468.2 (M+1).

Example 2.28

Synthesis of N-benzyl-3-((5-methoxy-7-(3-morpholinopropoxy)quinazolin-4-yl)oxy)benzamide

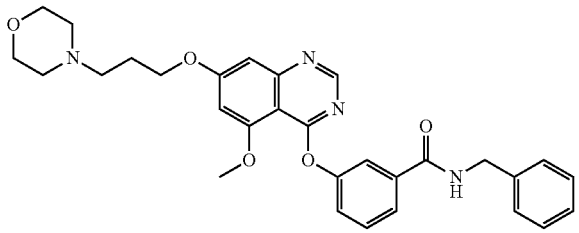 [SMILES: COc1cc(OCCCN2CCOCC2)cc2ncnc(Oc3cccc(C(=O)NCc4ccccc4)c3)c12]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(3-morpholinopropoxy)quinazolin-4(3H)-one to react with POCl$_3$ to generate the corresponding chloride then to react with N-benzyl-3-hydroxybenzamide, the title compound was obtained as a gummy solid in 23% yield. $^1$H NMR (300 MHz, CDCl$_3$): δ8.54 (s, 1H), 7.75-7.70 (m, 1H), 7.65-7.60 (m, 1H), 7.55-7.50 (m, 1H), 7.40-7.35 (m, 5H), 7.35-7.30 (m, 1H), 6.93 (d, J=2.1 Hz, 1H), 6.58 (d, J=2.1 Hz, 1H), 6.45-6.40 (m, 1H), 4.66 (d, J=5.6 Hz, 2H), 4.25-4.35 (m, 2H), 3.98 (s, 3H), 3.75-3.70 (m, 4H), 2.60-2.55 (m, 2H), 2.55-2.45 (m, 4H), 2.10-2.05 (m, 2H); MS (ES+): m/z 529.5 (M+1).

Example 2.29

Synthesis of N-benzyl-2-(3-((5-methoxy-7-(3-morpholinopropoxy)quinazolin-4-yl)oxy)phenyl)acetamide

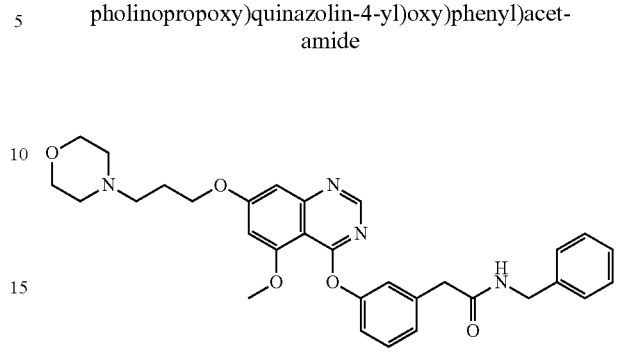

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-(3-morpholinopropoxy)quinazolin-4(3H)-one to react with POCl$_3$ to generate the corresponding chloride then to react with N-benzyl-2-(3-hydroxyphenyl)acetamide, the title compound was obtained as a gummy solid in 32% yield. $^1$H NMR (300 MHz, CDCl$_3$): δ8.42 (s, 1H), 7.50-7.40 (m, 1H), 7.60-7.30 (m, 8H), 6.92 (d, J=2.1 Hz, 1H), 6.58 (d, J=2.1 Hz, 1H), 5.85-5.80 (m, 1H), 4.44 (d, J=5.4 Hz, 2H), 4.25-4.20 (m, 2H), 3.97 (s, 3H), 3.75-3.70 (m, 4H), 3.68 (s, 2H), 2.60-2.55 (m, 2H), 2.50-2.45 (m, 4H), 2.10-2.00 (m, 2H); MS (ES+): m/z 543.5 (M+1).

Example 2.30

Synthesis of methyl 3-((7-(2-(4-methylpiperazin-1-yl)ethoxy)-5-((tetrahydro-2H-pyran-4-yl)oxy)quinazolin-4-yl)oxy)benzoate

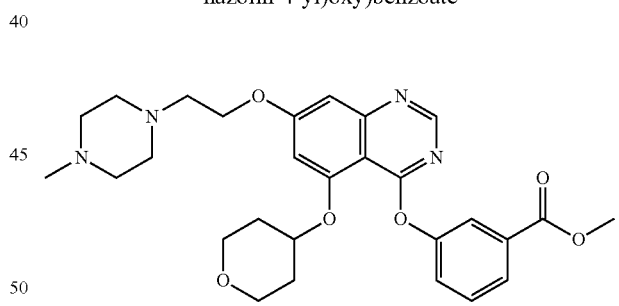

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl$_3$ to generate the corresponding chloride then to react with methyl 3-hydroxybenzoate, the title compound was obtained as a gummy solid in 16% yield. $^1$H NMR (300 MHz, CDCl$_3$): δ8.56 (s, 1H), 8.05-7.95 (m, 1H), 7.90-7.85 (m, 1H), 7.60-7.50 (m, 1H), 7.45-7.40 (m, 1H), 6.93 (d, J=2.1 Hz, 1H), 6.59 (d, J=2.1 Hz, 1H), 4.80-4.70 (m, 1H), 4.30-4.20 (m, 2H), 4.00-3.90 (m, 5H), 3.70-3.60 (m, 2H), 2.95-2.85 (m, 2H), 2.75-2.60 (m, 4H), 2.60-2.45 (m, 4H), 2.34 (s, 3H), 2.15-2.00 (m, 2H), 2.00-1.90 (m, 2H) MS (ES+): m/z 523.4 (M+1).

Example 2.31

Synthesis of methyl 2-(3-((7-(2-(4-methylpiperazin-1-yl)ethoxy)-5-((tetrahydro-2H-pyran-4-yl)oxy)quinazolin-4-yl)oxy)phenyl)acetate

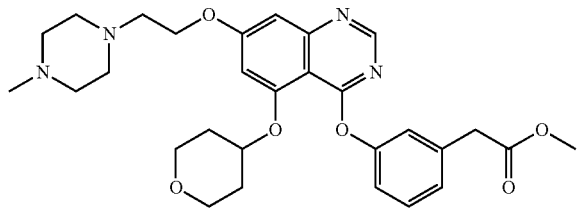

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl$_3$ to generate the corresponding chloride then to react with methyl 2-(3-hydroxyphenyl)acetate, the title compound was obtained as a gummy solid in 5% yield. $^1$H NMR (300 MHz, CDCl$_3$): δ8.57 (s, 1H), 7.45-7.40 (m, 1H), 7.22-7.12 (m, 3H), 6.91 (d, J=2.1 Hz, 1H), 6.61 (d, J=2.1 Hz, 1H), 4.75-4.70 (m, 1H), 4.25-4.15 (m, 2H), 3.95-3.85 (m, 2H), 3.70-3.60 (m, 7H), 2.95-2.85 (m, 2H), 2.80-2.70 (m, 8H), 2.50 (s, 3H), 2.15-2.10 (m, 2H), 2.05-1.95 (m, 2H); MS (ES+): m/z 537.5 (M+1).

Example 2.32

Synthesis of N-benzyl-3-((7-(2-(4-methylpiperazin-1-yl)ethoxy)-5-((tetrahydro-2H-pyran-4-yl)oxy)quinazolin-4-yl)oxy)benzamide

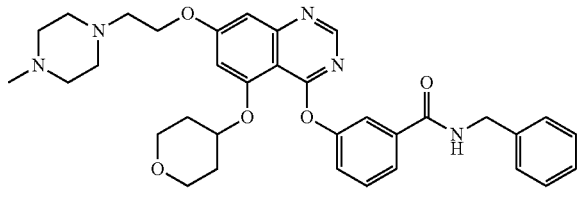 [SMILES: CN1CCN(CCOc2cc(OC3CCOCC3)c3c(Oc4cccc(C(=O)NCc5ccccc5)c4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl$_3$ to generate the corresponding chloride then to react with N-benzyl-3-hydroxybenzamide, the title compound was obtained as a gummy solid in 12% yield. $^1$H NMR (300 MHz, CDCl$_3$): δ 8.54 (s, 1H), 7.75-7.65 (m, 2H), 7.55-7.45 (m, 1H), 7.38-7.30 (m, 5H), 7.25-7.15 (m, 1H), 6.92 (d, J=2.4 Hz, 1H), 6.62 (d, J=2.4 Hz, 1H), 6.50-6.40 (m, 1H), 4.80-4.70 (m, 1H), 4.66 (d, J=5.6 Hz, 2H), 4.30-4.20 (m, 2H), 4.05-3.95 (m, 2H), 3.70-3.60 (m, 2H), 2.95-2.85 (m, 2H), 2.70-2.60 (m, 4H), 2.60-2.45 (m, 4H), 2.31 (s, 3H), 2.15-2.00 (m, 2H), 2.00-1.90 (m, 2H); MS (ES+): m/z 598.5 (M+1).

Example 2.33

Synthesis of N-benzyl-2-(3-((7-(2-(4-methylpiperazin-1-yl)ethoxy)-5-((tetrahydro-2H-pyran-4-yl)oxy)quinazolin-4-yl)oxy)phenyl)acetamide

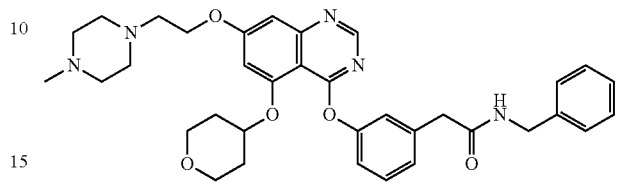

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(4-methylpiperazin-1-yl)ethoxy)-5-((tetrahydro-2H-pyran-4-yl)oxy)quinazolin-4(3H)-one to react with POCl$_3$ to generate the corresponding chloride then to react with N-benzyl-2-(3-hydroxyphenyl)acetamide, the title compound was obtained as a gummy solid in 14% yield. $^1$H NMR (300 MHz, CDCl$_3$): 8.41 (s, 1H), 7.50-7.40 (m, 1H), 7.40-7.10 (m, 8H), 6.92 (d, J=2.4 Hz, 1H), 6.62 (d, J=2.4 Hz, 1H), 5.85-5.80 (m, 1H), 4.80-4.70 (m, 1H), 4.45 (d, J=5.6 Hz, 2H), 4.30-4.20 (m, 2H), 4.00-3.90 (m, 2H), 3.69 (s, 2H), 3.68-3.60 (m, 2H), 2.95-2.85 (m, 2H), 2.75-2.60 (m, 4H), 2.60-2.45 (m, 4H), 2.34 (s, 3H), 2.10-2.00 (m, 2H), 2.00-1.90 (m, 2H); MS (ES+): m/z 612.5 (M+1).

Example 2.34

Synthesis of 4-(2-chloro-4-fluorophenoxy)-5-methoxy-7-((1-methylpiperidin-4-yl)methoxy)quinazoline

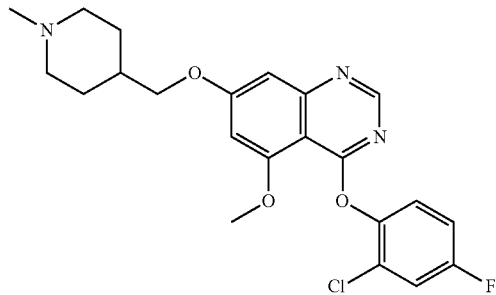 [SMILES: COc1cc(OCC2CCN(C)CC2)cc2ncnc(Oc3ccc(F)cc3Cl)c12]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 5-methoxy-7-((1-methylpiperidin-4-yl)methoxy)quinazolin-4(3H)-one to react with POCl$_3$ to generate the corresponding chloride then to react with 2-chloro-4-fluorophenol, the title compound was obtained as a white solid in 28% yield. $^1$H NMR (300 MHz, CDCl$_3$): δ8.53 (s, 1H), 7.30-7.20 (m, 1H), 7.10-7.05 (m, 1H), 6.91 (d, J=2.1 Hz, 1H), 6.60 (d, J=2.1 Hz, 1H), 4.05-3.95 (m, 5H), 3.00-2.90 (m, 2H), 2.33 (s, 3H), 2.05-2.00 (m, 2H), 1.95-1.85 (m, 3H), 1.60-1.50 (m, 2H); MS (ES+): m/z 432.3 and 434.3 (M+1).

Example 2.35

Synthesis of 3-methyl-N-(7-(3-morpholinopropoxy)-5-((tetrahydro-2H-pyran-4-yl)oxy)quinazolin-4-yl)isoxazol-5-amine

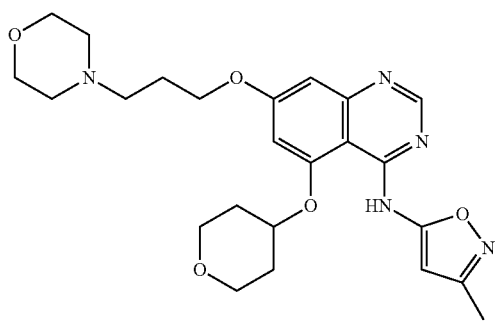 [SMILES: Cc1cc(Nc2ncnc3cc(OCCCN4CCOCC4)cc(OC4CCOCC4)c23)on1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(3-morpholinopropoxy)-5-((tetrahydro-2H-pyran-4-yl)oxy)quinazolin-4(3H)-one to react with POCl$_3$ to generate the corresponding chloride then to react with 3-methylisoxazol-5-amine, the title compound was obtained as a pale yellow solid in 11% yield. $^1$H NMR (300 MHz, CDCl$_3$): δ10.57 (s, 1H), 8.70 (s, 1H), 6.91 (d, J=2.1 Hz, 1H), 6.57 (s, 1H), 6.56 (d, J=2.1 Hz, 1H), 4.88-4.78 (m, 1H), 4.17 (t, J=6.3 Hz, 2H), 4.12-4.04 (m, 2H), 3.78-3.65 (m, 6H), 2.62-2.45 (m, 6H), 2.33 (s, 3H), 2.32-2.22 (m, 2H), 2.22-1.98 (m, 4H); MS (ES+): m/z 470.4 (M+1).

Example 2.36

Synthesis of 5-methyl-N-(7-((1-methylpiperidin-4-yl)methoxy)-5-((tetrahydro-2H-pyran-4-yl)oxy)quinazolin-4-yl)-1,3,4-thiadiazol-2-amine

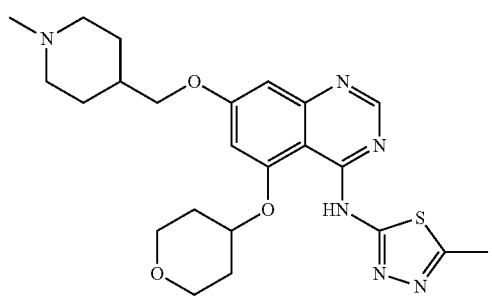

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl$_3$ to generate the corresponding chloride then to react with 5-methyl-1,3,4-thiadiazol-2-amine, the title compound was obtained as a white solid in 12% yield. $^1$H NMR (400 MHz, CDCl$_3$): δ8.69 (s, 1H), 6.88 (d, J=2.4 Hz, 1H), 6.58 (d, J=2.4 Hz, 1H), 4.88-4.75 (m, 1H), 4.18-4.08 (m, 2H), 3.97 (d, J=6.0 Hz, 2H), 3.75-3.66 (m, 2H), 2.97-2.90 (m, 2H), 2.73 (s, 3H), 2.32 (s, 3H), 2.31-2.24 (m, 2H), 2.16-1.97 (m, 4H), 1.92-1.80 (m, 3H), 1.62-1.49 (m, 2H); MS (ES+): m/z 471.3 (M+1).

Example 2.37

Synthesis of N-(7-((1-methylpiperidin-4-yl)methoxy)-5-((tetrahydro-2H-pyran-4-yl)oxy)quinazolin-4-yl)-5-(trifluoromethyl)-1,3,4-thiadiazol-2-amine

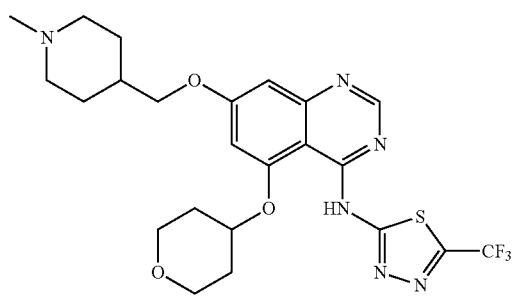 [SMILES: CN1CCC(COc2cc(OC3CCOCC3)c3c(Nc4nnc(C(F)(F)F)s4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl$_3$ to generate the corresponding chloride then to react with 5-(trifluoromethyl)-1,3,4-thiadiazol-2-amine, the title compound was obtained as a white solid in 12% yield. $^1$H NMR (400 MHz, CDCl$_3$): δ8.76 (s, 1H), 6.93 (d, J=2.0 Hz, 1H), 6.62 (d, J=2.0 Hz, 1H), 4.90-4.80 (m, 1H), 4.18-4.08 (m, 2H), 3.98 (d, J=5.6 Hz, 2H), 3.76-3.68 (m, 2H), 2.97-2.90 (m, 2H), 2.32 (s, 3H), 2.31-2.26 (m, 2H), 2.17-1.96 (m, 4H), 1.95-1.80 (m, 3H), 1.61-1.47 (m, 2H); MS (ES+): m/z 525.2 (M+1).

Example 2.38

Synthesis of N-(7-((1-methylpiperidin-4-yl)methoxy)-5-((tetrahydro-2H-pyran-4-yl)oxy)quinazolin-4-yl)-1,3,4-thiadiazol-2-amine

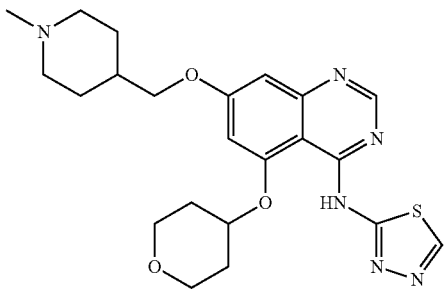 [SMILES: CN1CCC(COc2cc(OC3CCOCC3)c3c(Nc4nncs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl$_3$ to generate the corresponding chloride then to react with 1,3,4-thiadiazol-2-amine, the title compound was obtained as a white solid in 4% yield. ¹H NMR (400 MHz, CDCl₃): δ11.30 (s, 1H), 8.87 (s, 1H), 8.75 (s, 1H), 6.91 (d, J=2.4 Hz, 1H), 6.61 (d, J=2.4 Hz, 1H), 4.90-4.80 (m, 1H), 4.19-4.08 (m, 2H), 3.99 (d, J=5.6 Hz, 2H), 3.76-3.68 (m, 2H), 3.03-2.96 (m, 2H), 2.35 (s, 3H), 2.34-2.28 (m, 2H), 2.20-2.02 (m, 4H), 1.92-1.84 (m, 3H), 1.66-1.50 (m, 2H); MS (ES+): m/z 457.3 (M+1).

Example 2.39

Synthesis of N-(7-((1-methylpiperidin-4-yl)methoxy)-5-((tetrahydro-2H-pyran-4-yl)oxy)quinazolin-4-yl)thiazol-2-amine

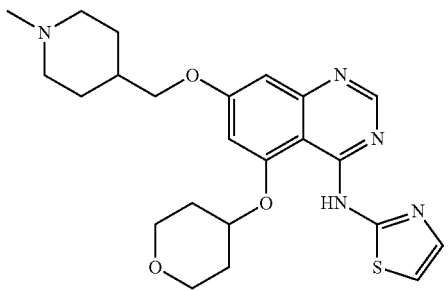 [SMILES: CN1CCC(COc2cc(OC3CCOCC3)c3c(Nc4nccs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with thiazol-2-amine, the title compound was obtained as a white solid in 7% yield. ¹H NMR (400 MHz, CDCl₃): δ11.09 (s, 1H), 8.76 (s, 1H), 7.53 (d, J=3.6 Hz, 1H), 7.02 (d, J=3.6 Hz, 1H), 6.88 (d, J=2.0 Hz, 1H), 6.57 (d, J=2.0 Hz, 1H), 4.88-4.78 (m, 1H), 4.20-4.12 (m, 2H), 3.98 (d, J=5.6 Hz, 2H), 3.76-3.68 (m, 2H), 3.02-2.94 (m, 2H), 2.34 (s, 3H), 2.32-2.26 (m, 2H), 2.16-2.00 (m, 4H), 1.94-1.84 (m, 3H), 1.65-1.50 (m, 2H); MS (ES+): m/z 456.3 (M+1).

Example 2.40

Synthesis of 3-methyl-N-(7-((1-methylpiperidin-4-yl)methoxy)-5-((tetrahydro-2H-pyran-4-yl)oxy)quinazolin-4-yl)isoxazol-5-amine

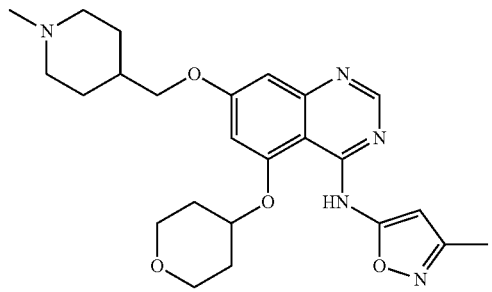

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 3-methylisoxazol-5-amine, the title compound was obtained as a white solid in 24% yield. ¹H NMR (400 MHz, CDCl₃): δ10.57 (s, 1H), 8.71 (s, 1H), 6.88 (d, J=2.0 Hz, 1H), 6.58 (s, 1H), 6.56 (d, J=2.0 Hz, 1H), 4.85-4.75 (m, 1H), 4.13-4.05 (m, 2H), 3.97 (d, J=5.6 Hz, 2H), 3.75-3.67 (m, 2H), 2.97-2.89 (m, 2H), 2.33 (s, 3H), 2.32 (s, 3H), 2.31-2.23 (m, 2H), 2.10-1.95 (m, 4H), 1.93-1.82 (m, 3H), 1.60-1.46 (m, 2H); MS (ES+): m/z 454.4 (M+1).

Example 2.41

Synthesis of N-(7-(4-(2-methoxyethyl)piperazin-1-yl)-5-((tetrahydro-2H-pyran-4-yl)oxy)quinazolin-4-yl)-4-(trifluoromethyl)thiazol-2-amine

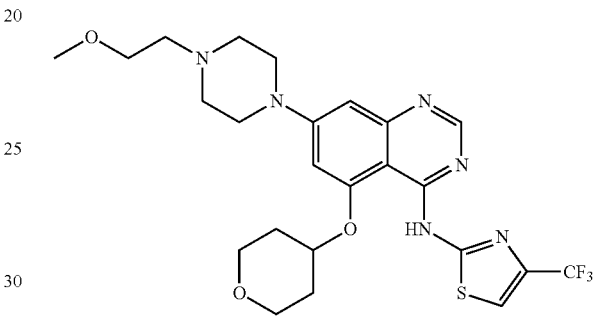

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(4-(2-methoxyethyl)piperazin-1-yl)-5-((tetrahydro-2H-pyran-4-yl)oxy)quinazolin-4(3H)-one to react with POCl₃ to generate the corresponding chloride then to react with 4-(trifluoromethyl)thiazol-2-amine, the title compound was obtained as a white solid in 22% yield. ¹H NMR (400 MHz, CDCl₃): δ11.08 (s, 1H), 8.69 (s, 1H), 7.39 (s, 1H), 6.85 (d, J=2.0 Hz, 1H), 6.60 (d, J=2.0 Hz, 1H), 4.90-4.82 (m, 1H), 4.20-4.10 (m, 2H), 3.78-3.70 (m, 2H), 3.58-3.63 (m, 2H), 3.53-3.43 (m, 4H), 3.40 (s, 3H), 2.75-2.68 (m, 6H), 2.32-2.23 (m, 2H), 2.15-2.06 (m, 2H); MS (ES+): m/z 539.4 (M+1).

Example 2.42

Synthesis of 4-methyl-N-(7-((1-methylpiperidin-4-yl)methoxy)-5-((tetrahydro-2H-pyran-4-yl)oxy)quinazolin-4-yl)thiazol-2-amine

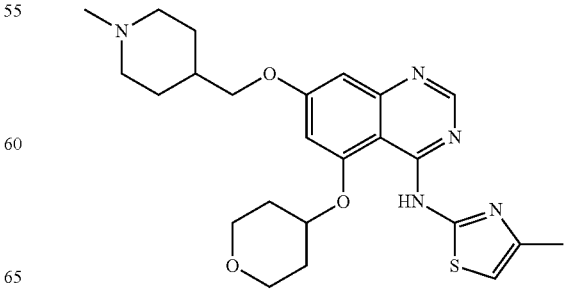

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 4-methylthiazol-2-amine, the title compound was obtained as a white solid in 13% yield. ¹H NMR (400 MHz, CDCl₃): δ8.71 (s, 1H), 6.85 (d, J=2.0 Hz, 1H), 6.55 (d, J=2.0 Hz, 1H), 6.54 (s, 1H), 4.85-4.76 (m, 1H), 4.18-4.10 (m, 2H), 3.95 (d, J=5.6 Hz, 2H), 3.74-3.66 (m, 2H), 2.98-2.90 (m, 2H), 2.37 (s, 3H), 2.32 (s, 3H), 2.29-2.22 (m, 2H), 2.15-1.96 (m, 4H), 1.88-1.80 (m, 3H), 1.60-1.47 (m, 2H); MS (ES+): m/z 470.4 (M+1).

Example 2.43

Synthesis of 5-methyl-N-(7-((1-methylpiperidin-4-yl)methoxy)-5-((tetrahydro-2H-pyran-4-yl)oxy)quinazolin-4-yl)thiazol-2-amine

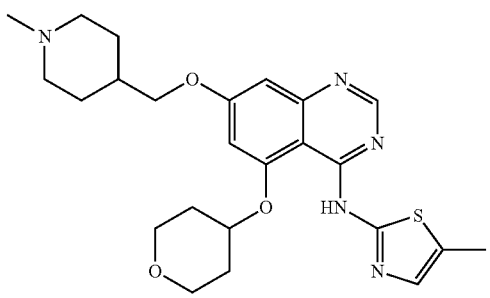

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 4-methylthiazol-2-amine, the title compound was obtained as a yellowish solid in 24% yield. ¹H NMR (400 MHz, CDCl₃): δ8.70 (s, 1H), 7.14 (s, 1H), 6.85 (d, J=2.0 Hz, 1H), 6.54 (d, J=2.0 Hz, 1H), 4.83-4.75 (m, 1H), 4.16-4.08 (m, 2H), 3.95 (d, J=5.6 Hz, 2H), 3.72-3.64 (m, 2H), 2.96-2.88 (m, 2H), 2.43 (s, 3H), 2.31 (s, 3H), 2.29-2.20 (m, 2H), 2.13-1.95 (m, 4H), 1.90-1.78 (m, 3H), 1.58-1.45 (m, 2H); MS (ES+): m/z 470.4 (M+1).

Example 2.44

Synthesis of N-(7-(4-(2-(dimethylamino)ethyl)piperidin-1-yl)-5-((tetrahydro-2H-pyran-4-yl)oxy)quinazolin-4-yl)-4-(trifluoromethyl)thiazol-2-amine

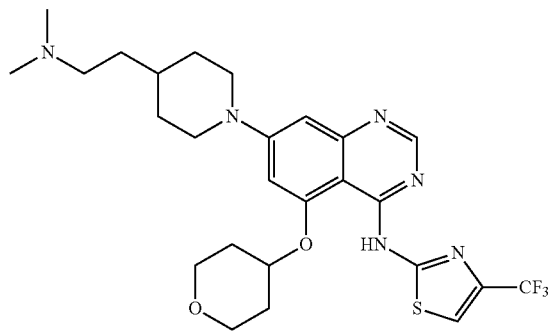 [SMILES: CN(C)CCC1CCN(c2cc(OC3CCOCC3)c3c(Nc4nc(C(F)(F)F)cs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(4-(2-(dimethylamino)ethyl)piperidin-1-yl)-5-((tetrahydro-2H-pyran-4-yl)oxy)quinazolin-4(3H)-one to react with POCl₃ to generate the corresponding chloride then to react with 4-(trifluoromethyl)thiazol-2-amine, the title compound was obtained as a yellowish foam in 8% yield. ¹H NMR (400 MHz, CDCl₃): δ 11.06 (s, 1H), 8.67 (s, 1H), 7.88 (s, 1H), 6.82 (d, J=2.0 Hz, 1H), 6.59 (d, J=2.0 Hz, 1H), 4.38-4.28 (m, 1H), 4.15-4.07 (m, 2H), 3.82-3.74 (m, 2H), 3.25-3.16 (m, 2H), 2.99-2.89 (m, 2H), 2.40-2.32 (m, 2H), 2.30-2.20 (m, 8H), 2.15-2.05 (m, 2H), 1.90-1.80 (m, 2H), 1.68-1.57 (m, 1H), 1.52-1.45 (m, 2H), 1.42-1.30 (m, 2H); MS (ES+): m/z 551.4 (M+1).

Example 2.45

Synthesis of N-(7-(2-(1-methylpiperidin-4-yl)ethoxy)-5-((tetrahydro-2H-pyran-4-yl)oxy)quinazolin-4-yl)-4-(trifluoromethyl)thiazol-2-amine

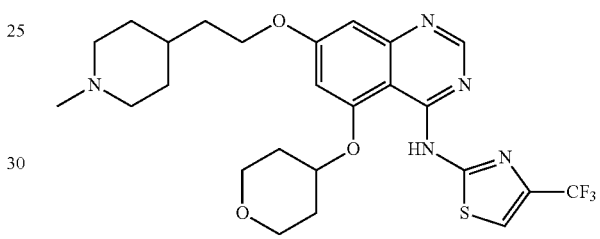

Following the procedure as described in Example 2, replacing 2-chloro-4-fluorophenol with 4-(trifluoromethyl)thiazol-2-amine, the title compound was obtained as a white solid in 15% yield. ¹H NMR (400 MHz, CDCl₃): δ11.13 (s, 1H), 8.76 (s, 1H), 7.40 (s, 1H), 6.91 (d, J=2.0 Hz, 1H), 6.58 (d, J=2.0 Hz, 1H), 4.38-4.30 (m, 1H), 4.19-4.10 (m, 4H), 3.77-3.67 (m, 2H), 2.94-2.86 (m, 2H), 2.30 (s, 3H), 2.29-2.23 (m, 2H), 2.15-2.05 (m, 2H), 2.03-1.94 (m, 2H), 1.85-1.73 (m, 4H), 1.60-1.50 (m, 1H), 1.47-1.33 (m, 2H); MS (ES+): m/z 538.4 (M+1).

Example 2.46

Synthesis of 4-((1-methyl-1H-imidazol-2-yl)thio)-7-((1-methylpiperidin-4-yl)methoxy)-5-((tetrahydro-2H-pyran-4-yl)oxy)quinazoline

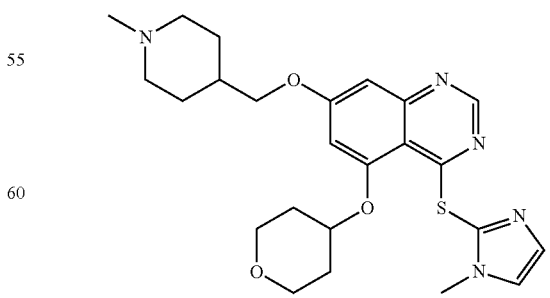

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 1-methyl-1H-imidazole-2-thiol, the title compound was obtained as a white solid in 11% yield. ¹H NMR (400 MHz, CDCl₃): δ8.60 (s, 1H), 7.26 (d, J=0.8 Hz, 1H), 7.21 (d, J=0.8 Hz, 1H), 6.82 (d, J=2.2 Hz, 1H), 6.54 (d, J=2.2 Hz, 1H), 4.81-4.75 (m, 1H), 4.20-4.10 (m, 2H), 3.97 (d, J=5.8 Hz, 2H), 3.69-3.62 (m, 5H), 3.05-2.90 (m, 2H), 2.34 (s, 3H), 2.25-2.15 (m, 2H), 2.14-2.00 (m, 3H), 1.95-1.80 (m, 3H), 1.65-1.50 (m, 2H); MS (ES+): m/z 470.4 (M+1).

Example 2.47

Synthesis of 2-((7-((1-methylpiperidin-4-yl)methoxy)-5-((tetrahydro-2H-pyran-4-yl)oxy)quinazolin-4-yl)thio)-1,3,4-thiadiazole

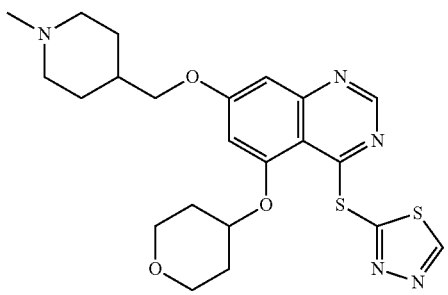 [SMILES: CN1CCC(COc2cc(OC3CCOCC3)c3c(Sc4nncs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 1,3,4-thiadiazole-2-thiol, the title compound was obtained as a white solid in 6% yield. ¹H NMR (400 MHz, CDCl₃): δ9.30 (s, 1H), 8.84 (s, 1H), 6.88 (d, J=2.2 Hz, 1H), 6.61 (d, J=2.2 Hz, 1H), 4.86-4.76 (m, 1H), 4.20-4.10 (m, 2H), 4.05 (d, J=5.8 Hz, 2H), 3.75-3.62 (m, 2H), 3.55-3.40 (m, 2H), 2.73 (s, 3H), 2.70-2.62 (m, 2H), 2.28-2.20 (m, 2H), 2.19-2.00 (m, 7H); MS (ES+): m/z 474.3 (M+1).

Example 2.48

Synthesis of 2-methyl-5-((7-((1-methylpiperidin-4-yl)methoxy)-5-((tetrahydro-2H-pyran-4-yl)oxy)quinazolin-4-yl)thio)-1,3,4-thiadiazole

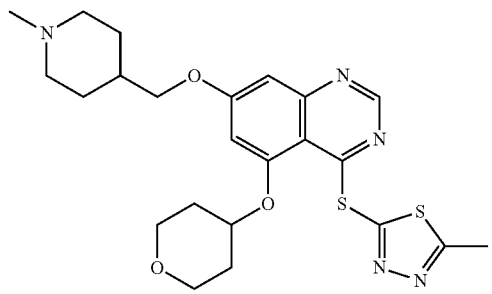

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 5-methyl-1,3,4-thiadiazole-2-thiol, the title compound was obtained as a white solid in 50% yield. ¹H NMR (400 MHz, CDCl₃): δ8.78 (s, 1H), 6.84 (d, J=2.2 Hz, 1H), 6.58 (d, J=2.2 Hz, 1H), 4.85-4.75 (m, 1H), 4.20-4.10 (m, 2H), 4.05 (d, J=5.6 Hz, 2H), 3.75-3.65 (m, 4H), 2.85 (s, 3H), 2.80 (s, 3H), 2.78-2.70 (m, 2H), 2.35-2.23 (m, 4H), 2.25-2.00 (m, 5H); MS (ES+): m/z 488.4 (M+1).

Example 2.49

Synthesis of 4,5-dimethyl-2-((7-((1-methylpiperidin-4-yl)methoxy)-5-((tetrahydro-2H-pyran-4-yl)oxy)quinazolin-4-yl)thio)oxazole

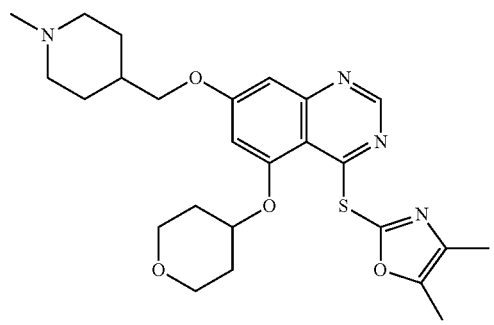

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 4,5-dimethyloxazole-2-thiol, the title compound was obtained as a white solid in 50% yield. ¹H NMR (400 MHz, CDCl₃): δ8.65 (s, 1H), 6.82 (d, J=2.2 Hz, 1H), 6.53 (d, J=2.2 Hz, 1H), 4.80-4.70 (m, 1H), 4.18-4.08 (m, 2H), 3.97 (d, J=5.7 Hz, 2H), 3.72-3.62 (m, 2H), 3.05-2.80 (m, 2H), 2.43 (s, 3H), 2.36 (s, 3H), 2.20 (s, 3H), 2.18-2.12 (m, 6H), 2.10-1.98 (m, 3H), 1.95-1.82 (m, 2H); MS (ES+): m/z 485.4 (M+1).

Example 2.50

Synthesis of 2-((7-((1-methylpiperidin-4-yl)methoxy)-5-((tetrahydro-2H-pyran-4-yl)oxy)quinazolin-4-yl)thio)-4-(trifluoromethyl)thiazole

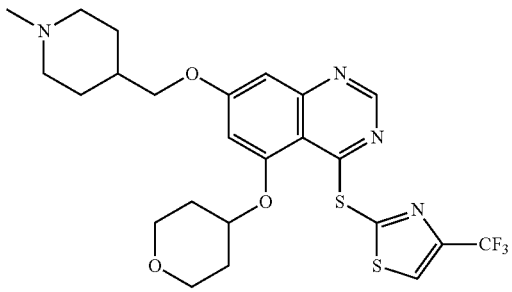 [SMILES: CN1CCC(COc2cc(OC3CCOCC3)c3c(Sc4nc(C(F)(F)F)cs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 4-(trifluoromethyl)thiazole-2-thiol, the title compound was obtained as a white solid in 48% yield. ¹H NMR (400 MHz, CDCl₃): δ8.87 (s, 1H), 7.90 (s, 1H), 6.88 (d, J=2.2 Hz, 1H), 6.58 (d, J=2.2 Hz, 1H), 4.80-4.71 (m, 1H), 4.20-4.10 (m, 2H), 4.00 (d, J=5.8 Hz, 2H), 3.72-3.62 (m, 2H), 3.20-3.10 (m, 2H), 2.49 (s, 3H), 2.35-2.18 (m, 2H), 2.15-2.05 (m, 4H), 2.00-1.85 (m, 3H), 1.80-1.68 (m, 2H); MS (ES+): m/z 541.3 (M+1).

Example 2.51

Synthesis of 4-methyl-2-((7-((1-methylpiperidin-4-yl)methoxy)-5-((tetrahydro-2H-pyran-4-yl)oxy)quinazolin-4-yl)thio)thiazole

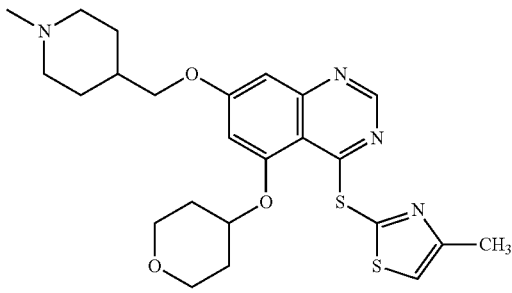

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with 4-methylthiazole-2-thiol, the title compound was obtained as a white solid in 48% yield. ¹H NMR (400 MHz, CDCl₃): δ8.74 (s, 1H), 7.12 (q, J=1.0 Hz, 1H), 6.82 (d, J=2.2 Hz, 1H), 6.58 (d, J=2.2 Hz, 1H), 4.85-4.75 (m, 1H), 4.20-4.10 (m, 2H), 3.98 (d, J=5.6 Hz, 2H), 3.72-3.50 (m, 2H), 3.30-3.15 (m, 2H), 2.53 (s, 3H), 2.52 (s, 3H), 2.45-2.30 (m, 2H), 2.25-2.15 (m, 2H), 2.12-2.03 (m, 2H), 2.00-1.90 (m, 3H), 1.90-1.75 (m, 2H); MS (ES+): m/z 487.3 (M+1).

Example 2.52

Synthesis of 2-((7-((1-methylpiperidin-4-yl)methoxy)-5-((tetrahydro-2H-pyran-4-yl)oxy)quinazolin-4-yl)thio)thiazole

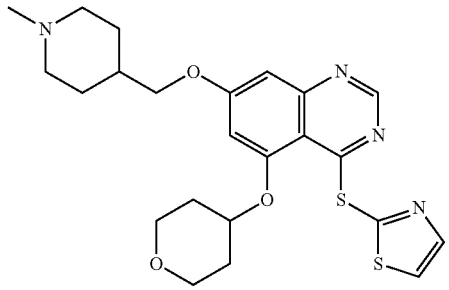 [SMILES: CN1CCC(COc2cc(OC3CCOCC3)c3c(Sc4nccs4)ncnc3c2)CC1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-((tetrahydro-2H-pyran-4-yl)oxy)quinazolin-4(3H)-one to react with POCl₃ to generate the corresponding chloride then to react with thiazole-2-thiol, the title compound was obtained as a white solid in 18% yield. ¹H NMR (400 MHz, CDCl₃): δ8.78 (s, 1H), 7.97 (d, J=3.4 Hz, 1H), 7.57 (d, J=3.4 Hz, 1H), 6.86 (d, J=2.2 Hz, 1H), 6.56 (d, J=2.2 Hz, 1H), 4.82-4.71 (m, 1H), 4.20-4.04 (m, 2H), 3.97 (d, J=5.8 Hz, 2H), 3.75-3.62 (m, 2H), 3.05-2.90 (m, 2H), 2.33 (s, 3H), 2.25-2.18 (m, 2H), 2.18-2.00 (m, 7H), 1.90-1.80 (m, 2H); MS (ES+): m/z 473.3 (M+1).

Example 2.53

Synthesis of N-(7-(2-morpholinoethoxy)-5-((tetrahydro-2H-pyran-4-yl)oxy)quinazolin-4-yl)-4-(trifluoromethyl)thiazol-2-amine

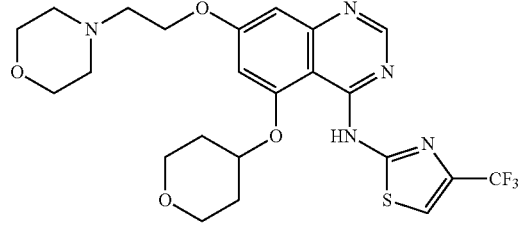 [SMILES: FC(F)(F)c1csc(Nc2ncnc3cc(OCCN4CCOCC4)cc(OC4CCOCC4)c23)n1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-morpholinoethoxy)-5-((tetrahydro-2H-pyran-4-yl)oxy)quinazolin-4(3H)-one to react with POCl₃ to generate the corresponding chloride then to react with 4-(trifluoromethyl)-thiazol-2-amine, the title compound was obtained as a white solid in 18% yield. ¹H NMR (400 MHz, CDCl₃): δ8.76 (s, 1H), 7.41 (d, J=0.8 Hz, 1H), 6.92 (d, J=2.0 Hz, 1H), 6.63 (d, J=2.0 Hz, 1H), 4.86-4.80 (m, 1H), 4.26 (t, J=5.2 Hz, 2H), 4.17-4.10 (m, 2H), 3.77 (t, J=4.8 Hz, 2H), 3.76-3.67 (m, 4H), 2.88 (t, J=5.2 Hz, 2H), 2.64-2.56 (m, 4H), 2.31-2.24 (m, 2H), 2.14-2.05 (m, 2H); MS (ES+): m/z 526.3 (M+1).

Example 2.54

Synthesis of N-(7-(3-(dimethylamino)propoxy)-5-((tetrahydro-2H-pyran-4-yl)oxy)quinazolin-4-yl)-4-(trifluoromethyl)thiazol-2-amine

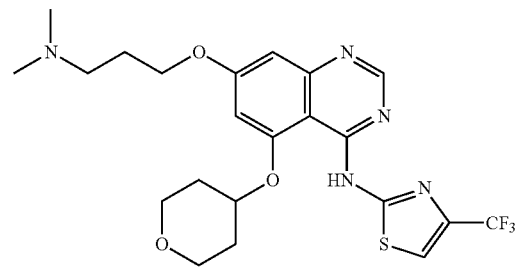 [SMILES: CN(C)CCCOc1cc(OC2CCOCC2)c2c(Nc3nc(C(F)(F)F)cs3)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(3-(dimethylamino)propoxy)-5-((tetrahydro-2H-pyran-4-yl)oxy)quinazolin-4(3H)-one to react with POCl₃ to generate the corresponding chloride then to react with 4-(trifluoromethyl)thiazol-2-amine, the title compound was obtained as a white solid in 16% yield. ¹H NMR (400 MHz, CDCl₃): δ11.14 (s, 1H), 8.76 (s, 1H), 7.41 (s, 1H), 6.93 (d, J=2.0 Hz, 1H), 6.60 (d, J=2.0 Hz, 1H), 4.89-4.81 (m, 1H), 4.17 (t, J=6.4 Hz, 2H), 4.15-4.10 (m, 2H), 3.77-3.69 (m, 2H), 2.52 (t, J=7.2 Hz, 2H), 2.31 (s, 6H), 2.30-2.25 (m, 2H), 2.15-2.00 (m, 4H); MS (ES+): m/z 498.4 (M+1).

Example 2.55

Synthesis of (R)-3-((5-((tetrahydro-2H-pyran-4-yl)oxy)-4-((4-(trifluoromethyl)thiazol-2-yl)amino)quinazolin-7-yl)oxy)propane-1,2-diol

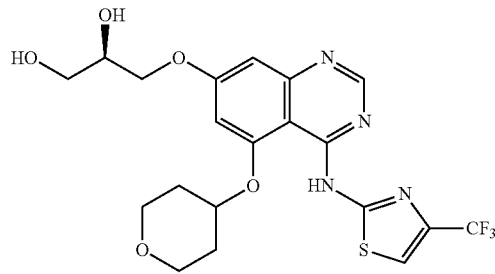 [SMILES: OC[C@@H](O)COc1cc(OC2CCOCC2)c2c(Nc3nc(C(F)(F)F)cs3)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with (S)-7-((2,2-dimethyl-1,3-dioxolan-4-yl)methoxy)-5-((tetrahydro-2H-pyran-4-yl)oxy)-quinazolin-4(3H)-one to react with POCl₃ to generate the corresponding chloride then to react with 4-(trifluoromethyl)thiazol-2-amine, the title compound was obtained as a white solid in 22% yield. ¹H NMR (400 MHz, CDCl₃): δ8.92 (s, 1H), 7.75 (br s, 1H), 7.73 (s, 1H), 7.13 (d, J=2.0 Hz, 1H), 7.02 (d, J=2.0 Hz, 1H), 5.19-5.16 (m, 1H), 4.44 (dd, J=9.6, 5.6 Hz, 1H), 4.40-4.26 (m, 4H), 4.02-3.92 (m, 4H), 2.57-2.47 (m, 2H), 2.39-2.29 (m, 2H); MS (ES+): m/z 485.2 (M+1).

Example 2.56

Synthesis of N-(7-(2-(2-(dimethylamino)ethoxy)ethoxy)-5-((tetrahydro-2H-pyran-4-yl)oxy)quinazolin-4-yl)-4-(trifluoromethyl)thiazol-2-amine

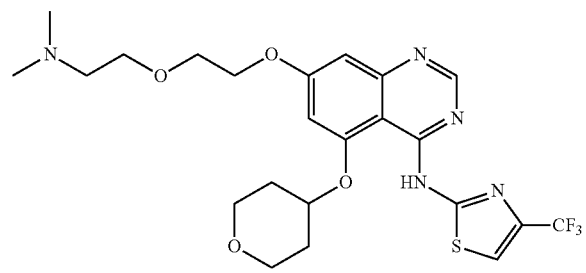 [SMILES: CN(C)CCOCCOc1cc(OC2CCOCC2)c2c(Nc3nc(C(F)(F)F)cs3)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(2-(dimethylamino)ethoxy)ethoxy)-5-((tetrahydro-2H-pyran-4-yl)oxy)quinazolin-4(3H)-one to react with POCl₃ to generate the corresponding chloride then to react with 4-(trifluoromethyl)thiazol-2-amine, the title compound was obtained as a yellowish solid in 9% yield. ¹H NMR (400 MHz, CDCl₃): δ 11.13 (s, 1H), 8.75 (s, 1H), 7.41 (s, 1H), 6.91 (d, J=2.0 Hz, 1H), 6.65 (d, J=2.0 Hz, 1H), 4.86-4.78 (m, 1H), 4.30-4.24 (m, 2H), 4.18-4.08 (m, 2H), 3.92-3.86 (m, 2H), 3.74-3.64 (m, 4H), 2.57 (t, J=6.0 Hz, 2H), 2.32-2.23 (m, 8H), 2.15-2.04 (m, 2H); MS (ES): m/z 528.4 (M+1).

Example 2.57

Synthesis of N-(7-(4-(2-(dimethyl-amino)ethyl)piperazin-1-yl)-5-((tetrahydro-2H-pyran-4-yl)oxy)-quinazolin-4-yl)-4-(trifluoromethyl)-thiazol-2-amine

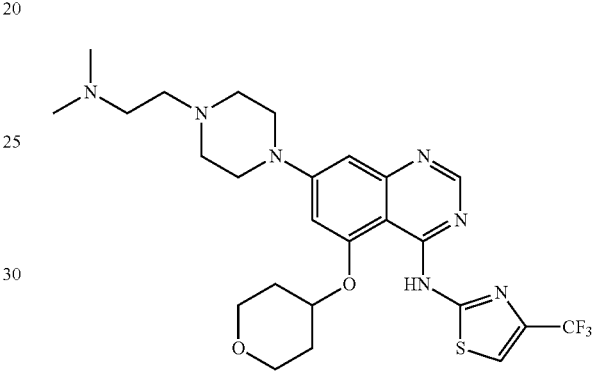

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(4-(2-(dimethylamino)ethyl)piperazin-1-yl)-5-((tetrahydro-2H-pyran-4-yl)oxy)quinazolin-4(3H)-one to react with POCl₃ to generate the corresponding chloride then to react with 4-(trifluoromethyl)thiazol-2-amine, the title compound was obtained as a yellowish solid in 5% yield. ¹H NMR (400 MHz, CDCl₃): δ 11.07 (s, 1H), 8.68 (s, 1H), 7.39 (s, 1H), 6.83 (d, J=2.0 Hz, 1H), 6.59 (d, J=2.0 Hz, 1H), 4.90-4.80 (m, 1H), 4.40-4.20 (m, 2H), 3.76-3.78 (m, 2H), 3.45-3.35 (m, 4H), 2.72-2.66 (m, 4H), 2.65-2.60 (m, 4H), 2.40 (s, 6H), 2.30-2.23 (m, 2H), 2.15-2.04 (m, 2H); MS (ES+): m/z 552.4 (M+1).

Example 2.58

Synthesis of N-(7-((1-methylpiperidin-4-yl)methoxy)-5-((tetrahydro-2H-pyran-4-yl)oxy)quinazolin-4-yl)-3-(trifluoromethyl)isoxazol-5-amine

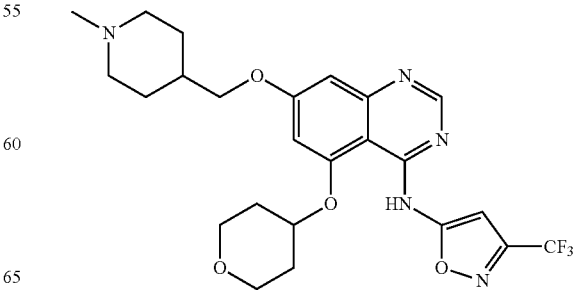

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-(tetrahydro-2H-pyran-4-yloxy)quinazolin-4(3H)-one to react with POCl$_3$ to generate the corresponding chloride then to react with 3-(trifluoromethyl)isoxazol-5-amine, the title compound was obtained as a white solid in 12% yield. $^1$H NMR (400 MHz, CDCl$_3$): δ11.80 (s, 1H), 8.74 (s, 1H), 7.00 (s, 1H), 6.90 (d, J=2.0 Hz, 1H), 6.59 (d, J=2.0 Hz, 1H), 4.86-4.77 (m, 1H), 4.13-4.05 (m, 2H), 3.98 (d, J=5.6 Hz, 2H), 3.76-3.68 (m, 2H), 3.05-2.95 (m, 2H), 2.37 (s, 3H), 2.32-2.25 (m, 2H), 2.15-1.97 (m, 4H), 1.95-1.80 (m, 3H), 1.70-1.55 (m, 2H); MS (ES+): m/z 508.4 (M+1).

Example 2.59

Synthesis of N$^7$-(3-(dimethylamino)-propyl)-N$^7$-methyl-5-((tetrahydro-2H-pyran-4-yl)oxy)-N$^4$-(4-(trifluoromethyl)thiazol-2-yl)quinazoline-4,7-diamine

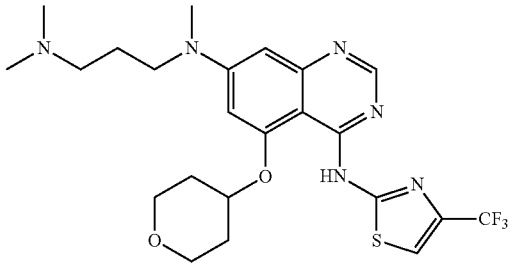 [SMILES: CN(C)CCCN(C)c1cc(OC2CCOCC2)c2c(Nc3nc(C(F)(F)F)cs3)ncnc2c1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(N-(3-(dimethylamino)propyl)-N-methylamino)-5-(tetrahydro-2H-pyran-4-yloxy)quinazolin-4(3H)-one to react with POCl$_3$ to generate the corresponding chloride then to react with 4-(trifluoromethyl)thiazol-2-amine, the title compound was obtained as a yellowish solid in 9% yield. $^1$H NMR (400 MHz, CDCl$_3$): δ8.62 (s, 1H), 7.36 (s, 1H), 6.64 (d, J=2.0 Hz, 1H), 6.54 (d, J=2.0 Hz, 1H), 4.90-4.80 (m, 1H), 4.18-4.08 (m, 2H), 3.76-3.68 (m, 2H), 3.51 (t, J=7.2 Hz, 2H), 3.08 (s, 3H), 2.45-2.30 (m, 2H), 2.30-2.20 (m, 8H), 2.15-2.00 (m, 2H), 1.85-1.75 (m, 2H); MS (ES+): m/z 511.4 (M+1).

Example 2.60

Synthesis of N-(7-(2-(piperidin-1-yl)ethoxy)-5-((tetrahydro-2H-pyran-4-yl)oxy)quinazolin-4-yl)-4-(trifluoromethyl)thiazol-2-amine

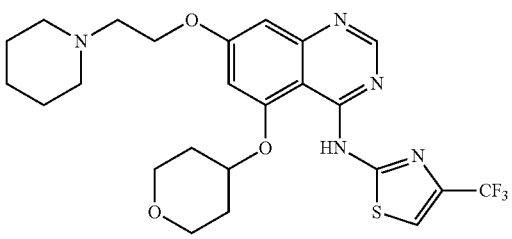 [SMILES: FC(F)(F)c1csc(Nc2ncnc3cc(OCCN4CCCCC4)cc(OC4CCOCC4)c23)n1]

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-(2-(piperidin-1-yl)ethoxy)-5-(tetrahydro-2H-pyran-4-yloxy)quinazolin-4(3H)-one to react with POCl$_3$ to generate the corresponding chloride then to react with 4-(trifluoromethyl)thiazol-2-amine, the title compound was obtained as a yellowish solid in 11% yield. $^1$H NMR (400 MHz, CDCl$_3$): δ11.03 (s, 1H), 8.76 (s, 1H), 7.40 (s, 1H), 6.92 (d, J=2.0 Hz, 1H), 6.65 (d, J=2.0 Hz, 1H), 4.90-4.78 (m, 1H), 4.26 (t, J=5.6 Hz, 2H), 4.18-4.10 (m, 2H), 3.76-3.68 (m, 2H), 2.86 (t, J=5.6 Hz, 2H), 2.62-2.50 (m, 4H), 2.32-2.23 (m, 2H), 2.15-2.05 (m, 2H), 1.70-1.60 (m, 4H), 1.55-1.44 (m, 2H); MS (ES+): m/z 524.3 (M+1).

Example 2.61

Synthesis of N-(7-((1-methylpiperidin-4-yl)methoxy)-5-((tetrahydro-2H-pyran-4-yl)oxy)-quinazolin-4-yl)isoxazol-3-amine

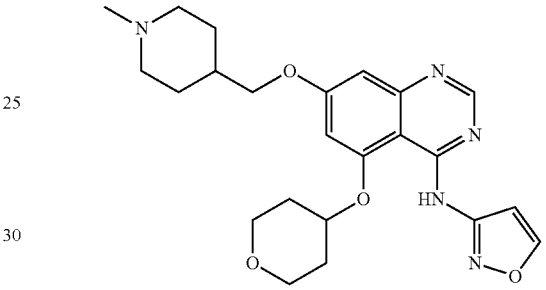

Following the procedure as described in Example 2, replacing 7-(2-(1-methyl-piperidin-4-yl)ethoxy)-5-((tetrahydro-2H-pyran-4-yl)oxy)quinazolin-4(3H)-one with 7-((1-methylpiperidin-4-yl)methoxy)-5-(tetrahydro-2H-pyran-4-yloxy)quinazolin-4(3H)-one to react with POCl$_3$ to generate the corresponding chloride then to react with isoxazol-3-amine, the title compound was obtained as a yellowish solid in 14% yield. $^1$H NMR (400 MHz, CDCl$_3$): δ10.41 (s, 1H), 8.61 (s, 1H), 8.34-8.32 (m, 1H), 7.46-7.44 (m, 1H), 6.83 (d, J=2.0 Hz, 1H), 6.53 (d, J=2.0 Hz, 1H), 4.82-4.75 (m, 1H), 4.13-4.05 (m, 2H), 3.95 (d, J=5.6 Hz, 2H), 3.73-3.65 (m, 2H), 2.97-2.90 (m, 2H), 2.31 (s, 3H), 2.29-2.20 (m, 2H), 2.08-1.96 (m, 4H), 1.90-1.80 (m, 3H), 1.60-1.47 (m, 2H); MS (ES+): m/z 440.4 (M+1).

Example 2.62

Synthesis of 3-((4-(2-chloro-4-fluorophenoxy)-5-((tetrahydro-2H-pyran-4-yl)oxy)quinazolin-7-yl)oxy)-N,N-dimethylpropan-1-amine

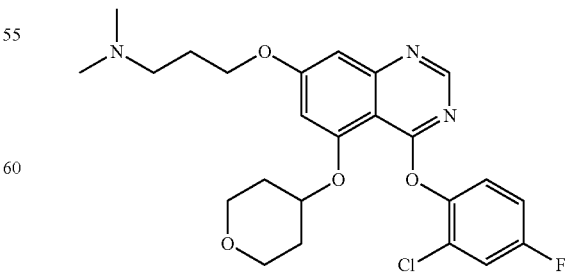

Following the procedure as described in Example 2, replacing 7-(2-(1-methylpiperidin-4-yl)ethoxy)-5-((tetrahydro-2H-pyran-4-yl)oxy)quinazolin-4(3H)-one with 7-(3-(dimethylamino)propoxy)-5-((tetrahydro-2H-pyran-4-yl) oxy)quinazolin-4(3H)-one to react with POCl$_3$ to generate the corresponding chloride then to react with 2-chloro-4-fluorophenol, the title compound was obtained as a white solid in 5% yield. $^1$H NMR (300 MHz, CDCl$_3$): δ8.54 (s, 1H), 7.33-7.20 (m, 2H), 7.14-7.04 (m, 1H), 6.93 (d, J=2.1 Hz, 1H), 6.60 (d, J=2.1 Hz, 1H), 4.84-4.74 (m, 1H), 4.19 (t, J=6.0 Hz, 2H), 4.04-3.92 (m, 2H), 3.72-3.60 (m, 2H), 2.70-2.54 (m, 2H), 2.39 (s, 6H), 2.18-2.05 (m, 4H), 2.04-1.90 (m, 2H); MS (ES+, m/z) 476.4 and 478.4 (M+1).

Example 2.63

Synthesis of 4-(2-chloro-4-fluorophenoxy)-7-(3-(4-methylpiperazin-1-yl)propoxy)-5-((tetrahydro-2H-pyran-4-yl)oxy)quinazoline

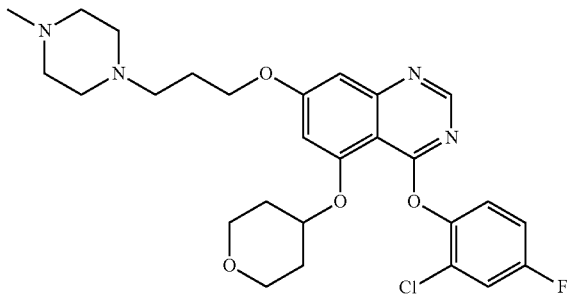 [SMILES: CN1CCN(CCCOc2cc(OC3CCOCC3)c3c(Oc4ccc(F)cc4Cl)ncnc3c2)CC1]

Following the procedure as described in Example 2, replacing 7-(2-(1-methylpiperidin-4-yl)ethoxy)-5-((tetrahydro-2H-pyran-4-yl)oxy)quinazolin-4(3H)-one with 7-(3-(4-methylpiperazin-1-yl)propoxy)-5-((tetrahydro-2H-pyran-4-yl)oxy)quinazolin-4(3H)-one to react with POCl$_3$ to generate the corresponding chloride then to react with 2-chloro-4-fluorophenol, the title compound was obtained as a yellowish oil in 12% yield. $^1$H NMR (300 MHz, CDCl$_3$): δ8.53 (s, 1H), 7.30-7.20 (m, 2H), 7.14-7.05 (m, 1H), 6.93 (d, J=2.4 Hz, 1H), 6.59 (d, J=2.4 Hz, 1H), 4.84-4.74 (m, 1H), 4.18 (t, J=6.3 Hz, 2H), 4.04-3.92 (m, 2H), 3.70-3.60 (m, 2H), 2.64-2.42 (m, 10H), 2.34 (s, 3H), 2.22-2.03 (m, 4H), 2.02-1.90 (m, 2H); MS (ES+, m/z) 531.4 and 533.4 (M+1).

Example 3

Synthesis of 4-(2-chloro-4-fluorophenoxy)-7-(2-(4-methylpiperazin-1-yl)ethoxy)-5-((tetrahydro-2H-pyran-4-yl)oxy)quinazoline

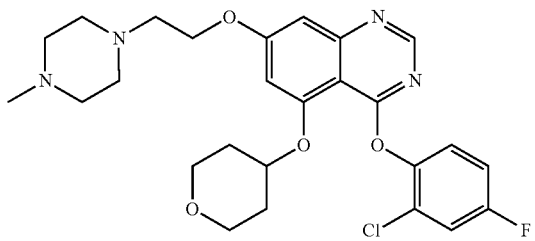 [SMILES: CN1CCN(CCOc2cc(OC3CCOCC3)c3c(Oc4ccc(F)cc4Cl)ncnc3c2)CC1]

To a solution of 4-chloro-7-(2-(4-methylpiperazin-1-yl) ethoxy)-5-((tetrahydro-2H-pyran-4-yl)oxy)quinazoline (0.10 g, 0.25 mmol) in 2 mL of 1,2-dimethoxyethane were added 2-chloro-4-fluorophenol (0.10 mL, 0.92 mmol) and cesium carbonate (0.10 g, 0.31 mmol). The mixture was heated at reflux for 20 h and the volatiles were removed in vacuo. The residue was purified by column chromatography eluted with 0.5:5:94.5 NH$_4$OH:methanol:dichloromethane afford the title compound as a gum in 12% yield (15 mg). $^1$H NMR (300 MHz, CDCl$_3$): δ8.55 (s, 1H), 7.31-7.20 (m, 2H), 7.13-7.05 (m, 1H), 6.93 (d, J=2.2 Hz, 1H), 6.63 (d, J=2.2 Hz, 1H), 4.84-4.74 (m, 1H), 4.26 (t, J=5.7 Hz, 2H), 4.04-3.91 (m, 2H), 3.71-3.60 (m, 2H), 2.90 (t, J=5.7 Hz, 2H), 2.70-2.61 (m, 4H), 2.60-2.44 (m, 4H), 2.32 (s, 3H), 2.15-2.01 (m, 2H), 2.00-1.78 (m, 2H); MS (ES+): m/z 517.4 and 519.4 (M+1).

The compounds listed below were prepared following the procedure as described in Example 3.

Example 3.1

Synthesis of 4-(2-chloro-4-fluorophenoxy)-7-methoxy-5-((tetrahydro-2H-pyran-4-yl)oxy)quinazoline

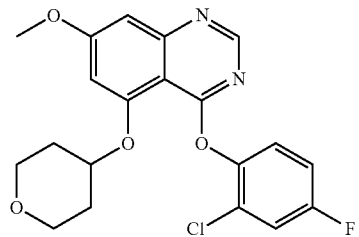 [SMILES: COc1cc(OC2CCOCC2)c2c(Oc3ccc(F)cc3Cl)ncnc2c1]

Following the procedure as described in Example 3, replacing 4-chloro-7-(2-(4-methylpiperazin-1-yl)ethoxy)-5-((tetrahydro-2H-pyran-4-yl)oxy)quinazoline with 4-chloro-7-methoxy-5-((tetrahydro-2H-pyran-4-yl)oxy)-quinazoline to react with 2-chloro-4-fluorophenol, the title compound was obtained as a white solid in 82% yield. $^1$H NMR (300 MHz, CDCl$_3$): δ8.56 (s, 1H), 7.30-7.22 (m, 2H), 7.14-7.04 (m, 1H), 6.95 (d, J=2.2 Hz, 1H), 6.60 (d, J=2.2 Hz, 1H), 4.84-4.74 (m, 1H), 4.04-3.91 (m, 5H), 3.70-3.60 (m, 2H), 2.20-2.08 (m, 2H), 2.07-1.93 (m, 2H); MS (ES+): m/z 405.3 and 407.3 (M+1).

Example 3.2

Synthesis of 7-(2-(4-methylpiperazin-1-yl)ethoxy)-4-phenoxy-5-((tetrahydro-2H-pyran-4-yl)oxy)quinazoline

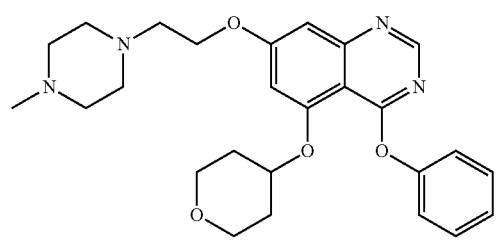 [SMILES: CN1CCN(CCOc2cc(OC3CCOCC3)c3c(Oc4ccccc4)ncnc3c2)CC1]

Following the procedure as described in Example 3, replacing 2-chloro-4-fluorophenol with phenol to react with 4-chloro-7-(2-(4-methylpiperazin-1-yl)ethoxy)-5-((tetrahydro-2H-pyran-4-yl)oxy)quinazoline, the title compound was obtained as a gum in 36% yield. $^1$H NMR (300 MHz, CDCl$_3$): δ8.58 (s, 1H), 7.51-7.44 (m, 2H), 7.33-7.20 (m, 3H), 6.92 (d, J=2.1 Hz, 1H), 6.63 (d, J=2.1 Hz, 1H), 4.84-4.74 (m, 1H), 4.26 (t, J=5.7 Hz, 2H), 4.05-3.95 (m, 2H), 3.71-3.60 (m, 2H), 2.91 (t, J=5.7 Hz, 2H), 2.81-2.54 (m, 8H), 2.39 (s, 3H), 2.15-1.98 (m, 2H), 1.97-1.87 (m, 2H); MS (ES+): m/z 465.5 (M+1).

Example 3.3

Synthesis of 4-((2-chloro-4-fluorophenyl)thio)-7-(2-(4-methylpiperazin-1-yl)ethoxy)-5-((tetrahydro-2H-pyran-4-yl)oxy)quinazoline

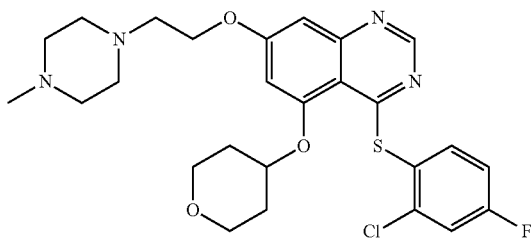

Following the procedure as described in Example 3, replacing 2-chloro-4-fluorophenol with 2-chloro-4-fluorothiophenol to react with 4-chloro-7-(2-(4-methylpiperazin-1-yl)ethoxy)-5-((tetrahydro-2H-pyran-4-yl)oxy)quinazoline, the title compound was obtained as a gum in 86% yield. $^1$H NMR (300 MHz, CDCl$_3$): δ8.58 (s, 1H), 7.68-7.60 (m, 1H), 7.32 (dd, J=8.4, 2.7 Hz, 1H), 7.14-7.04 (m, 1H), 6.85 (d, J=2.4 Hz, 1H), 6.60 (d, J=2.4 Hz, 1H), 4.85-4.75 (m, 1H), 4.30-4.10 (m, 4H), 3.73-3.63 (m, 2H), 2.88 (t, J=5.7 Hz, 2H), 2.70-2.40 (m, 8H), 2.31 (s, 3H), 2.30-2.00 (m, 4H); MS (ES+): m/z 533.4 and 535.4 (M+1).

Example 3.4

Synthesis of 4-(cyclohexyloxy)-7-(2-(4-methylpiperazin-1-yl)ethoxy)-5-((tetrahydro-2H-pyran-4-yl)oxy)quinazoline

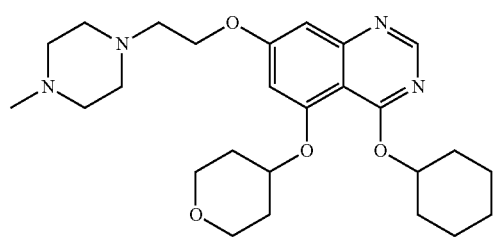 [SMILES: CN1CCN(CCOc2cc(OC3CCOCC3)c3c(OC4CCCCC4)ncnc3c2)CC1]

Following the procedure as described in Example 3, replacing 2-chloro-4-fluorophenol with cyclohexanol to react with 4-chloro-7-(2-(4-methylpiperazin-1-yl)ethoxy)-5-((tetrahydro-2H-pyran-4-yl)oxy)quinazoline, the title compound was obtained as a gum in 10% yield. $^1$H NMR (300 MHz, CDCl$_3$): δ 8.56 (s, 1H), 6.81 (d, J=2.2 Hz, 1H), 6.52 (d, J=2.2 Hz, 1H), 5.45-4.33 (m, 1H), 4.70-4.55 (m, 1H), 4.21 (t, J=5.7 Hz, 2H), 4.10-3.95 (m, 2H), 3.70-3.48 (m, 2H), 2.85 (t, J=5.7 Hz, 2H), 2.70-2.38 (m, 8H), 2.29 (s, 3H), 2.19-2.01 (m, 4H), 2.00-1.70 (m, 4H), 1.70-1.20 (m, 6H); MS (ES+): m/z 471.5 (M+1).

Example 3.5

Synthesis of 2-((7-(2-(4-methylpiperazin-1-yl)ethoxy)-5-((tetrahydro-2H-pyran-4-yl)oxy)quinazolin-4-yl)thio)-4-phenylthiazole

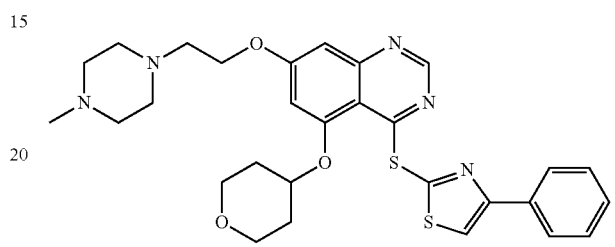

Following the procedure as described in Example 3, replacing 2-chloro-4-fluorophenol with 4-phenylthiazole-2-thiol to react with 4-chloro-7-(2-(4-methylpiperazin-1-yl)ethoxy)-5-((tetrahydro-2H-pyran-4-yl)oxy)quinazoline, the title compound was obtained as a white solid in 36% yield. $^1$H NMR (300 MHz, CDCl$_3$): δ8.80 (s, 1H), 8.03-7.92 (m, 2H), 7.70 (s, 1H), 7.48-7.40 (m, 2H), 7.38-7.31 (m, 1H), 6.89 (d, J=2.2 Hz, 1H), 6.61 (d, J=2.2 Hz, 1H), 4.87-4.67 (m, 1H), 4.30-4.14 (m, 4H), 3.76-3.63 (m, 2H), 2.89 (t, J=5.7 Hz, 2H), 2.72-2.41 (m, 8H), 2.31 (s, 3H), 2.28-2.06 (m, 4H); MS (ES+): m/z 564.4 (M+1).

Example 3.6

Synthesis of 4-(4-bromophenyl)-2-((7-(2-(4-methylpiperazin-1-yl)ethoxy)-5-((tetrahydro-2H-pyran-4-yl)oxy)quinazolin-4-yl)thio)thiazole

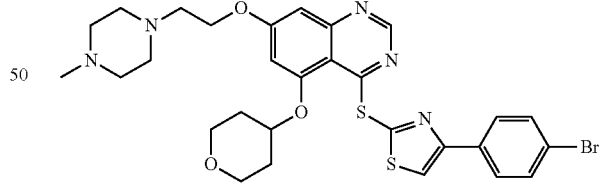

Following the procedure as described in Example 3, replacing 2-chloro-4-fluorophenol with 4-(4-bromophenyl)thiazole-2-thiol to react with 4-chloro-7-(2-(4-methylpiperazin-1-yl)ethoxy)-5-((tetrahydro-2H-pyran-4-yl)oxy)quinazoline, the title compound was obtained as a white solid in 30% yield. $^1$H NMR (300 MHz, CDCl$_3$): δ8.82 (s, 1H), 7.84 (d, J=8.8 Hz, 2H), 7.70 (s, 1H), 7.56 (d, J=8.8 Hz, 2H), 6.90 (d, J=2.4 Hz, 1H), 6.62 (d, J=2.4 Hz, 1H), 4.85-4.72 (m, 1H), 4.29-4.13 (m, 4H), 3.74-3.63 (m, 2H), 2.89 (t, J=5.5 Hz, 2H), 2.73-2.43 (m, 8H), 2.33 (s, 3H), 2.30-2.04 (m, 4H); MS (ES+): m/z 642.3 and 644.3 (M+1).

Example 4

Synthesis of 4-((4-chlorophenyl)thio)-5-(2-methoxyethoxy)-7-(2-(4-methylpiperazin-1-yl)ethoxy)quinazoline

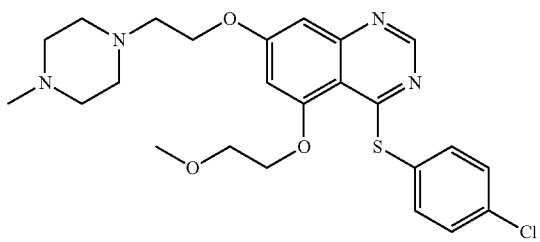 [SMILES: COCCOc1cc(OCCN2CCN(C)CC2)cc2ncnc(Sc3ccc(Cl)cc3)c12]

To a solution of 5-(2-methoxyethoxy)-7-(2-(4-methylpiperazin-1-yl)ethoxy)-quinazolin-4(3H)-one (0.10 g, 0.28 mmol) in 1,2-dichloroethane (10 mL) were added N,N-diisopropylethylamine (0.4 mL) and $POCl_3$ (0.2 mL). The mixture was stirred at room temperature for 2 h and the volatiles were removed in vacuo. The residue was dissolved in 1,2-dimethoxyethane (10 mL), followed by the addition of 4-chloro-benzenethiol (50 mg, 0.39 mmol) and cesium carbonate (0.25 g, 0.77 mmol). The mixture was stirred at reflux for 16 h and dried in vacuo. The residue was purified by column chromatography eluted with 10% methanol in dichloromethane with 1% $NH_4OH$ to afford the title compound as a white solid in 5% yield (7.5 mg). $^1H$ NMR (300 MHz, $CDCl_3$): δ8.59 (s, 1H), 7.51 (d, J=8.4 Hz, 2H), 7.43 (d, J=8.4 Hz, 2H), 6.84 (d, J=2.4 Hz, 1H), 6.59 (d, J=2.4 Hz, 1H), 4.37-4.30 (m, 2H), 4.23 (t, J=5.6 Hz, 2H), 4.00-3.96 (m, 2H), 3.50 (s, 3H), 2.90 (t, J=5.6 Hz, 2H), 2.78-2.67 (m, 4H), 2.67-2.56 (m, 4H), 2.40 (s, 3H); MS (ES+): m/z 489.4 and 491.4 (M+1).

Example 4.1

Synthesis of 4-((4-fluorophenyl)thio)-5-(2-methoxyethoxy)-7-(2-(4-methylpiperazin-1-yl)ethoxy)quinazoline

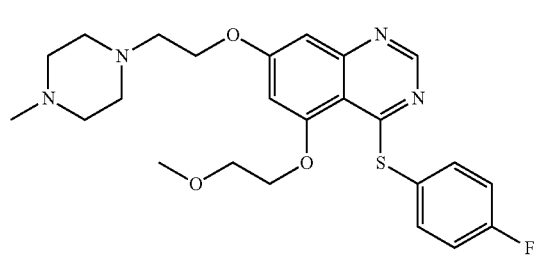 [SMILES: COCCOc1cc(OCCN2CCN(C)CC2)cc2ncnc(Sc3ccc(F)cc3)c12]

Following the procedure as described in Example 4, replacing 4-chloro-benzenethiol with 4-fluorobenzenethiol to react with the corresponding chloride generated from 5-(2-methoxyethoxy)-7-(2-(4-methylpiperazin-1-yl)ethoxy) quinazolin-4(3H)-one, the title compound was obtained as a white solid in 8% yield. $^1H$ NMR (300 MHz, $CDCl_3$): δ8.58 (s, 1H), 7.60-7.50 (m, 2H), 7.20-7.10 (m, 2H), 6.84 (d, J=2.4 Hz, 1H), 6.57 (d, J=2.4 Hz, 1H), 4.36-4.28 (m, 2H), 4.23 (t, J=5.4 Hz, 2H), 4.02-3.94 (m, 2H), 3.53 (s, 3H), 2.89 (t, J=5.4 Hz, 2H), 2.80-2.67 (m, 4H), 2.66-2.52 (m, 4H), 2.38 (s, 3H); MS (ES+): m/z 473.5 (M+1).

Example 4.2

Synthesis of 4-((3,5-dichlorophenyl)thio)-5-(2-methoxyethoxy)-7-(2-(4-methylpiperazin-1-yl)ethoxy)quinazoline

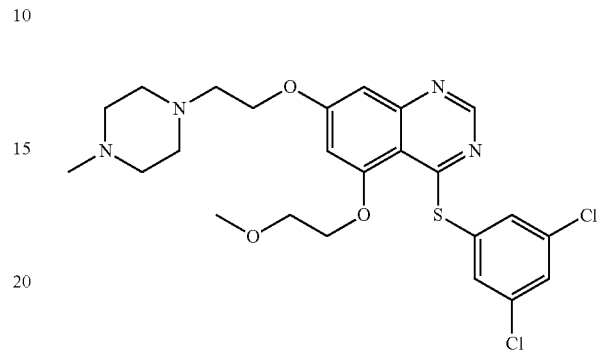

Following the procedure as described in Example 4, replacing 4-chloro-benzenethiol with 3,5-dichlorobenzenethiol to react with the corresponding chloride generated from 5-(2-methoxyethoxy)-7-(2-(4-methylpiperazin-1-yl) ethoxy)quinazolin-4(3H)-one, the title compound was obtained as a white solid in 16% yield. $^1H$ NMR (300 MHz, $CDCl_3$): δ8.59 (s, 1H), 7.47-7.45 (m, 2H), 7.44-7.41 (m, 1H), 6.84 (d, J=2.3 Hz, 1H), 6.58 (d, J=2.3 Hz, 1H), 4.34-4.27 (m, 2H), 4.27 (t, J=5.7 Hz, 2H), 4.00-3.92 (m, 2H), 3.55 (s, 3H), 2.86 (t, J=5.7 Hz, 2H), 2.70-2.58 (m, 4H), 2.57-2.42 (m, 4H), 2.29 (s, 3H); MS (ES+): m/z 523.4, 525.4 and 527.4 (M+1).

Example 4.3

Synthesis of 4-((3,5-difluorophenyl)thio)-5-(2-methoxyethoxy)-7-(2-(4-methylpiperazin-1-yl)ethoxy)quinazoline

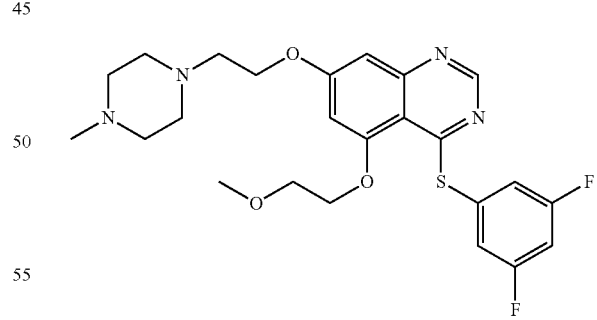

Following the procedure as described in Example 4, replacing 4-chloro-benzenethiol with 3,5-difluorobenzenethiol to react with the corresponding chloride generated from 5-(2-methoxyethoxy)-7-(2-(4-methylpiperazin-1-yl) ethoxy)quinazolin-4(3H)-one, the title compound was obtained as a white solid in 9% yield. $^1H$ NMR (300 MHz, $CDCl_3$): δ8.61 (s, 1H), 7.20-7.10 (m, 2H), 6.96-6.88 (m, 1H), 6.85 (d, J=2.4 Hz, 1H), 6.58 (d, J=2.4 Hz, 1H), 4.36-4.28 (m, 2H), 4.24 (t, J=5.7 Hz, 2H), 4.00-3.92 (m, 2H), 3.52 (s, 3H), 2.88 (t, J=5.7 Hz, 2H), 2.70-2.59 (m, 4H), 2.58-2.42 (m, 4H), 2.31 (s, 3H); MS (ES+): m/z 491.4 (M+1).

Example 4.4

Synthesis of 4-((2,4-dichlorophenyl)thio)-5-(2-methoxyethoxy)-7-(2-(4-methylpiperazin-1-yl)ethoxy)quinazoline

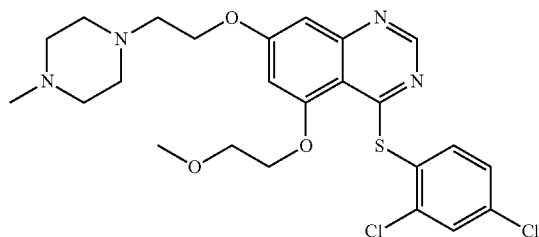 [SMILES: COCCOc1cc(OCCN2CCN(C)CC2)cc2ncnc(Sc3ccc(Cl)cc3Cl)c12]

Following the procedure as described in Example 4, replacing 4-chloro-benzenethiol with 2,4-dichlorobenzenethiol to react with the corresponding chloride generated from 5-(2-methoxyethoxy)-7-(2-(4-methylpiperazin-1-yl)ethoxy)quinazolin-4(3H)-one, the title compound was obtained as a white solid in 8% yield. $^1$H NMR (300 MHz, CDCl$_3$): δ8.58 (s, 1H), 7.62-7.36 (m, 2H), 7.33 (dd, J=6.3, 1.8 Hz, 1H), 6.84 (d, J=1.8 Hz, 1H), 6.58 (d, J=1.8 Hz, 1H), 4.38-4.32 (m, 2H), 4.23 (t, J=5.2 Hz, 2H), 4.02-3.96 (m, 2H), 3.52 (s, 3H), 2.92 (t, J=5.2 Hz, 2H), 2.86-2.72 (m, 8H), 2.50 (s, 3H); MS (ES+): m/z 523.4, 525.4, and 527.4 (M+1).

Example 4.5

Synthesis of 4-((3-bromo-4-fluorophenyl)thio)-5-(2-methoxyethoxy)-7-(2-(4-methylpiperazin-1-yl)ethoxy)quinazoline

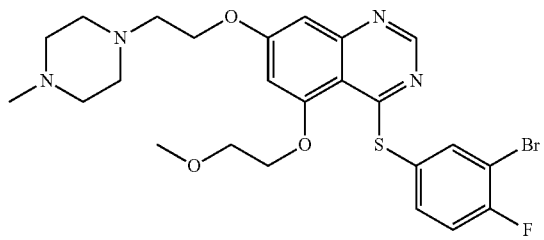 [SMILES: COCCOc1cc(OCCN2CCN(C)CC2)cc2ncnc(Sc3ccc(F)c(Br)c3)c12]

Following the procedure as described in Example 4, replacing 4-chloro-benzenethiol with 3-bromo-4-fluorobenzenethiol to react with the corresponding chloride generated from 5-(2-methoxyethoxy)-7-(2-(4-methylpiperazin-1-yl)ethoxy)-quinazolin-4(3H)-one, the title compound was obtained as a white solid in 8% yield. $^1$H NMR (300 MHz, CDCl$_3$): δ8.60 (s, 1H), 7.77 (dd, J=6.6, 2.1 Hz, 1H), 7.53-7.45 (m, 1H), 7.24-7.17 (m, 1H), 6.85 (d, J=2.1 Hz, 1H), 6.58 (d, J=2.1 Hz, 1H), 4.36-4.28 (m, 2H), 4.24 (t, J=5.7 Hz, 2H), 4.00-3.94 (m, 2H), 3.52 (s, 3H), 2.88 (t, J=5.7 Hz, 2H), 2.70-2.59 (m, 4H), 2.58-2.44 (m, 4H), 2.31 (s, 3H); MS (ES+): m/z 551.3 and 553.3 (M+1).

Example 4.6

Synthesis of 4-((5-(2-methoxyethoxy)-7-(2-(4-methylpiperazin-1-yl)ethoxy)quinazolin-4-yl)thio)benzoic acid

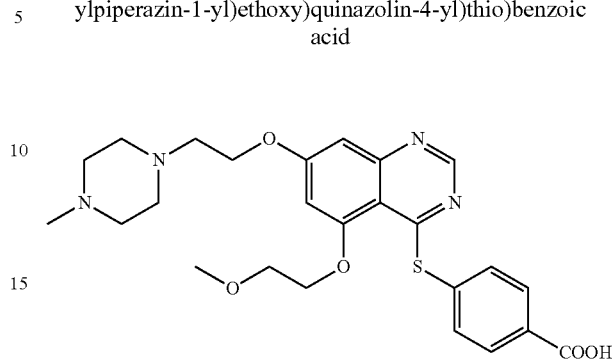

Following the procedure as described in Example 4, replacing 4-chloro-benzenethiol with 4-mercaptobenzoic acid to react with the corresponding chloride generated from 5-(2-methoxyethoxy)-7-(2-(4-methylpiperazin-1-yl)ethoxy)quinazolin-4(3H)-one, the title compound was obtained as a white solid in 27% yield. $^1$H NMR (300 MHz, CDCl$_3$): δ8.58 (s, 1H), 8.03 (d, J=8.1 Hz, 2H), 7.58 (d, J=8.1 Hz, 2H), 6.88 (d, J=2.2 Hz, 1H), 6.56 (d, J=2.2 Hz, 1H), 4.30-4.16 (m, 4H), 3.98-3.89 (m, 2H), 3.54 (s, 3H), 3.08-3.00 (m, 2H), 2.95-2.84 (m, 8H), 2.61 (s, 3H); MS (ES+): m/z 499.4 (M+1).

Example 4.7

Synthesis of 4-(2-chloro-4-fluorophenoxy)-7-((1-methylpiperidin-4-yl)methoxy)-5-((tetrahydro-2H-pyran-4-yl)oxy)quinazoline

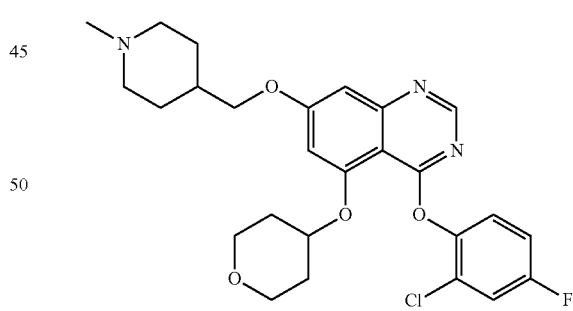

Following the procedure as described in Example 4, replacing 4-chloro-benzenethiol with 2-chloro-4-fluorophenol to react with the corresponding chloride generated from 7-((1-methylpiperidin-4-yl)methoxy)-5-((tetrahydro-2H-pyran-4-yl)oxy)-quinazolin-4(3H)-one, the title compound was obtained as a white solid in 8% yield. $^1$H NMR (300 MHz, CDCl$_3$): δ8.54 (s, 1H), 7.30-7.21 (m, 2H), 7.14-7.04 (m, 1H), 6.91 (d, J=2.1 Hz, 1H), 6.59 (d, J=2.1 Hz, 1H), 4.85-4.74 (m, 1H), 4.05-3.92 (m, 4H), 3.75-3.60 (m, 2H), 2.98-2.87 (m, 2H), 2.32 (s, 3H), 2.13-1.82 (m, 9H), 1.62-1.45 (m, 2H); MS (ES): m/z 502.4 and 504.4 (M+1).

Example 4.8

Synthesis of 4-(3-((4-(2-chloro-4-fluorophenoxy)-5-morpholinoquinazolin-7-yl)oxy)propyl)morpholine

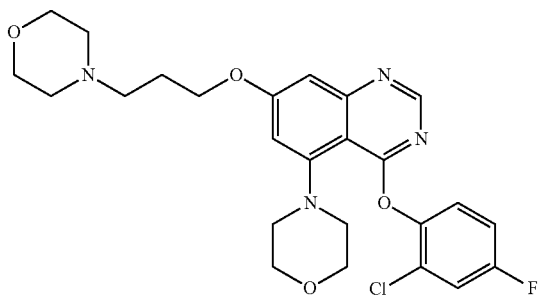 [SMILES: Fc1ccc(Oc2ncnc3cc(OCCCN4CCOCC4)cc(N4CCOCC4)c23)c(Cl)c1]

Following the procedure as described in Example 4, replacing 4-chloro-benzenethiol with 2-chloro-4-fluorophenol to react with the corresponding chloride generated from 5-morpholino-7-(3-morpholinopropoxy)quinazolin-4(3H)-one, the title compound was obtained as a white solid in 10% yield. $^1$H NMR (300 MHz, CDCl$_3$): δ8.52 (s, 1H), 7.33-7.24 (m, 1H), 7.19-7.06 (m, 2H), 7.01 (d, J=2.4 Hz, 1H), 6.70 (d, J=2.4 Hz, 1H), 4.20 (t, J=6.3 Hz, 2H), 3.92-3.70 (m, 8H), 3.22 (br s, 4H), 2.66-2.44 (m, 6H), 2.16-2.02 (m, 2H); MS (ES+): m/z 503.3 and 505.3 (M+1).

Example 4.9

Synthesis of 4-(3-((4-(2-chloro-4-fluorophenoxy)-5-(4-methylpiperazin-1-yl)quinazolin-7-yl)oxy)propyl)morpholine

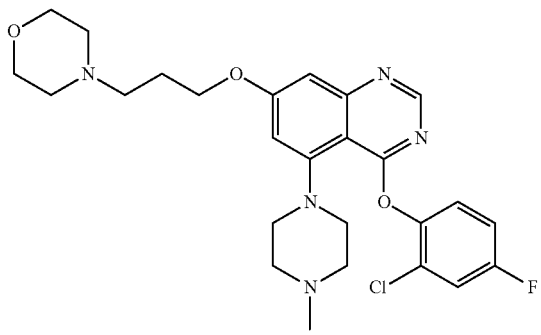 [SMILES: CN1CCN(c2cc(OCCCN3CCOCC3)cc3ncnc(Oc4ccc(F)cc4Cl)c23)CC1]

Following the procedure as described in Example 4, replacing 4-chloro-benzenethiol with 2-chloro-4-fluorophenol to react with the corresponding chloride generated from 5-(4-methylpiperazin-1-yl)-7-(3-morpholinopropoxy)quinazolin-4(3H)-one, the title compound was obtained as a yellow oil in 18% yield. $^1$H NMR (300 MHz, CDCl$_3$): δ8.55 (s, 1H), 7.38-7.31 (m, 1H), 7.25-7.10 (m, 2H), 7.03 (d, J=2.1 Hz, 1H), 6.75 (d, J=2.1 Hz, 1H), 4.23 (t, J=6.3 Hz, 2H), 3.84-3.72 (m, 6H), 3.10 (br s, 2H), 2.80 (br s, 2H), 2.64-2.50 (m, 8H), 2.37 (s, 3H), 2.16-2.02 (m, 2H); MS (ES+): m/z 516.4 and 518.4 (M+1).

Example 4.10

Synthesis of 7-((1-methylpiperidin-4-yl)methoxy)-5-((tetrahydro-2H-pyran-4-yl)oxy)-4-(3-(trifluoromethyl)phenoxy)quinazoline

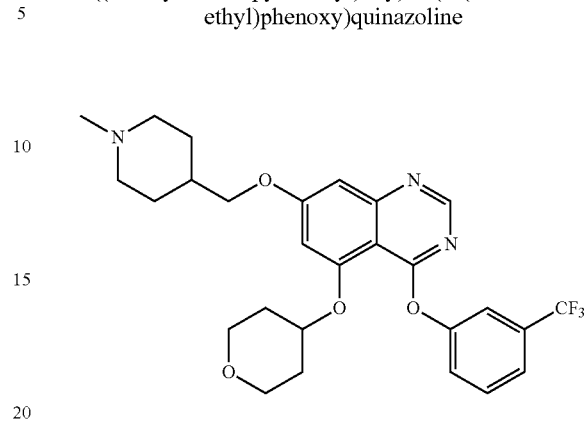

Following the procedure as described in Example 4, replacing 4-chloro-benzenethiol with 3-(trifluoromethyl)phenol to react with the corresponding chloride generated from 7-(2-(1-methyl-piperidin-4-yl)ethoxy)-5-((tetrahydro-2H-pyran-4-yl)oxy)-quinazolin-4(3H)-one, the title compound was obtained as a colorless foamy solid in 5% yield. $^1$H NMR (400 MHz, CDCl$_3$): δ8.56 (s, 1H), 7.62-7.54 (m, 2H), 7.52-7.48 (m, 1H), 7.44-7.40 (m, 1H), 6.91 (d, J=2.4 Hz, 1H), 6.59 (d, J=2.0 Hz, 1H), 4.80-4.75 (m, 1H), 4.03-3.95 (m, 4H), 3.70-3.62 (m, 2H), 3.08-2.97 (m, 2H), 2.37 (s, 3H), 2.35-2.25 (m, 2H), 2.15-2.04 (m, 4H), 1.95-1.75 (m, 3H), 1.70-1.55 (m, 2H); MS (ES+): m/z 518.4 (M+1).

Example 4.11

Synthesis of 7-((1-methylpiperidin-4-yl)methoxy)-5-((tetrahydro-2H-pyran-4-yl)oxy)-4-(4-(trifluoromethyl)phenoxy)quinazoline

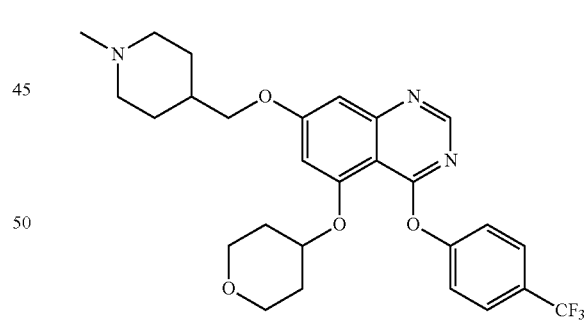

Following the procedure as described in Example 4, replacing 4-chloro-benzenethiol with 4-(trifluoromethyl)phenol to react with the corresponding chloride generated from 7-(2-(1-methyl-piperidin-4-yl)ethoxy)-5-((tetrahydro-2H-pyran-4-yl)oxy)-quinazolin-4(3H)-one, the title compound was obtained as a yellowish foamy solid in 3% yield. $^1$H NMR (400 MHz, CDCl$_3$): δ8.57 (s, 1H), 7.73 (d, J=8.4 Hz, 2H), 7.34 (d, J=8.4 Hz, 2H), 6.91 (d, J=2.0 Hz, 1H), 6.59 (d, J=2.0 Hz, 1H), 4.82-4.75 (m, 1H), 4.03-3.95 (m, 4H), 3.70-3.62 (m, 2H), 3.08-2.97 (m, 2H), 2.37 (s, 3H), 2.32-2.20 (m, 2H), 2.15-2.04 (m, 4H), 1.95-1.73 (m, 3H), 1.65-1.55 (m, 2H); MS (ES+): m/z 518.4 (M+1).

Example 5

Synthesis of (R)-3-((4-(2-chloro-4-fluorophenoxy)-5-((tetrahydro-2H-pyran-4-yl)oxy)quinazolin-7-yl)oxy)propane-1,2-diol

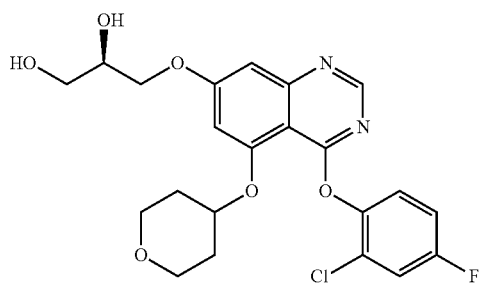 [SMILES: OC[C@@H](O)COc1cc(OC2CCOCC2)c2c(Oc3ccc(F)cc3Cl)ncnc2c1]

To a mixture of (S)-4-(2-chloro-4-fluorophenoxy)-7-((2,2-dimethyl-1,3-dioxolan-4-yl)methoxy)-5-((tetrahydro-2H-pyran-4-yl)oxy)quinazoline (33 mg, 0.07 mmol) in 5 mL of methanol was added 2 mL of 15% p-toluenesulfonic acid in 1:1 water/methanol mixture. The mixture was heated at 50° C. for 10 min. After removal of the volatiles in vacuo, the residue was neutralized by sodium bicarbonate and extracted with ethyl acetate (3×10 mL). The organic layers were collected, dried over sodium sulfate and filtered. The filtrate was dried in vacuo and the crude product was purified by preparative thin layer chromatography using 5% methanol in dichloromethane to afford the title compound as a white solid in 50% yield (15 mg). $^1$H NMR (300 MHz, CDCl$_3$): δ 8.58 (s, 1H), 7.36-7.22 (m, 2H), 7.18-7.08 (m, 1H), 7.01 (d, J=2.1 Hz, 1H), 6.67 (d, J=2.1 Hz, 1H), 4.87-4.76 (m, 1H), 4.32-4.20 (m, 3H), 4.10-3.80 (m, 4H), 3.76-3.62 (m, 2H), 3.20-2.80 (br s, 2H), 2.18-2.00 (m, 2H), 2.00-1.90 (m, 2H); MS (ES+): m/z 464.1 and 466.1 (M+1).

Example 6

Synthesis of 4-isopropoxy-7-((1-methylpiperidin-4-yl)methoxy)-5-((tetrahydro-2H-pyran-4-yl)oxy)quinazoline

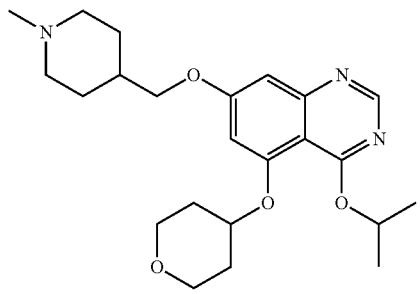 [SMILES: CC(C)Oc1ncnc2cc(OCC3CCN(C)CC3)cc(OC3CCOCC3)c12]

To a solution of 7-((1-methylpiperidin-4-yl)methoxy)-5-(tetrahydro-2H-pyran-4-yloxy)quinazolin-4(3H)-one (0.05 g, 0.13 mmol) in 5 mL of isopropanol was added 0.1 mL of 5N HCl in isopropanol. The mixture was refluxed for 2 h. After removal of solvent in vacuo, the residue was purified by column chromatography eluted with 0.5:5:94.5 NH$_4$OH:methanol:dichloromethane to afford the title compound as a white foam in 39% yield (21 mg). $^1$H NMR (400 MHz, CDCl$_3$): δ 8.57 (s, 1H), 6.80 (d, J=2.4 Hz, 1H), 6.46 (d, J=2.0 Hz, 1H), 5.70-5.60 (m, 1H), 4.67-4.60 (m, 1H), 4.10-4.00 (m, 2H), 3.93 (d, J=6.0 Hz, 2H), 3.70-3.64 (m, 2H), 2.95-2.88 (m, 2H), 2.30 (3H), 2.13-1.95 (m, 4H), 1.95-1.80 (m, 5H), 1.56-1.48 (m, 2H), 1.45 (s, 3H), 1.43 (s, 3H).

Example 7

Synthesis of N$^7$-(2-(diethylamino)ethyl)-5-((tetrahydro-2H-pyran-4-yl)oxy)-N$^4$-(4-(trifluoromethyl)thiazol-2-yl)quinazoline-4,7-diamine

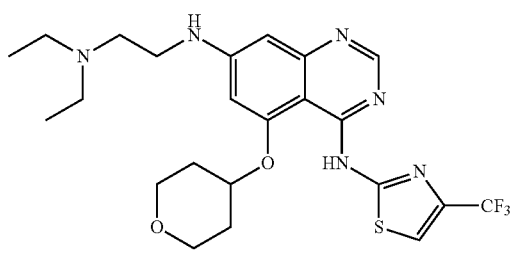 [SMILES: CCN(CC)CCNc1cc(OC2CCOCC2)c2c(Nc3nc(C(F)(F)F)cs3)ncnc2c1]

To a solution of 7-fluoro-5-(tetrahydro-2H-pyran-4-yloxy)quinazolin-4(3H)-one (0.50 g, 1.90 mmol) in 20 mL of 1,2-dichloroethane was added N,N-diisopropylethylamine (1.65 mL, 9.50 mmol), followed by addition of POCl$_3$ (0.35 mL, 3.80 mmol). The resulting mixture was refluxed for 2 h. After removal of the solvent and excess POCl$_3$ in vacuo, the residue was dissolved in 5 mL of dichloroethane and 4-(trifluoromethyl)thiazol-2-amine (0.47 g, 2.85 mmol) was added. The mixture was refluxed for 3 h. After removal of the solvent, the residue was purified by column chromatography eluted with 30:70 ethyl acetate:hexane to afford 7-fluoro-N-(4-(trifluoromethyl)thiazol-2-yl)-5-(tetrahydro-2H-pyran-4-yloxy)quinazolin-4-amine as a white solid in 19% yield (0.14 g). $^1$H NMR (400 MHz, CDCl$_3$): δ 8.83 (s, 1H), 7.45 (s, 1H), 7.26 (dd, J=9.6, 2.0 Hz, 1H), 6.78 (dd, J=9.6, 2.0 Hz, 1H), 4.92-4.84 (m, 1H), 4.19-4.10 (m, 2H), 3.78-3.50 (m, 2H), 2.34-3.26 (m, 2H), 2.18-2.08 (m, 2H).

A solution of 7-fluoro-N-(4-(trifluoromethyl)thiazol-2-yl)-5-(tetrahydro-2H-pyran-4-yloxy)quinazolin-4-amine (60 mg, 0.14 mmol) in 1 mL of N$^1$,N$^1$-diethylethane-1,2-diamine was heated at 110° C. overnight. The solvent was removed in vacuo and the residue was purified by column chromatography eluted with 0.5:5:94.5 NH$_4$OH:methanol:dichloromethane to afford the title compound as a yellowish solid in 35% yield (25 mg). $^1$H NMR (400 MHz, CDCl$_3$): δ 11.04 (br s, 1H), 8.64 (s, 1H), 7.36 (s, 1H), 6.51 (d, J=2.0 Hz, 1H), 6.32 (d, J=2.0 Hz, 1H), 5.46 (br s, 1H), 4.86-4.78 (m, 1H), 4.18-4.08 (m, 2H), 3.76-3.68 (m, 2H), 3.35-3.26 (m, 2H), 2.88-2.80 (m, 2H), 2.68 (q, J=7.2 Hz, 4H), 2.30-2.20 (m, 2H), 2.15-2.00 (m, 2H), 1.11 (t, J=7.2 Hz, 6H); MS (ES+): m/z 511.4 (M+1).

Example 8

Synthesis of 7-((1-methylpiperidin-4-yl)methoxy)-5-((tetrahydro-2H-pyran-4-yl)oxy)-N-(1H-1,2,4-triazol-5-yl)quinazolin-4-amine

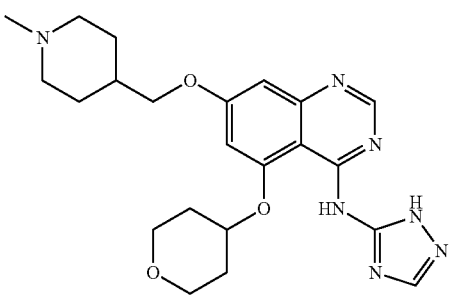 [SMILES: CN1CCC(COc2cc(OC3CCOCC3)c3c(Nc4ncn[nH]4)ncnc3c2)CC1]

To a solution of 7-((1-methylpiperidin-4-yl)methoxy)-5-(tetrahydro-2H-pyran-4-yloxy)quinazolin-4(3H)-one (0.10 g, 0.27 mmol) in 5 mL of 1,2-dichloroethane was added N,N-diisopropylethylamine (0.23 mL, 1.34 mmol), followed by the addition of $POCl_3$ (0.05 mL, 0.54 mmol). The mixture was refluxed for 2 h. After removal of solvent and excess $POCl_3$ in vacuo, the residue was dissolved in 5 mL of 1,2-dichloroethane and 2H-1,2,4-triazol-3-amine (0.05 mL, 0.54 mmol) was added, followed by the addition of 0.1 mL of 4 N HCl in dioxane. The mixture was refluxed overnight. After removal of solvent in vacuo, the residue was purified by column chromatography eluted with 0.5:5:94.5 $NH_4OH$:methanol:dichloromethane to afford the title compound as a yellowish solid in 29% yield (34 mg). $^1H$ NMR (400 MHz, $CDCl_3$): δ10.70 (br s, 1H), 8.68 (s, 1H), 7.78 (s, 1H), 6.88 (d, J=2.4 Hz, 1H), 6.57 (d, J=2.4 Hz, 1H), 4.85-4.76 (m, 1H), 4.1-4.05 (m, 2H), 3.96 (d, J=5.6 Hz, 2H), 3.73-3.65 (m, 2H), 2.96-2.87 (m, 2H), 2.32-2.23 (m, 5H), 2.10-1.97 (m, 4H), 1.90-1.78 (m, 3H), 1.60-1.48 (m, 2H); MS (ES+): m/z 440.4 (M+1).

Biological Examples

Example 9

Kinase Enzymatic Activity Assays

Preparation of Active Recombinant Kinase Proteins:

Recombinant human Tyro3 (455-end, the gene accession number NM_006293), human Axl (473-end, the gene accession number NM_021913) and human Mer (578-872, the gene accession number NM_006343) were independently expressed by baculovirus in Sf9 insect cells using an N-terminal GST tag. The recombinant proteins were stored at −70° C. in a medium containing 50 mM Tris-HCl, pH 7.5, 150 mM NaCl, 10 mM glutathione, 0.1 mM EDTA, 0.25 mM DTT, 0.1 mM PMSF and 25% glycerol. The recombinant proteins were aliquoted into smaller quantities after centrifugation to avoid repeated handling and multiple freeze/thaw cycles for the most favorable performance.

Preparation of Assay Reagents:

Kinase Assay Buffer: This buffer solution consisted of the following components: 25 mM MOPS, pH 7.2, 12.5 mM β-glycerol-phosphate, 25 mM $MgCl_2$, 5 mM EGTA, 2 mM EDTA and DTT 0.25 mM which was added prior to use.

Kinase Dilution Buffer: Kinase Assay Buffer was diluted at a 1:4 ratio (5× dilution) with distilled water.

$[^{33}P]$-ATP assay cocktail: In a designated radioactive working area, a 250 μM $[^{33}P]$-ATP assay cocktail was prepared by the addition of the following components: 150 μL of 10 mM ATP stock solution, 100 μL $[^{33}P]$-ATP (1 mci/100 μL), and 5.75 mL of kinase assay buffer. This solution was stored in 1 mL aliquots at −20° C.

ATP stock solution (10 mM): The ATP stock solution was prepared by dissolving 55 mg of ATP in 10 mL of kinase assay buffer. It was stored in 200 μL aliquots at −20° C.

Active Kinase Stock Solution: The active recombinant kinase protein (0.1 μg/μL) was diluted with Kinase Dilution Buffer and the activity was assayed using a serial dilution method. The specific activity is expressed in nmoL/min/mg.

Substrates: poly(4:1 glu:tyr) is the substrate used for each kinase Tyro3, Axl and Mer. The peptide substrate was dissolved in water to give the final concentration of 1 mg/mL.

Test compound solution: Test compound was dissolved in DMSO to obtain a 10 mM solution. The assay solution was prepared by adding 5 μL of this solution to 955 μL of 10% DMSO/water to obtain the final concentration of 50 μM.

Assay Procedure:

The enzymatic activity of all three kinases was determined as follows. Using a 96-well plate, the wells were divided into three categories: Blank wells, Background wells and Test wells. In Test wells, 5 μL of the test compound solution and 5 μL of the substrate solution were added. In Control wells, 5 μL of 10% DMSO/water and 5 μL of the substrate solution were added. In Blank wells, 10 μL of 10% DMSO/water was added. To each well was added 10 μL of Active Kinase Stock Solution to make up the volume in each well to 20 μL. All test samples, controls and blanks were run in duplicate. The reaction was initiated by the addition of 5 μL of $[^{33}P]$-ATP assay cocktail, bringing the final volume up to 25 μL in every well. The mixture was incubated at room temperature for 30 minutes. The reaction was terminated by transferring 10 μL of the reaction mixture into a Millipore MultiScreen filter plate (cat. number MSPHN6B50). The filter plate was washed in a 1% phosphoric acid solution with constant gentle shaking for 15 minutes and this step was repeated once. After the plate was dried in air, scintillation fluid was added to each well and the radioactivity in each well in CPM was counted by a Microbeta TriLux. The corrected CPM in each test well was determined by subtracting the average value of Blank well values. Percentage of inhibition of the kinase enzymatic activity by the test compound was determined using the following formula:

$$\% \text{ Inhibition} = \left(1 - \frac{\text{Average of corrected } CPM \text{ in Test wells}}{\text{Average of corrected } CPM \text{ in Control wells}}\right) \times 100$$

The $IC_{50}$ values were determined in a similar way following a serial dilution of the test compound. The percentage of inhibition at each concentration was calculated following the above formula. The $IC_{50}$ was estimated from the curve of % Inhibition against Concentration in log unit using Prism 5, version 5.01.

The following Table summarizes the inhibitory activity on Tyro3, Axl and Mer of the compounds of the invention. "+" indicates that the $IC_{50}$ is >10 μM; "++" indicates 1 μM<$IC_{50}$<10 μM; "+++" indicates 0.5 μM<$IC_{50}$<1 μM and "++++" indicates that the $IC_{50}$<0.5 μM.

| No. | Chemical Name | IC$_{50}$ TYRO3 | AXL | MER |
|---|---|---|---|---|
| 1 | 4-(2-chloro-4-fluorophenoxy)-7-(2-(piperidin-1-yl)ethoxy)-5-((tetrahydro-2H-pyran-4-yl)oxy)quinazoline | ++++ | ++ | ++++ |
| 2 | 4-(2-chloro-4-fluorophenoxy)-7-(2-(1-methylpiperidin-4-yl)ethoxy)-5-((tetrahydro-2H-pyran-4-yl)oxy)quinazoline | ++++ | ++ | ++++ |
| 2.1 | 4-(2-((4-(2-chloro-4-fluorophenoxy)-5-((tetrahydro-2H-pyran-4-yl)oxy)quinazolin-7-yl)oxy)ethyl)morpholine | ++ | ++ | +++ |
| 2.2 | 2-(2-((4-(2-chloro-4-fluorophenoxy)-5-((tetrahydro-2H-pyran-4-yl)oxy)quinazolin-7-yl)oxy)ethoxy)-N,N-dimethylethanamine | ++++ | ++ | ++++ |
| 2.3 | 2-((4-(2-chloro-4-fluorophenoxy)-5-((tetrahydro-2H-pyran-4-yl)oxy)quinazolin-7-yl)oxy)-N-(2-methoxyethyl)-N-methylethanamine | +++ | + | ++ |
| 2.4 | 4-(2-chloro-4-fluorophenoxy)-7-(2-(2-methoxyethoxy)ethoxy)-5-((tetrahydro-2H-pyran-4-yl)oxy)quinazoline | ++ | + | ++ |
| 2.5 | 4-(3-((4-(2-chloro-4-fluorophenoxy)-5-((tetrahydro-2H-pyran-4-yl)oxy)quinazolin-7-yl)oxy)propyl)morpholine | ++++ | +++ | ++++ |
| 2.9 | (S)-4-(2-chloro-4-fluorophenoxy)-7-((2,2-dimethyl-1,3-dioxolan-4-yl)methoxy)-5-((tetrahydro-2H-pyran-4-yl)oxy)quinazoline | ++ | ++ | ++ |
| 2.10 | 4-(2-chloro-4-fluorophenoxy)-7-(4-(2-methoxyethyl)piperazin-1-yl)-5-((tetrahydro-2H-pyran-4-yl)oxy)quinazoline | ++++ | ++ | +++ |
| 2.12 | 4-(2-chloro-4-fluorophenoxy)-5-methoxy-7-(2-(4-methylpiperazin-1-yl)ethoxy)quinazoline | ++++ | ++ | ++ |
| 2.13 | N-(5-methoxy-7-((1-methylpiperidin-4-yl)methoxy)quinazolin-4-yl)-4-(trifluoromethyl)-thiazol-2-amine | + | ++++ | + |
| 2.14 | N-(7-(2-(4-methyl-piperazin-1-yl)ethoxy)-5-((tetrahydro-2H-pyran-4-yl)oxy)quinazolin-4-yl)thiazol-2-amine | ++ | ++++ | ++++ |
| 2.15 | N$^1$-(2-((4-(2-chloro-4-fluorophenoxy)-5-((tetrahydro-2H-pyran-4-yl)oxy)quinazolin-7-yl)oxy)ethyl)-N$^1$,N$^2$,N$^2$-trimethylethane-1,2-diamine | +++ | ++ | +++ |
| 2.16 | 2-(2-((4-methoxy-5-((tetrahydro-2H-pyran-4-yl)oxy)quinazolin-7-yl)oxy)ethoxy)-N,N-dimethylethanamine | ++ | ++++ | + |
| 2.17 | 4-(3-((4-(2-chloro-4-fluorophenoxy)-5-methoxyquinazolin-7-yl)oxy)propyl)morpholine | ++++ | ++ | ++ |
| 2.18 | N-(7-(3-morpholino-propoxy)-5-((tetrahydro-2H-pyran-4-yl)oxy)-quinazolin-4-yl)-4-(trifluoromethyl)thiazol-2-amine | + | +++ | ++ |
| 2.19 | N-(7-(3-morpholinopropoxy)-5-((tetrahydro-2H-pyran-4-yl)oxy)quinazolin-4-yl)-1,3,4-thiadiazol-2-amine | ++ | ++++ | ++ |
| 2.20 | 5-methyl-N-(7-(3-morpholinopropoxy)-5-((tetrahydro-2H-pyran-4-yl)oxy)quinazolin-4-yl)-1,3,4-thiadiazol-2-amine | + | ++ | ++ |
| 2.21 | N-(7-(3-morpholinopropoxy)-5-((tetrahydro-2H-pyran-4-yl)oxy)quinazolin-4-yl)thiazol-2-amine | ++ | ++++ | ++++ |
| 2.22 | N-(7-(3-morpholino-propoxy)-5-((tetrahydro-2H-pyran-4-yl)oxy)-quinazolin-4-yl)-5-(trifluoromethyl)-1,3,4-thiadiazol-2-amine | + | ++ | + |
| 2.23 | N-(7-((1-methylpiperidin-4-yl)methoxy)-5-((tetrahydro-2H-pyran-4-yl)oxy)quinazolin-4-yl)-4-(trifluoromethyl)thiazol-2-amine | + | ++++ | + |
| 2.24 | N-(5-methoxy-7-morpholinoquinazolin-4-yl)-4-(trifluoromethyl)-thiazol-2-amine | + | ++ | + |
| 2.25 | N-(5-methoxy-7-(4-methylpiperazin-1-yl)quinazolin-4-yl)-4-(trifluoromethyl)thiazol-2-amine | + | +++ | + |
| 2.26 | methyl 3-((5-methoxy-7-(3-morpholinopropoxy)quinazolin-4-yl)oxy)benzoate | ++ | + | + |
| 2.27 | methyl 2-(3-((5-methoxy-7-(3-morpholinopropoxy)-quinazolin-4-yl)oxy)phenyl)acetate | ++ | + | ++ |
| 2.28 | N-benzyl-3-((5-methoxy-7-(3-morpholinopropoxy)-quinazolin-4-yl)oxy)benzamide | + | + | + |
| 2.29 | N-benzyl-2-(3-((5-methoxy-7-(3-morpholinopropoxy)-quinazolin-4-yl)oxy)-phenyl)acetamide | ++ | + | + |
| 2.30 | methyl 3-((7-(2-(4-methylpiperazin-1-yl)ethoxy)-5-((tetrahydro-2H-pyran-4-yl)oxy)quinazolin-4-yl)oxy)benzoate | ++ | ++ | + |
| 2.31 | methyl 2-(3-((7-(2-(4-methylpiperazin-1-yl)ethoxy)-5-((tetrahydro-2H-pyran-4-yl)oxy)quinazolin-4-yl)oxy)phenyl)acetate | +++ | ++ | + |
| 2.32 | N-benzyl-3-((7-(2-(4-methylpiperazin-1-yl)ethoxy)-5-((tetrahydro-2H-pyran-4-yl)oxy)quinazolin-4-yl)oxy)benzamide | + | ++ | + |
| 2.33 | N-benzyl-2-(3-((7-(2-(4-methylpiperazin-1-yl)ethoxy)-5-((tetrahydro-2H-pyran-4-yl)oxy)quinazolin-4-yl)oxy)phenyl)acetamide | +++ | ++ | + |
| 2.34 | 4-(2-chloro-4-fluorophenoxy)-5-methoxy-7-((1-methylpiperidin-4-yl)methoxy)quinazoline | ++++ | ++ | +++ |
| 2.35 | 3-methyl-N-(7-(3-morpholinopropoxy)-5-((tetrahydro-2H-pyran-4-yl)oxy)quinazolin-4-yl)isoxazol-5-amine | + | ++ | ++ |
| 2.36 | 5-methyl-N-(7-((1-methylpiperidin-4-yl)methoxy)-5-((tetrahydro-2H-pyran-4-yl)oxy)quinazolin-4-yl)-1,3,4-thiadiazol-2-amine | + | ++ | ++ |
| 2.37 | N-(7-((1-methylpiperidin-4-yl)methoxy)-5-((tetrahydro-2H-pyran-4-yl)oxy)quinazolin-4-yl)-5-(trifluoromethyl)-1,3,4-thiadiazol-2-amine | + | ++ | + |
| 2.38 | N-(7-((1-methylpiperidin-4-yl)methoxy)-5-((tetrahydro-2H-pyran-4-yl)oxy)quinazolin-4-yl)-1,3,4-thiadiazol-2-amine | ++ | ++++ | +++ |
| 2.39 | N-(7-((1-methylpiperidin-4-yl)methoxy)-5-((tetrahydro-2H-pyran-4-yl)oxy)quinazolin-4-yl)thiazol-2-amine | +++ | ++++ | ++++ |
| 2.40 | 3-methyl-N-(7-((1-methylpiperidin-4-yl)methoxy)-5-((tetrahydro-2H-pyran-4-yl)oxy)quinazolin-4-yl)isoxazol-5-amine | ++ | ++++ | ++ |
| 2.41 | N-(7-(4-(2-methoxyethyl)piperazin-1-yl)-5-((tetrahydro-2H-pyran-4-yl)oxy)quinazolin-4-yl)-4-(trifluoromethyl)-thiazol-2-amine | + | ++ | + |
| 2.42 | 4-methyl-N-(7-((1-methylpiperidin-4-yl)methoxy)-5-((tetrahydro-2H-pyran-4-yl)oxy)quinazolin-4-yl)thiazol-2-amine | ++ | ++++ | ++++ |
| 2.43 | 5-methyl-N-(7-((1-methylpiperidin-4-yl)methoxy)-5-((tetrahydro-2H-pyran-4-yl)oxy)quinazolin-4-yl)thiazol-2-amine | ++ | ++++ | ++++ |
| 2.44 | N-(7-(4-(2-(dimethylamino)ethyl)piperidin-1-yl)-5-((tetrahydro-2H-pyran-4-yl)oxy)quinazolin-4-yl)-4-(trifluoromethyl)-thiazol-2-amine | ++ | ++++ | ND |
| 2.45 | N-(7-(2-(1-methylpiperidin-4-yl)ethoxy)-5-((tetrahydro-2H-pyran-4-yl)oxy)quinazolin-4-yl)-4-(trifluoromethyl)-thiazol-2-amine | + | ++++ | ++ |

| No. | Chemical Name | IC50 TYRO3 | AXL | MER |
|---|---|---|---|---|
| 2.47 | 2-((7-((1-methylpiperidin-4-yl)methoxy)-5-((tetrahydro-2H-pyran-4-yl)oxy)quinazolin-4-yl)thio)-1,3,4-thiadiazole | ++ | ++++ | ++ |
| 2.48 | 2-methyl-5-((7-((1-methylpiperidin-4-yl)methoxy)-5-((tetrahydro-2H-pyran-4-yl)oxy)quinazolin-4-yl)thio)-1,3,4-thiadiazole | + | +++ | + |
| 2.49 | 4,5-dimethyl-2-((7-((1-methylpiperidin-4-yl)methoxy)-5-((tetrahydro-2H-pyran-4-yl)oxy)quinazolin-4-yl)thio)oxazole | ++ | + | + |
| 2.50 | 2-((7-((1-methylpiperidin-4-yl)methoxy)-5-((tetrahydro-2H-pyran-4-yl)oxy)quinazolin-4-yl)thio)-4-(trifluoromethyl)thiazole | + | +++ | ++ |
| 2.51 | 4-methyl-2-((7-((1-methylpiperidin-4-yl)methoxy)-5-((tetrahydro-2H-pyran-4-yl)oxy)quinazolin-4-yl)thio)thiazole | ++++ | ++++ | ++ |
| 2.52 | 2-((7-((1-methylpiperidin-4-yl)methoxy)-5-((tetrahydro-2H-pyran-4-yl)oxy)quinazolin-4-yl)thio)thiazole | ++++ | ++++ | ++++ |
| 2.53 | N-(7-(2-morpholinoethoxy)-5-((tetrahydro-2H-pyran-4-yl)oxy)quinazolin-4-yl)-4-(trifluoromethyl)thiazol-2-amine | + | ++ | + |
| 2.54 | N-(7-(3-(dimethylamino)propoxy)-5-((tetrahydro-2H-pyran-4-yl)oxy)quinazolin-4-yl)-4-(trifluoromethyl)thiazol-2-amine | + | ++++ | ++ |
| 2.55 | (R)-3-((5-((tetrahydro-2H-pyran-4-yl)oxy)-4-((4-(trifluoromethyl)thiazol-2-yl)amino)quinazolin-7-yl)oxy)propane-1,2-diol | + | +++ | + |
| 2.56 | N-(7-(2-(2-(dimethylamino)ethoxy)ethoxy)-5-((tetrahydro-2H-pyran-4-yl)oxy)quinazolin-4-yl)-4-(trifluoromethyl)-thiazol-2-amine | + | ++++ | ++ |
| 2.57 | N-(7-(4-(2-(dimethyl-amino)ethyl)piperazin-1-yl)-5-((tetrahydro-2H-pyran-4-yl)oxy)-quinazolin-4-yl)-4-(trifluoromethyl)-thiazol-2-amine | ++ | ++++ | ++ |
| 2.58 | N-(7-((1-methylpiperidin-4-yl)methoxy)-5-((tetrahydro-2H-pyran-4-yl)oxy)quinazolin-4-yl)-3-(trifluoromethyl)-isoxazol-5-amine | + | +++ | ++ |
| 2.59 | N7-(3-(dimethylamino)-propyl)-N7-methyl-5-((tetrahydro-2H-pyran-4-yl)oxy)-N4-(4-(trifluoromethyl)thiazol-2-yl)quinazoline-4,7-diamine | + | +++ | + |
| 2.60 | N-(7-(2-(piperidin-1-yl)ethoxy)-5-((tetrahydro-2H-pyran-4-yl)oxy)quinazolin-4-yl)-4-(trifluoromethyl)thiazol-2-amine | + | ++++ | ++++ |
| 2.61 | N-(7-((1-methylpiperidin-4-yl)methoxy)-5-((tetrahydro-2H-pyran-4-yl)oxy)-quinazolin-4-yl)isoxazol-3-amine | ++ | ++++ | ++++ |
| 2.62 | 3-((4-(2-chloro-4-fluorophenoxy)-5-((tetrahydro-2H-pyran-4-yl)oxy)quinazolin-7-yl)oxy)-N,N-dimethylpropan-1-amine | ++++ | ++ | ++++ |
| 2.63 | 4-(2-chloro-4-fluorophenoxy)-7-(3-(4-methylpiperazin-1-yl)propoxy)-5-((tetrahydro-2H-pyran-4-yl)oxy)quinazoline | ++++ | ++++ | ++++ |
| 3 | 4-(2-chloro-4-fluorophenoxy)-7-(2-(4-methylpiperazin-1-yl)ethoxy)-5-((tetrahydro-2H-pyran-4-yl)oxy)quinazoline | +++ | ++ | ++ |
| 3.1 | 4-(2-chloro-4-fluorophenoxy)-7-methoxy-5-((tetrahydro-2H-pyran-4-yl)oxy)quinazoline | +++ | + | +++ |
| 3.2 | 7-(2-(4-methylpiperazin-1-yl)ethoxy)-4-phenoxy-5-((tetrahydro-2H-pyran-4-yl)oxy)quinazoline | ++++ | ++++ | ++ |
| 3.3 | 4-((2-chloro-4-fluorophenyl)thio)-7-(2-(4-methylpiperazin-1-yl)ethoxy)-5-((tetrahydro-2H-pyran-4-yl)oxy)quinazoline | ++++ | + | ++ |
| 3.4 | 4-(cyclohexyloxy)-7-(2-(4-methylpiperazin-1-yl)ethoxy)-5-((tetrahydro-2H-pyran-4-yl)oxy)quinazoline | ++ | +++ | +++ |
| 4 | 4-((4-chlorophenyl)thio)-5-(2-methoxyethoxy)-7-(2-(4-methylpiperazin-1-yl)ethoxy)quinazoline | ++ | + | + |
| 4.1 | 4-((4-fluorophenyl)thio)-5-(2-methoxyethoxy)-7-(2-(4-methylpiperazin-1-yl)ethoxy)quinazoline | +++ | + | + |
| 4.2 | 4-((3,5-dichlorophenyl)thio)-5-(2-methoxyethoxy)-7-(2-(4-methylpiperazin-1-yl)ethoxy)quinazoline | ++ | ++ | + |
| 4.3 | 4-((3,5-difluorophenyl)thio)-5-(2-methoxyethoxy)-7-(2-(4-methylpiperazin-1-yl)ethoxy)quinazoline | ++ | ++ | + |
| 4.4 | 4-((2,4-dichlorophenyl)thio)-5-(2-methoxyethoxy)-7-(2-(4-methylpiperazin-1-yl)ethoxy)quinazoline | ++ | ++ | + |
| 4.5 | 4-((3-bromo-4-fluorophenyl)thio)-5-(2-methoxyethoxy)-7-(2-(4-methylpiperazin-1-yl)ethoxy)quinazoline | ++++ | ++ | + |
| 4.7 | 4-(2-chloro-4-fluorophenoxy)-7-((1-methylpiperidin-4-yl)methoxy)-5-((tetrahydro-2H-pyran-4-yl)oxy)quinazoline | ++++ | +++ | ++++ |
| 4.8 | 4-(3-((4-(2-chloro-4-fluorophenoxy)-5-morpholinoquinazolin-7-yl)oxy)propyl)morpholine | ++ | + | ++ |
| 4.9 | 4-(3-((4-(2-chloro-4-fluorophenoxy)-5-(4-methylpiperazin-1-yl)quinazolin-7-yl)oxy)propyl)morpholine | ++++ | + | ++ |
| 4.10 | 7-((1-methylpiperidin-4-yl)methoxy)-5-((tetrahydro-2H-pyran-4-yl)oxy)-4-(3-(trifluoromethyl)phenoxy)-quinazoline | ++++ | +++ | +++ |
| 4.11 | 7-((1-methylpiperidin-4-yl)methoxy)-5-((tetrahydro-2H-pyran-4-yl)oxy)-4-(4-(trifluoromethyl)phenoxy)quinazoline | ++++ | ++++ | +++ |
| 5 | (R)-3-((4-(2-chloro-4-fluorophenoxy)-5-((tetrahydro-2H-pyran-4-yl)oxy)quinazolin-7-yl)oxy)propane-1,2-diol | +++ | ++ | +++ |
| 6 | 4-isopropoxy-7-((1-methylpiperidin-4-yl)methoxy)-5-((tetrahydro-2H-pyran-4-yl)oxy)quinazoline | ++++ | ++++ | ++++ |
| 7 | N7-(2-(diethylamino)ethyl)-5-((tetrahydro-2H-pyran-4-yl)oxy)-N4-(4-(trifluoromethyl)thiazol-2-yl)quinazoline-4,7-diamine | + | ++ | + |
| 8 | 7-((1-methylpiperidin-4-yl)methoxy)-5-((tetrahydro-2H-pyran-4-yl)oxy)-N-(1H-1,2,4-triazol-5-yl)quinazolin-4-amine | + | + | + |

Example 10

Cell Viability Assay

Cell lines and reagents: A549 cells were cultured in Dulbecco's Modified Eagle Medium (DMEM, HyClone) containing 10% fetal bovine serum (FBS, Life technologies) and maintained in a humidified incubator at 37° C. with 5% $CO_2$.

Cell viability assay protocol: $5 \times 10^3$ A549 cells in 180 µL of DMEM containing 0.5% FBS were seeded in 96-well flat bottom plates (Costar) and incubated in a humidified incubator at 37° C. with 5% $CO_2$ for 24 hours. The test compound (20 µL) in different concentrations after a serial dilution was added to the wells to a final volume of 200 µL per well. The wells with zero compound concentration were used as the Control wells and the Test wells contained different concentrations of the test compound. To the Blank wells were added medium only. After 48 hours incubation, 40 µL of MTS (Promega) was added to each well and the plates were incubated for 10 minutes to 1 hour at 37° C. The cell viability was estimated by measurement of optical density at 490 nm using a microplate spectrophotometer (Molecular Devices).

Example 11

Thymidine Incorporation Assay $1 \times 10^4$ A549 cells in 180 µL of DMEM containing 0.5% FBS were seeded in a 96-well white Isoplate (PerkinElmer) and incubated in a humidified incubator at 37° C. with 5% $CO_2$ for 24 hours. The test compound in different concentrations after a serial dilution was added to the wells to a final volume of 200 µL per well. The wells with zero compound concentration were used as the Control wells and the wells containing different concentrations of the test compound were used as the Test wells. To the Blank wells were added water only. After 24-hour incubation, each well was labeled with 1 µCi of [$^3$H]thymidine (specific activity, 26.8 Ci/mmol, PerkinElmer), and plates were again incubated at 37° C. overnight. After incubation, 50 µL of cold trichloroacetic acid was added into each well and the plates were incubated at 4° C. for 1-2 hours. Plates were subsequently washed with distilled water 5 times and air-dried at room temperature. Scintillation liquid was added to each well and radioactivity in CPM was counted using a MicroBeta TriLux (PerkinElmer) counter. The corrected CPM in each well was determined by subtracting the average value of the Blank well values. Percentage of inhibition of the thymidine incorporation at tested concentrations by the test compound was determined using the following formula:

$$\% \text{ Inhibition} = \left(1 - \frac{\text{Average of corrected } CPM \text{ in Test wells}}{\text{Average of corrected } CPM \text{ in Control wells}}\right) \times 100$$

The $IC_{50}$ was then estimated from the curve of % Inhibition against concentration in log unit using Prism 5, version 5.01.

Example 12

Colony Formation Assay (Method #1)

A549 cells were treated with the test compound at different concentrations (5, 1 and 0.2 µM) in DMEM containing 0.5% FBS at 37° C. for 1 hour. After treatment, cells were seeded in agar containing the test compound at different concentrations as outlined above in 6-well plates and the plates were incubated at 37° C. for 2 weeks. DMEM containing the various concentrations of the test compound was added on the top of agar and changed every 2-3 days. The viable colonies were stained with crystal violet and counted. This example is to demonstrate the capability of test compounds to prevent the formation of colonies.

Example 13

Colony Formation Assay (Method #2)

17,500 A549 cells were seeded in agar in each well of 6-well plates and cultured in DMEM containing 10% FBS at 37° C. for six days in order to form colonies. The test compound dissolved in DMEM with different concentrations was added to the test wells of the plates and DMEM with no test compound or with diluted DMSO was added to the control wells. The plates were incubated at 37° C. for 18-20 days during which period the DMEM containing 10% FBS and the various concentrations of test compounds was changed every 2 to 3 days. The viable colonies were stained with crystal violet and counted. This example is to demonstrate the capability of test compounds to inhibit colony growth after they are established and/or to eliminate the established colonies.

Example 14

Western Blot Assay $5 \times 10^5$ A549 cells were starved in DMEM containing no FBS in 6-well plate overnight, and treated with different concentrations of test compounds in serum-free medium for 30 minutes at 37° C. Cells were subsequently stimulated with or without Gas6 (400 ng/mL) for 30 min at 37° C. Total proteins were extracted from the test compound treated cells using ice-cold RIPA buffer (50 mM Tris-HCl, pH 7.5, 150 mM NaCl, 1 mM EDTA, 1% (v/v) Triton-X 100, 0.1 (w/v) SDS) supplemented with protease inhibitor cocktail and phosphatase inhibitors. Protein concentrations were determined using Bradford assay. Twenty micrograms of total proteins were fractionated on 10% SDS-PAGE gels and transferred onto nitrocellulose membrane (Bio-rad). Transfer efficiency and loading were confirmed by reversible staining of the membrane with Ponseau S solution (MP Biomedicals) following protein transfer. Membranes were blocked at room temperature with 5% non-fat dry milk in Tris-buffered saline (TBS) containing 0.1% Tween-20 (TBST) for 1 hour and incubated with primary antibodies against Axl, Tyro3, phospho-AKT (Ser$^{473}$), total AKT or β-actin at 4° C. After overnight incubation, membranes were washed with TBST and incubated with a secondary horseradish peroxidase (HRP)-labeled antibody (Jackson ImmunoResearch Laboratories, Inc.) for 1 hour at room temperature. Membranes were washed in TBST following incubation with secondary antibodies. Bound antibody complexes were detected and visualized using Luminata Classico Western HRP Substrate (Millipore).

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A method of treating or ameliorating a disease, syndrome, condition or disorder that is affected by modulating the activity of a TAM kinase, comprising administering to a subject in need thereof, a therapeutically effective amount of a compound of formula (I):

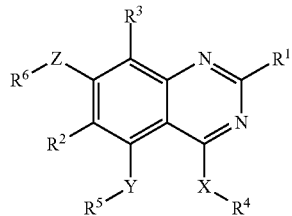

wherein:
X is selected from —C(R$^9$)$_2$—, —N(R$^{10}$)—, —O—, and —S(O)$_t$— where t is 0, 1, or 2;
Y and Z are independently selected from —C(R$^9$)$_2$—, —N(R$^{10}$)—, —O—, —S(O)$_t$— where t is 0, 1, or 2, and a heterocyclic moiety which contains 1 to 3 heteroatoms independently selected from O, N and S;
R$^1$ is selected from hydrogen, alkyl, cycloalkyl, cycloalkylalkyl, haloalkyl, aryl, heterocyclyl, heteroaryl, cyano, amino, alkoxy, and hydroxyl;
R$^2$ and R$^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;
R$^4$ is selected from alkyl, aralkyl, alkenyl, aralkenyl, alkynyl, aralkynyl, cycloalkyl, cycloalkylalkyl and haloalkyl; or R$^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-R$^{4a}$, where R$^4$ is not pyrazole;
Q is a direct bond, or a straight or branched alkylene chain;
L is selected from —N(R$^{10}$)—, —O—, —C(O)—, —C(O)O—, —S(O)$_t$— where t is 0, 1, or 2, —CON(R$^{10}$)—, —N(R$^{10}$)CO—, —SO$_2$N(R$^{10}$)—, —N(R$^{10}$)SO$_2$—, and —N(R$^{10}$)CON(R$^{10}$)—;
R$^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;
R$^5$ and R$^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —R$^7$—V—R$^8$ where V is selected from —N(R$^{10}$)—, or —O—;
R$^7$ is a straight or branched alkylene chain;
R$^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;
R$^9$ is selected from hydrogen, alkyl, halo, and haloalkyl;
R$^{10}$ is selected from hydrogen, alkyl, cycloalkyl, cycloalkylalkyl, and haloalkyl;
a stereoisomer, enantiomer or tautomer thereof, an isotopically enriched derivative thereof, a pharmaceutically acceptable salt thereof, or a prodrug thereof.

2. The method of claim 1 wherein R$^1$ is hydrogen.
3. The method of claim 1 wherein R$^2$ is hydrogen.
4. The method of claim 1 wherein R$^2$ is alkoxy.
5. The method of claim 1 wherein R$^3$ is hydrogen.
6. The method of claim 1 wherein R$^4$ is selected from alkyl, aralkyl, alkenyl, aralkenyl, alkynyl, aralkynyl, cycloalkyl, cycloalkylalkyl and haloalkyl.
7. A method of treating or ameliorating a disease, syndrome, condition or disorder that is affected by modulating the activity of a TAM kinase, comprising administering to a subject in need thereof, a therapeutically effective amount of a compound of formula (II):

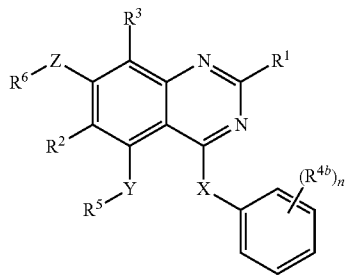

wherein:
X is selected from —C(R$^9$)$_2$—, —O—, and —S(O)$_t$— where t is 0, 1, or 2;
Y and Z are independently selected from —C(R$^9$)$_2$—, —N(R$^{10}$)—, —O—, —S(O)$_t$— where t is 0, 1, or 2, and a heterocyclic moiety which contains 1 to 3 heteroatoms independently selected from O, N and S;
R$^1$ is selected from hydrogen, alkyl, cycloalkyl, cycloalkylalkyl, haloalkyl, aryl, heterocyclyl, heteroaryl, cyano, amino, alkoxy, and hydroxyl;
R$^2$ and R$^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;
R$^{4b}$ is independently selected from alkyl, cycloalkyl, cycloalkylalkyl, haloalkyl, halo, cyano, amino, alkoxy, hydroxyl and Q-L-R$^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;
n is 0, 1, 2, 3, 4, or 5;
Q is a direct bond, or a straight or branched alkylene chain;
L is selected from —N(R$^{10}$)—, —O—, —C(O)—, —C(O)O—, —S(O)$_t$— where t is 0, 1, or 2, —CON(R$^{10}$)—, —N(R$^{10}$)CO—, —SO$_2$N(R$^{10}$)—, —N(R$^{10}$)SO$_2$—, and —N(R$^{10}$)CON(R$^{10}$)—;
R$^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;
R$^5$ and R$^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —R$^7$—V—R$^8$ where V is selected from —N(R$^{10}$)—, or —O—;
R$^7$ is a straight or branched alkylene chain;
R$^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

8. The method of claim 7 wherein $R^1$ is hydrogen.

9. The method of claim 7 wherein $R^2$ is hydrogen.

10. The method of claim 7 wherein $R^3$ is hydrogen.

11. The method of claim 7 wherein $R^5$ is heterocycle.

12. A compound of formula (I):

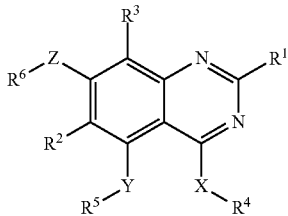

(I)

wherein:

X is selected from $-C(R^9)_2-$, $-N(R^{10})-$, $-O-$, and $-S(O)_t-$ where t is 0, 1, or 2;

Y and Z are independently selected from $-C(R^9)_2-$, $-N(R^{10})-$, $-O-$, $-S(O)_t-$ where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole;

Q is a direct bond, or a straight or branched alkylene chain;

L is selected from $-N(R^{10})-$, $-O-$, $-C(O)-$, $-C(O)O-$, $-S(O)_t-$ where t is 0, 1, or 2, $-CON(R^{10})-$, $-N(R^{10})CO-$, $-SO_2N(R^{10})-$, $-N(R^{10})SO_2-$, and $-N(R^{10})CON(R^{10})-$;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and $-R^7-V-R^8$ where V is selected from $-N(R^{10})-$, or $-O-$;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, or a prodrug thereof.

13. A pharmaceutical composition comprising the compound of claim 12.

14. A compound of formula (I):

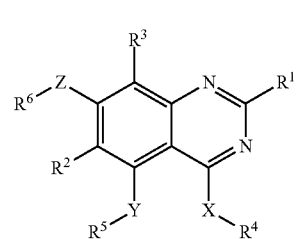

(I)

wherein X is $-O-$; Y is $-O-$;

Z is selected from $-C(R^9)_2-$, $-N(R^{10})-$, $-O-$, $-S(O)_t-$ where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^4$ is selected from alkyl, aralkyl, alkenyl, aralkenyl, alkynyl, aralkynyl, cycloalkyl, cycloalkylalkyl and haloalkyl; or $R^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-$R^{4a}$, where $R^4$ is not pyrazole;

Q is a direct bond, or a straight or branched alkylene chain;

L is selected from $-N(R^{10})-$, $-O-$, $-C(O)-$, $-C(O)O-$, $-S(O)_t-$ where t is 0, 1, or 2, $-CON(R^{10})-$, $-N(R^{10})CO-$, $-SO_2N(R^{10})-$, $-N(R^{10})SO_2-$, and $-N(R^{10})CON(R^{10})-$;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ is heterocycle;

$R^6$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and $-R^7-V-R^8$ where V is selected from $-N(R^{10})-$, or $-O-$;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, or a prodrug thereof.

15. A pharmaceutical composition comprising a compound of claim 14.

16. A compound of formula (II):

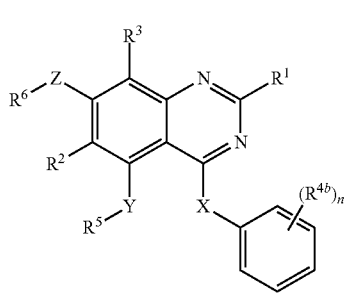

wherein:

X is selected from —C($R^9$)$_2$—, —O—, and —S(O)$_t$— where t is 0, 1, or 2;

Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ is alkoxy;

$R^3$ is selected from hydrogen, alkyl, aralkyl, cycloalkyl, cycloalkylalkyl, haloalkyl, halo, heterocyclyl, heterocyclylalkyl, alkoxy and alkoxyalkyl;

$R^{4b}$ is independently selected from alkyl, cycloalkyl, cycloalkylalkyl, haloalkyl, halo, cyano, amino, alkoxy, hydroxyl and Q-L-$R^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;

n is 0, 1, 2, 3, 4, or 5;

Q is a direct bond, or a straight or branched alkylene chain;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

17. A pharmaceutical composition comprising a compound of claim 16.

18. A compound of formula (II):

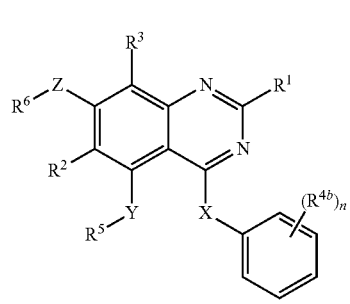

wherein:

X is selected from —C($R^9$)$_2$—, —O—, and —S(O)$_t$— where t is 0, 1, or 2;

Y and Z are independently selected from —C($R^9$)$_2$—, —N($R^{10}$)—, —O—, —S(O)$_t$— where t is 0, 1, or 2, and a heterocyclic moiety which contains 1 to 3 heteroatoms independently selected from O, N and S;

$R^1$ is selected from hydrogen, alkyl, cycloalkyl, cycloalkylalkyl, haloalkyl, aryl, heterocyclyl, heteroaryl, cyano, amino, alkoxy, and hydroxyl;

$R^2$ and $R^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;

$R^{4b}$ is halo and n is 1 or 2 or 3 or 4 or 5;

L is selected from —N($R^{10}$)—, —O—, —C(O)—, —C(O)O—, —S(O)$_t$— where t is 0, 1, or 2, —CON($R^{10}$)—, —N($R^{10}$)CO—, —SO$_2$N($R^{10}$)—, —N($R^{10}$)SO$_2$—, and —N($R^{10}$)CON($R^{10}$)—;

$R^5$ and $R^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —$R^7$—V—$R^8$ where V is selected from —N($R^{10}$)—, or —O—;

$R^7$ is a straight or branched alkylene chain;

$R^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;

$R^9$ is selected from hydrogen, alkyl, halo, and haloalkyl;

$R^{10}$ is selected from hydrogen, alkyl, cycloalkyl, cycloalkylalkyl, and haloalkyl;

a stereoisomer, enantiomer or tautomer thereof, an isotopically enriched derivative thereof, a pharmaceutically acceptable salt thereof, and a prodrug thereof.

19. A pharmaceutical composition comprising a compound of claim 18.

20. A compound of formula (II):

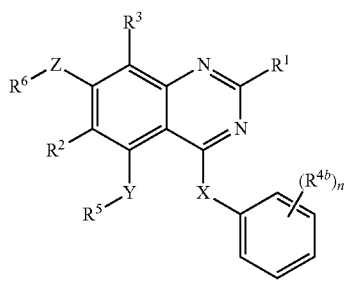

wherein:
n is zero; X is —O—; Y is —O—;
Z is selected from —C(R$^9$)$_2$—, —N(R$^{10}$)—, —O—, —S(O)$_t$— where t is 0, 1, or 2, and a heterocyclic moiety which contains 1 to 3 heteroatoms independently selected from O, N and S;
R$^1$ is selected from hydrogen, alkyl, cycloalkyl, cycloalkylalkyl, haloalkyl, aryl, heterocyclyl, heteroaryl, cyano, amino, alkoxy, and hydroxyl;
R$^2$ and R$^3$ are independently selected from hydrogen, alkyl, aralkyl, cycloalkyl, cycloalkylalkyl, haloalkyl, halo, heterocyclyl, heterocyclylalkyl, alkoxy and alkoxyalkyl;
R$^{4b}$ is independently selected from alkyl, cycloalkyl, cycloalkylalkyl, haloalkyl, halo, cyano, amino, alkoxy, hydroxyl and Q-L-R$^{4a}$; or two substituent groups at adjacent carbon atoms together to form a ring structure wherein the ring structure may be unsaturated or saturated, may be non-aromatic or aromatic, and may contain 1 to 2 heteroatoms selected from N, O, and S;
Q is a direct bond, or a straight or branched alkylene chain;
L is selected from —N(R$^{10}$)—, —O—, —C(O)—, —C(O)O—, —S(O)$_t$— where t is 0, 1, or 2, —CON(R$^{10}$)—, —N(R$^{10}$)CO—, —SO$_2$N(R$^{10}$)—, —N(R$^{10}$)SO$_2$—, and —N(R$^{10}$)CON(R$^{10}$)—;
R$^{4a}$ is selected from alkyl, aralkyl, alkenyl, aralkenyl, alkynyl, aralkynyl, cycloalkyl, cycloalkylalkyl, haloalkyl, aryl, heteroaryl, and heterocyclyl;
R$^5$ and R$^6$ are independently selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, alkylaminoalkyl, and —R$^7$—V—R$^8$ where V is selected from —N(R$^{10}$)—, or —O—;
R$^7$ is a straight or branched alkylene chain;
R$^8$ is selected from hydrogen, alkyl, aralkyl, alkenyl, aralkenyl, alkynyl, aralkynyl, cycloalkyl, cycloalkylalkyl, heteroaryl, heteroaralkyl, heterocyclyl, heterocyclylalkyl, alkoxyalkyl, and alkylaminoalkyl;
R$^9$ is selected from hydrogen, alkyl, halo, and haloalkyl;
R$^{10}$ is selected from hydrogen, alkyl, cycloalkyl, cycloalkylalkyl, and haloalkyl;
a stereoisomer, enantiomer or tautomer thereof, an isotopically enriched derivative thereof, a pharmaceutically acceptable salt thereof, and a prodrug thereof.

21. A pharmaceutical composition comprising a compound of claim 20.

22. The method of claim 1 wherein R$^4$ is a 5-membered monocyclic heteroaryl moiety which contains 1 to 3 heteroatoms independently selected from O, N and S wherein the heteroaryl moiety may be substituted with one or more substituents selected from alkyl, cycloalkyl, cycloalkylalkyl, haloalkyl, halo, cyano, amino, alkoxy, hydroxyl, aryl, aralkyl, heteroaryl, heteroarylalkyl, heterocyclyl, heterocyclylalkyl and Q-L-R$^{4a}$, where R$^4$ is not pyrazole.

23. The method of claim 1 wherein X is —O—.

24. The method of claim 1 wherein Y is —O—.

25. The method of claim 1 wherein R$^5$ is heterocyclyl.

26. The method of claim 1 wherein R$^6$ is —R$^7$—V—R$^8$ where V is selected from N(R$^{10}$) and —O—.

* * * * *